(12) United States Patent
Faham et al.

(10) Patent No.: US 8,691,510 B2
(45) Date of Patent: *Apr. 8, 2014

(54) SEQUENCE ANALYSIS OF COMPLEX AMPLICONS

(75) Inventors: Malek Faham, Pacifica, CA (US); Martin Moorhead, San Mateo, CA (US); Thomas Willis, San Francisco, CA (US)

(73) Assignee: Sequenta, Inc., San Francisco, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 13/100,389

(22) Filed: May 4, 2011

(65) Prior Publication Data

US 2011/0207135 A1    Aug. 25, 2011

Related U.S. Application Data

(63) Continuation-in-part of application No. 12/615,263, filed on Nov. 9, 2009, now Pat. No. 8,236,503.

(60) Provisional application No. 61/332,175, filed on May 6, 2010, provisional application No. 61/445,743, filed on Oct. 25, 2010, provisional application No. 61/446,822, filed on Feb. 25, 2011.

(51) Int. Cl.
*C12Q 1/68* (2006.01)
*C12P 19/34* (2006.01)

(52) U.S. Cl.
USPC .................. 435/6.12; 435/91.1; 435/91.2

(58) Field of Classification Search
USPC .................... 435/6.12, 91.1, 91.2
See application file for complete search history.

(56) References Cited

U.S. PATENT DOCUMENTS

| | | | |
|---|---|---|---|
| 5,296,351 A | 3/1994 | Morley | 435/6 |
| 5,298,396 A | 3/1994 | Kotzin et al. | |
| 5,336,598 A | 8/1994 | Kotzin et al. | |
| 5,418,134 A | 5/1995 | Morley | 435/6 |
| 5,635,354 A | 6/1997 | Kourilsky et al. | |
| 5,698,396 A | 12/1997 | Pfreundschuh | |
| 5,776,708 A | 7/1998 | Kotzin et al. | |
| 5,837,447 A | 11/1998 | Gorski | 435/6 |
| 6,087,096 A | 7/2000 | Dau | 435/6 |
| 6,090,592 A * | 7/2000 | Adams et al. | 435/91.2 |
| 6,258,568 B1 | 7/2001 | Nyren | |
| 6,416,948 B1 * | 7/2002 | Pilarski et al. | 435/6.14 |
| 6,596,492 B2 | 7/2003 | Avery et al. | |
| 6,667,159 B1 | 12/2003 | Walt | |
| 6,964,850 B2 | 11/2005 | Bevilacqua | |
| 7,306,906 B2 | 12/2007 | Maruyama et al. | |
| 7,375,211 B2 | 5/2008 | Kou | 536/24.33 |
| 7,691,994 B2 | 4/2010 | Brewer | 536/24.33 |
| 7,749,697 B2 | 7/2010 | Oleksiewicz et al. | |
| 8,283,294 B2 | 10/2012 | Kastrup et al. | |
| 8,628,927 B2 | 1/2014 | Faham et al. | |
| 2002/0076725 A1 | 6/2002 | Toyosaki-Maeda et al. | |
| 2003/0162197 A1 | 8/2003 | Morley et al. | |
| 2004/0248172 A1 | 12/2004 | Samoszuk et al. | |
| 2005/0064421 A1 | 3/2005 | Gehrmann | 435/6 |
| 2006/0046258 A1 | 3/2006 | Lapidus et al. | |
| 2006/0085139 A1 | 4/2006 | Collette et al. | |
| 2006/0088876 A1 | 4/2006 | Bauer | |
| 2006/0134125 A1 | 6/2006 | Luxembourg et al. | |
| 2006/0147925 A1 | 7/2006 | Morley et al. | |
| 2006/0234234 A1 | 10/2006 | Van Dongen | 435/6 |
| 2006/0259248 A1 | 11/2006 | Collette et al. | |
| 2007/0105105 A1 | 5/2007 | Clelland et al. | |
| 2007/0117134 A1 | 5/2007 | Kou | 536/24.33 |
| 2007/0160994 A1 * | 7/2007 | Lim et al. | 435/6 |
| 2007/0161001 A1 | 7/2007 | Leshkowitz | 435/6 |
| 2007/0238099 A1 | 10/2007 | Cohen et al. | |
| 2007/0286849 A1 | 12/2007 | Chaturvedi | |
| 2008/0108509 A1 | 5/2008 | Haupl | 506/8 |
| 2008/0166704 A1 | 7/2008 | Marche | 435/6 |
| 2008/0166718 A1 | 7/2008 | Lim et al. | |
| 2008/0248484 A1 | 10/2008 | Bauer | |
| 2008/0274904 A1 | 11/2008 | Gormley et al. | |
| 2008/0280774 A1 | 11/2008 | Burczynski | 506/9 |
| 2008/0286777 A1 | 11/2008 | Candeias | 435/6 |

(Continued)

FOREIGN PATENT DOCUMENTS

| | | | |
|---|---|---|---|
| EP | 1544308 B1 | 6/2005 | |
| EP | 1549764 B1 | 7/2005 | |

(Continued)

OTHER PUBLICATIONS

U.S. Appl. No. 13/763,978, filed Feb. 2013, Faham et al.*
U.S. Appl. No. 13/214,111, filed Aug. 19, 2011, Faham et al.
U.S. Appl. No. 13/369,031, filed Feb. 8, 2012, Faham et al.
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Costabile, et al. Molecular approaches in the diagnosis of primary immunodeficiency diseases. Hum Mutat. Dec. 2006;27(12):1163-73.
International search report and written opinion dated Sep. 22, 2011 for PCT Application No. US11/000791.
International search report and written opinion dated Oct. 19, 2011 for PCT Application No. US11/000792.
Kim, et al. Polony multiplex analysis of gene expression (PMAGE) in mouse hypertrophic cardiomyopathy. Science. Jun. 8, 2007;316(5830):1481-4.

(Continued)

*Primary Examiner* — Kenneth R. Horlick
*Assistant Examiner* — Joyce Tung
(74) *Attorney, Agent, or Firm* — Wilson Sonsini Goodrich & Rosati

(57) ABSTRACT

The invention is directed to methods of generating sequence profiles of populations of nucleic acids, whose member nucleic acids contain regions of high variability, such as populations of nucleic acids encoding T cell receptors or B cell receptors. In one aspect, the invention provides pluralities of sets of primers for generating nested sets of templates from nucleic acids in such populations, thereby insuring the production of at least one template from which sequence reads are generated, despite such variability, or dispite limited lengths or quality of sequence reads. In another aspect, members of such populations are bidirectionally sequenced so that further sequence information is obtained by analyzing overlapping sequence reads in the zones of highest variability.

14 Claims, 13 Drawing Sheets

(56) References Cited

U.S. PATENT DOCUMENTS

| | | | |
|---|---|---|---|
| 2009/0053184 A1 | 2/2009 | Morgan | 424/93.21 |
| 2009/0181859 A1 | 7/2009 | Muraguchi | |
| 2009/0197257 A1 | 8/2009 | Harris | |
| 2009/0226975 A1 | 9/2009 | Sabot et al. | |
| 2009/0280489 A1 | 11/2009 | Devinder | 435/6 |
| 2009/0298060 A1 | 12/2009 | Lal et al. | |
| 2010/0021896 A1 | 1/2010 | Han | 435/6 |
| 2010/0021984 A1 | 1/2010 | Edd et al. | |
| 2010/0035764 A1 | 2/2010 | Chen | 506/9 |
| 2010/0040606 A1 | 2/2010 | Lantto et al. | |
| 2010/0042329 A1 | 2/2010 | Hood et al. | |
| 2010/0151471 A1 | 6/2010 | Faham et al. | |
| 2010/0173394 A1 | 7/2010 | Colston, Jr. | |
| 2010/0255471 A1 | 10/2010 | Clarke | |
| 2010/0285975 A1 | 11/2010 | Mathies | |
| 2010/0330571 A1 | 12/2010 | Robins | 435/6 |
| 2011/0003291 A1 | 1/2011 | Pasqual | 435/6 |
| 2011/0207134 A1* | 8/2011 | Faham et al. | 435/6.11 |
| 2011/0207617 A1 | 8/2011 | Faham et al. | |
| 2012/0220466 A1 | 8/2012 | Fire et al. | |
| 2013/0005584 A1* | 1/2013 | Faham et al. | 506/2 |
| 2013/0017957 A1* | 1/2013 | Faham et al. | 506/2 |
| 2013/0344066 A1 | 12/2013 | Faham et al. | |

FOREIGN PATENT DOCUMENTS

| | | |
|---|---|---|
| JP | 2007-536939 A | 12/2007 |
| JP | 2008099588 A | 5/2008 |
| WO | WO 93/01838 A1 | 2/1993 |
| WO | WO 95/28481 A1 | 10/1995 |
| WO | WO 97/18330 A1 | 5/1997 |
| WO | WO 97/46706 A1 | 12/1997 |
| WO | WO 98/01738 A1 | 1/1998 |
| WO | WO 03/044225 A2 | 5/2003 |
| WO | WO 03/059155 A2 | 7/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/059176 A1 | 6/2005 |
| WO | WO 2005/084134 A2 | 9/2005 |
| WO | WO2006/076025 | 7/2006 |
| WO | WO 2006/116155 A2 | 11/2006 |
| WO | WO2008/026927 | 3/2008 |
| WO | WO 2008/039694 A2 | 4/2008 |
| WO | WO2008/108803 | 9/2008 |
| WO | WO2008/147879 | 12/2008 |
| WO | WO 2009/015296 A1 | 1/2009 |
| WO | WO 2009/019657 A2 | 2/2009 |
| WO | WO 2009/021215 A1 | 2/2009 |
| WO | WO2009/045898 | 4/2009 |
| WO | WO 2009/070767 A2 | 6/2009 |
| WO | WO 2009/019657 A3 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO2009/137255 | 11/2009 |
| WO | WO 2009/137832 A2 | 11/2009 |
| WO | WO 2009/145925 A1 | 12/2009 |
| WO | WO2009/151628 | 12/2009 |
| WO | WO 2009/158521 A2 | 12/2009 |
| WO | WO 2009/108860 A3 | 1/2010 |
| WO | WO 2010/011894 A1 | 1/2010 |
| WO | WO 2010/036352 A1 | 4/2010 |
| WO | WO 2009/158521 A3 | 5/2010 |
| WO | WO2010/051416 | 12/2010 |
| WO | WO 2011/083296 A1 | 7/2011 |
| WO | WO 2011/106738 A2 | 9/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/048340 A2 | 4/2012 |
| WO | WO 2012/048340 A3 | 6/2012 |

OTHER PUBLICATIONS

Margulies, et al. Genome sequencing in microfabricated high-density picolitre reactors. Nature. Sep. 15, 2005;437(7057):376-80. Epub Jul. 31, 2005.

Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.

UK office action dated May 25, 2011 for UK application No. GB1009641.0.

UK office action dated Oct. 20, 2010 for UK application No. GB1009641.0.

UK Search Report and office action dated Jan. 12, 2012 for UK application No. GB1120209.0.

UK Search Report and office action dated Jul. 7, 2010 for UK application No. GB1009641.0.

Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.

U.S. Appl. No. 13/763,978, filed Feb. 11, 2013, Faham et al.

Alatrakchi, et al. T-cell clonal in patients with B-cell lymphoproliferative disorders. J Immunother. Sep. 1998;21(5):363-70.

Bruggemann, et al. Standardized MRD quantification in European All trials: proceedings of the Second International Symposium on MRD assessment in Kiel, Germany, Sep. 18-20, 2008. Leukemia. Mar. 2010;24(3):521-35. doi: 10.1038/leu.2009.268. Epub Dec. 24, 2009.

Gerlinger, et al. How Darwinian models inform therapeutic failure initiated by clonal heterogeneity in cancer medicine. Br J Cancer. Oct. 12, 2010;103(8):1139-43. doi: 10.1038/sj.bjc.6605912. Epub Sep. 28, 2010.

Guo, et al. Sequence changes at the V-D junction of the VH1 heavy chain of anti-phosphocholine antibodies alter binding to and protection against Streptococcus pneumoniae. Int Immunol May 1997;9(5):665-77.

Howe, et al. T cell receptor clonotype analysis of T cell responses: Diagnostic application of a clonotypic database. Blood. 2003; 102:Abstract 3918.

Office action dated Mar. 13, 2013 for U.S. Appl. No. 13/763,978.

Office action dated Mar. 20, 2013 for U.S. Appl. No. 13/487,980.

Office action dated Dec. 6, 2012 for U.S. Appl. No. 13/100,395.

Sfanos, et al. Phenotypic analysis of prostate-infiltrating lymphocytes reveals TH17 and Treg skewing. Clin Cancer Res. Jun. 1, 2008;14(11):3254-61. doi: 10.1158/1078-0432.CCR-07 5164.

Sing, et al. A molecular comparison of T lymphocyte populations infiltrating the liver and circulating in the blood of patients with chronic hepatitis B: evidence for antigen-driven selection of a public complementarity-determining region 3 (CDR3) motif. Hepatology. May 2001;33(5):1288-98.

Szczepanski, et al. Comparative analysis of Ig and TCR gene rearrangements at diagnosis and at relapse of childhood precursor-B-ALL provides improved strategies for selection of stable PCR targets for monitoring of minimal residual disease. Blood. Apr. 1, 2002;99(7):2315-23.

Szczepanski, et al. Why and how to quantify minimal residual disease in acute lymphoblastic leukemia? Leukemia. Apr. 2007;21(4):622-6. Epub Feb. 15, 2007.

UK combined search and examination report dated Mar. 20, 2013 for GB 1300533.5.

Van Der Velden, et al. Analysis of minimal residual disease by Ig/TCR gene rearrangements: guidelines for interpretation of real-time quantitative PCR data. Leukemia. Apr. 2007;21(4):604-11. Epub Feb. 8, 2007.

(56) References Cited

OTHER PUBLICATIONS

Van Der Velden, et al. Detection of minimal residual disease in hematologic malignancies by real-time quantitative PCR: principles, approaches, and laboratory aspects. Leukemia. Jun. 2003;17(6):1013-34.
Arstila et al, "A direct estimate of the human αβ T cell receptor diversity," Science, 286: 958-961 (1999).
Batzoglou, "The many faces of the sequence alignment," Briefings in Bioinformatics, 6: 6-22 (2005).
Boria et al, "Primer sets for cloning the human repertoire of T cell receptor variable regions." BMC Immunology, 9: 50 (2008).
Boyd et al, "Measurement and clinical monitoring of human lymphocyte clonality by massively parallel VDJ pyrosequencing," Science Transl. Med. 1(12): 12ra23 (2009).
Campbell et al, "Subclonal phylogenic structures in cancer revealed by ultra-deep sequencing," Proc. Natl. Acad. Sci., 105(35): 13081-13086 (2008).
Dohm et al, "Substanial biases in ultra-short read data sets from high-throughput DNA sequencing," Genome Research, 19(10): 1817-1824 (2009).
Du et al, "TCR spectrotyping revealed T lymphocytes associated with graft-versus-host disease after allogenic hematopoietic stem cell transplantation," Leukemia & Lymphoma, 48(8): 1618-1627 (2007).
Freeman et al, "Profiling the T-cell receptor beta-chain repertoire by massively parallel sequencing," Genome Research, 19(10): 1817-1824 (2009).
Han, et al. Immunorepertoire analysis by multiplex PCR amplification and high throughput sequencing. Abstract. The 96 Annual Meeting of The Americ.an Association ofImmunologists, Seattle, Washington, May 8-12, 2009. Available at http://jimmunol.org//cgi/contentimeeting_abstract[I82/1_MeetingAbstracts/42.6?sid=257929fl-97a9-4330-8e96-1750aa240e69. Accessed 11/24/2010.
Holt, "Q & A: BC Cancer Angency's Robert Holt on sequencing the immune repertoire," Genome Web (www.genomeweb.com) (Jun. 30, 2009).
International Search Report dated Jun. 15, 2010 for PCT/US2009/006053.
Li et al, "Sequence analysis of clonal immunoglobulin and T-cell receptor gene rearrangements in child red with acute lymphoblastic leukemia at diagnosis and at relapse: implications for pathogenesis and for the clinical utility of PCR-based methods of minimal residual disease detection," Blood, 102: 4520-4526 (2003).
Packer et al, "Optimized clonotypic analysis of T-cell receptor repertoire in immune reconstitution," Experimental Hematology, 35: 516-521 (2007).
Pop, et al. Bioinformaticschallenges of new sequencing technology. Trends Genet. Mar. 2008;24(3): 142-9,
Reinartz, et al. "Massively parrelel signature sequencing (MPSS) as a tool in-depth quantitative gene expression profiling in all organisms," Briefings in Functional Genomics and Proteomics, 1(1): 95-104 (Feb. 2002).
Robins et al, "Comprehensive assessment of T-cell receptor β chain diversity in αβ T cells," Blood, 114(19): 4099-4107 (2009).
Rougemont et al, "Probabilistic base calling of Solexa sequencing data," BMC Bioinformatics, 9: 431 (2008).
Wang, et al, High throughput sequencing reveals a complex pattern of dynamic interrelationships among human T cell subsets. Proc Natl Acad Sci USA. Jan. 26, 2010: 107(4): 1518-1523.
Weinstein et al, "High throughput sequencing of the zebrafish antibody repertoire," Science, 324; 607-810 (2009).
Zhou et al, "High throughout analysis of TCR-β rearrangement and gene expression in single cells." Laboratory Investigation, 86: 314-321 (2006).
U.S. Appl. No. 13/861,941, filed Apr. 12, 2013, Pepin et al.
Wu, et al. High-throughput sequencing detects minimal residual disease in acute T lymphoblastic leukemia. Sci Transl Med. May 16 2012;4(134):134ra63. doi: 10.1126/scitranslmed.3003656.
U.S. Appl. No. 13/459,701, filed Apr. 30, 2012, Faham et al.
U.S. Appl. No. 13/468,323, filed May 10, 2010, Faham et al.

European office action dated Mar. 28, 2012 for EP Application No. 09764927.1.
Illumina. Data Sheet: Sequencing. Genomic Sequencing. Pub. No. 770.2008-016 Copyright 2010. Reference states: "Current as of Jan. 30, 2009".
Office action dated May 9, 2012 for U.S. Appl. No. 13/100,395.
Office action dated Sep. 15, 2011 for U.S. Appl. No. 12/615,263.
U.S. Appl. No. 13/487,980, filed Jun. 4, 2012, Faham et al.
Bonarius, et al. Monitoring the T-Cell Receptor Repertoire at Single-Clone Resolution. PLoS One. Dec. 20, 2006;1:e55.
UK Combined Search Report and Office action dated Jun. 29, 2012 for UK application No. GB1209668.1.
Wang, et al. Quantitative measurement of pathogen-specific human memory T cell repertoire diversity using a CDR3 beta-specific microarray. BMC Genomics. Sep. 19, 2007;8:329.
U.S. Appl. No. 13/174,086, filed Jun. 30, 2011, Faham et al.
U.S. Appl. No. 13/196,885, filed Aug. 2, 2011, Faham et al.
U.S. Appl. No. 61/045,586, filed Apr. 16, 2008, Han et al.
Bene, et al. How and why minimal residual disease studies are necessary in leukemia: a review from WP10 and WP12 of the European LeukaemiaNet. Haematologica. Aug. 2009;94(8):1135-50. Epub Jul. 7, 2009.
Benichou, et al. Rep-Seq: uncovering the immunological repertoire through next-generation sequencing. Immunology. Mar. 2012;135(3):183-91. doi: 10.1111/j.1365-2567.2011.03527.x.
Boyd, et al. Individual variation in the germline Ig gene repertoire inferred from variable region gene rearrangements. J Immunol Jun. 15, 2010;184(12):6986-92. Epub May 21, 2010.
Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.
Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.
Campana. Minimal residual disease in acute lymphoblastic leukemia. Semin Hematol. Jan. 2009;46(1):100-6.
Choi, et al. Relapse in children with acute lymphoblastic leukemia involving selection of a preexisting drug-resistant subclone. Blood. Jul. 15, 2007;110(2):632-9. Epub Mar. 19, 2007.
Currier, et al. Spectratype/immunoscope analysis of the expressed TCR repertoire. Current Protocols in Immunology. 2000; Supplement 38:10.28.1-10.28.24.
Gorski, et al. Circulating T cell repertoire complexity in normal individuals and bone marrow recipients analyzed by CDR3 size spectratyping. Correlation with immune status. J Immunol May 15, 1994;152(10):5109-19.
Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.
Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.
Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.
Lovisa, et al. IGH and IGK gene rearrangements as PCR targets for pediatric Burkitt's lymphoma and mature B-ALL MRD analysis. Lab Invest. Oct. 2009;89(10):1182-6. Epub Aug. 10, 2009.
Meleshko, et al. Rearrangements of IgH, TCRD and TCRG genes as clonality marker of childhood acute lymphoblastic leukemia. Exp Oncol. Dec. 2005;27(4):319-24.
Moss, et al. The human T cell reeptor in health and disease. Annu. Rev. Immunol. 1992; 10:71-96.
Neale, et al. Comparative analysis of flow cytometry and polymerase chain reaction for the detection of minimal residual disease in childhood acute lymphoblastic leukemia. Leukemia. May 2004;18(5):934-8.

(56) References Cited

OTHER PUBLICATIONS

Nguyen, et al. Identification of errors introduced during high throughput sequencing of the T cell receptor repertoire. BMC Genomics. Feb. 11, 2011;12:106.

Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.

Reddy, et al. Systems analysis of adaptive immunity by utilization of high-throughput technologies. Curr Opin Biotechnol. Aug. 2011;22(4):584-9. Epub May 12, 2011.

Robins, et al. Ultra-sensitive detection of rare T cell clones. Immunol Methods. Jan. 31, 2012;375(1-2):14-9. Epub Sep. 10, 2011.

Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.

Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.

Dou, et al. Analysis of T cell receptor Vbeta gene usage during the course of disease in patients with chronic hepatitis B. J Biomed Sci. Nov.-Dec. 1998;5(6):428-34.

Pira, et al. Human naive CD4 T-cell clones specific for HIV envelope persist for years in vivo in the absence of antigenic challenge. J Acquir Immune Defic Syndr. Oct. 1, 2005;40(2):132-9.

Ria, et al. Collagen-specific T-cell repertoire in blood and synovial fluid varies with disease activity in early rheumatoid arthritis. Arthritis Res Ther. 2008;10(6):R135. Epub Nov. 17, 2008.

Rickinson, et al. Human cytotoxic T lymphocyte responses to Epstein-Barr virus infection. Annu Rev Immunol 1997;15:405-31.

Schaufelberger, et al. An uneven expression of T cell receptor V genes in the arterial wall and peripheral blood in giant cell arteritis. Inflammation. Dec. 2008;31(6):372-83.

Scholler, et al. Analysis of T cell receptor alpha beta variability in lymphocytes infiltrating melanoma primary tumours and metastatic lesions. Cancer Immunol Immunother. Oct. 1994;39(4):239-48.

Struyk, et al. T cell receptors in rheumatoid arthritis. Arthritis Rheum. May 1995;38(5):577-89.

Bagnara, et al. IgV gene intraclonal diversification and clonal evolution in B-cell chronic lymphocytic leukaemia. Br J Haematol. Apr. 2006;133(1):50-8.

Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.

Davi, et al. Lymphocytic progenitor cell origin and clonal evolution of human B-lineage acute lymphoblastic leukemia. Blood. Jul. 15, 1996;88(2):609-21.

Germano, et al. Clonality profile in relapsed precursor-B-ALL children by GeneScan and sequencing analyses. Consequences on minimal residual disease monitoring. Leukemia. Aug. 2003;17(8):1573-82.

Golembowski, et al. Clonal evolution in a primary cutaneous follicle center B cell lymphoma revealed by single cell analysis in sequential biopsies. Immunobiology. Apr. 2000;201(5):631-44.

Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.

Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.

Langerak, et al. Immunoglobulin/T-cell receptor clonality diagnostics. Exoert Opin. Med. Diagn. 2007; 1(3):451-461.

Li, et al. Clonal rearrangements in childhood and adult precursor B acute lymphoblastic leukemia: a comparative polymerase chain reaction study using multiple sets of primers. Eur J Haematol. Oct. 1999;63(4):211-8.

Li, et al. Detailed clonality analysis of relapsing precursor B acute lymphoblastic leukemia: implications for minimal residual disease detection. Leukemia Research. 2001; 25:1033-1045.

Matolcsy, et al. Clonal evolution of B cells in transformation from low- to high-grade lymphoma. Eur J Immunol. Apr. 1999;29(4):1253-64.

Pels, et al. Clonal evolution as pathogenetic machanism in relapse of primary CNS lymphoma. Neurology. Jul. 13, 2004;63(1):167-9.

Rosenquist, et al. Clonal evolution as judged by immunoglobulin heavy chain gene rearrangements in relapsing precursor-B acute lymphoblastic leukemia. Eur J Haematol Sep. 1999;63(3):171-9.

Ryan, et al. Clonal evolution of lymphoblastoid cell lines. Lab Invest. Nov. 2006;86(11):1193-200. Epub Oct. 2, 2006.

Steenbergen, et al. Distinct ongoing Ig heavy chain rearrangement processes in childhood B-precursor acute lymphoblastic leukemia. Blood. Jul. 15, 1993;82(2):581-9.

Steward, et al. A polymerase chain reaction study of the stability of Ig heavy-chain And T-cell receptor delta gene rearrangements between presentation and relapse of childhood B-lineage acute lymphoblastic leukemia. Blood. Mar. 1, 1994;83(5):1355-62.

U.S. Appl. No. 13/905,406, filed May 30, 2013, Faham et al.

U.S. Appl. No. 13/908,813, filed Jun. 3, 2013, Faham et al.

Chen, A novel approach for the analysis of T-cell reconstituion by using a T-cell receptor beta-based obgomicleotide microarmy in hematopoietic stem cell transplantation. Exp Hematol, May 2007;35(5):831-41.

Office action dated Jun. 6, 2013 for U.S. Appl. No. 13/100,365.

Office action dated Jun. 20, 2013 for U.S. Appl. No. 13/214,111.

Office action dated Jul. 5, 2013 for U.S. Appl. No. 13/763,978.

Office action dated Apr. 22, 2013 for U.S. Appl. No. 13/214,111.

Cronn, et al. Multiplex sequencing of plant chloroplast genomes using Solexa sequencing-by-synthesis technology. Nucleic Acids Res. Nov. 2008;36(19):e122.

Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).

Deng et al., "Gene profiling involved in immature CD4+ T lymphocyte responsible for systemic lupus erythematosus," Molecular Immunology 43:1497-1507 (2006).

Fritz et al., "Alterations in the spinal cord T cell repertoire during relapsing experimental autoimmune encephalomyelitis," J Immunol 164:6662-6668 (2000).

Garcia-Castello, et al. Detection of clonal immunoglobulin and T-cell receptor gene recombination in hematological malignancies: monitoring minimal residual disease. Cardiovascular & Haematological Disorders-Drug Targets. 2009; 9:124-135.

Gonzalez, et al. Incomplete DJH rearrangements as a novel tumar target for minimal residual disease quantitation in multiple myeloma using real-time PCR. Leukemia. 2003; 17:1051-1057.

Gonzalez, et al. Incomplete DJH rearrangements of the IgH gene are frequent in multiple myelioma patients: immunobioligcal characteristics and clinical applications. Leukemia. 2003; 17:1398-1403.

Heger, M. Studies Highlight Challenges of Immune Repertoire Sequencing's Clinical Applicability. Available at http://wvvw.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.

Ishii et al., "Isolation and expression profiling of genes upregulated in the peripheral blood cells of systemic lupus erythematosus patients," DNA Research 12:429-439 (2005).

Jacobi et al., "Activated memory B cell subsets correlate with disease activity in systemic lupus erythematosus: delineation by expression of CD27, IgD, and CD95," Arthritis & Rheumatism 58(6):1762-1773 (2008).

Jacobi et al., "Correlation between circulating CD27high plasma cells and disease activity in patients with systemic lupus erythematosus," Arthritis & Rheumatism 58(6):1762-1773 (2008).

(56) References Cited

OTHER PUBLICATIONS

Kato et al., "Analysis of accumulated T cell clonotypes in patients with systemic lupus erythematosus," Arthritis & Rheumatism 43(12):2712-2721 (2000).
Kneba, et al. Analysis of rearranged T-cell receptor beta-chain genes by polymerase chain reaction (PCR0 DNA sequencing and automated high resolution PCR fragment analysis. Blood. 1995; 86:3930-3937.
Laplaud et al., "Blood T-cell receptor β chain transcriptome in multiple sclerosis. Characterization of the T cells with altered CDR3 length distribution," Brain 127:981-995 (2004).
Laplaud et al., "Serial blood T cell repertoire alterations in multiple sclerosis patients; correlation with clinical and MRI parameters," J Neroimmunol 177:151-160 (2006).
Luo et al., "Analysis of the interindividual conservation of T cell receptor α- and β-chain variable regions gene in the peripheral blood of patients with systemic lupus erythematosus," Clin Exp Immunol 154:316-324 (2008).
Mato et al., "Correlation of clonal T cell expansion with disease activity in systemic lupus erythematosus," Int Immunol 9(4):547-554 (1997).
Matsumoto et al., "CDR3 spectratyping analysis of the TCR repertoire in myasthenia gravis," J Immunol 176:5100-5107 (2006).
Matsumoto et al., "Complementarity-determining region 3 spectratyping analysis of the TCR repertoire in multiple sclerosis," J Immunol 170:4846-4853 (2003).
Menezes et al., "A public T cell clonotype within a heterogeneous autoreactive repertoire is dominant in driving EAE," J Clin Invest 117(8):2176-2185 (2007).
Michalek, et al. Detection and long-term in vivo monitoring of individual tumor-specific T cell clones in patients with metastatic melanoma. J Immunol. Jun. 1, 2007;178(11):6789-95.
Muraro et al., "Molecular tracking of antigen-specific T cell clones in neurological immune-mediated disorders," Brain 126:20-31 (2003).
Notification of Grant dated Jul. 26, 2011 for patent serial No. GB 2467704.
Ogle, et al. Direst measurement of lymphocyte receptor diversity. Nucleic Acids Research. 2003; 31(22):e139.
Okajima et al., "Analysis of T cell receptor Vβ diversity in peripheral CD4+ and CD8+ T lymphocytes in patients with autoimmune thyroid diseases," Clin Exp Immunol 155:166-172 (2008).
Risitano et al., "In-vivo dominant immune responses in aplastic anaemia: molecular tracking of putatively pathogenetic T-cell clones by TCR β-CDR3 sequencing," Lancet 364:355-364 (2004).
Schwab et al., "CD8+ T-cell clones dominate brain infiltrates in Rasmussen encephalitis and persist in the periphery," Brain 132:1236-1246 (2009).
Shen, et al. Comparing platforms for *C. elegans* mutant identification using high, throughput whole-genome sequencing. PLoS One. 2008;3(12):e4012.
Skulina et al., "Multiple sclerosis:. brain-infiltrating CD8+ T cells persist as clonal expansions in the cerebrospinal fluid and blood," PNAS 101(8):2428-2433 (2004).
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Tackenberg et al., "Clonal expansions of CD4+ β helper T cells in autoimmune myasthenia gravis," Eur J Immunol 37:849-863 (2007).
UK Combined Search Report and Office action dated May 26, 2011 for UK application No. GB1105068.9.
UK Search Report dated Jul. 6, 2010 for UK application No. GB1009641.0.
Umibe et al., "Clonal expansion of T cells infiltrating in the airways of non-atopic asthmatics," Clin Exp Immunol 119:390-397 (2000).
Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Brehm-Stecher, et al. Single-cell microbiology: tools, technologies, and applications. Microbiology and molecular biology reviews. 2004; 68(3):538-559.
Davis, et al. Staining of cell surface human CD4 with2-F-pyrimidine-containing RNA amptamers for flow cytometry. Nucleic Acids Research. 1998; 26(17):3915-3924.
Edd, et al. Controlled encapsulation of single cells into monodisperse picoliter drops. Lap Chip. 2008; 8(8):1262-1264.
Giuggio, et al. Evolution of the intrahepatic T cell repertoire during chronic hepataitis C virus infection. Viral Immunol. 2005;18(1):179-89.
Jena, et al. Amplification of genes, single transcripts and cDNA libraries from one cell and direct sequence analysis of amplified products derived from one molecule. J. Immunol. Methods. 1996; 190:199-213.
Kim, et al an efficient and reliable DNA extraction method for preimplantation genetic diagnosis: a comparison of allele drop out and amplification rates using different single cell iysis methods. Fertility and Sterility. 2009; 92: 814-818.
Kobari, et al. T cells accumulating in the inflamed joints of a spontaneous murine model of rheumatoid arthritis become restricted to common clonotypes during disease progression. Int Immunol. Jan. 2004;16(1):131-8.
Li, et al. An improved one-tube RT-PCR protocol for analyzing single-cell gene expression in individual mammalian cells. Anal. Bioanal. Chem. 2010; 397: 1853-1859.
Novak, et al. Single-cell multiplex gene detection and sequencing With microfluidically generated agarose emulsions. Angewandte Chernie. 2011; 50: 390-395, with supplemental material.
Ray, et at. Single cell multiplex PCR amplification of five dystrophin gene exons combined with gender determination. Molecular Human Reproduction. 2001; 7(5): 489-494.
Tajiri, et al. Cell-microarray analysis of antigen-specific B-cells: single cell analysis of antigen receptor expression and specificity. Cytometry Part A. 2007; 71A: 961-967.
Thornhill, et al. A comparison of different lysis buffers to assess allele dropout from single cells for preimplantation genetic diagnosis. Prenatal Diagnosis. 2001; 21: 490-497.
Tokimitsu, et al. Single lymphocyte analysis with a microwell array chip. Cytometry. 2007; Part A, 71A: 1003-1010.
UK Search Report dated May 25, 2011 for UK application No. GB1009641.0.
Wells et al. Strategies for preimplantation genetic diagnosis of single gene disorders by DNA amplification. Prenatal Diagnosis. 1998; 18: 1389-1401.
Wetmur, et al. An emulsion polymerase chain reaction-based method for molecular Methods in Molecular Biology. 1996; 410: 351-361.
Wetmur, et al. Linking emulsion PCR haplotype analysis. chapter 11, in Park (editor), PCR Protocols, Methods En Molecular Biology. 2011; 687: 165-175.
Wetmur, et al. Molecular haplotyping by linking emulsion PCR: analysis of paraoxonase 1 haplotypes and phenotypes. Nucleic Acids Research. 2005; 33(8):2615-2619.
Yon, et al. Precise gene fusion by PCR. Nucleic Acids Research. 1989; 17(12):4895.
Zeng, et al. High-performance single cell genetic analysis using microfluidic emulsion generator arrays. Anal. Chem. 2010; 82:3183-3190.
U.S. Appl. No. 12/945,678, filed Nov. 12, 2010, Faham et al.
U.S. Appl. No. 13/627,497, filed Sep. 26, 2012, Faham et al.
U.S. Appl. No. 14/075,075, filed Nov. 8, 2013, Faham et al.
Office action dated Nov. 6, 2013 for U.S. Appl. No. 13/468,323.
Office action dated Nov. 27, 2013 for U.S. Appl. No. 13/196,885.

* cited by examiner

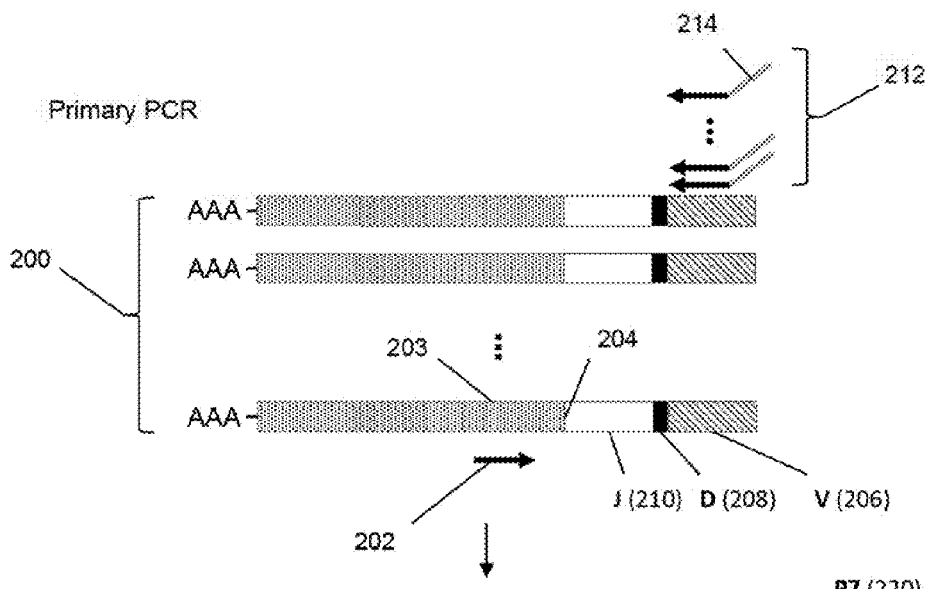
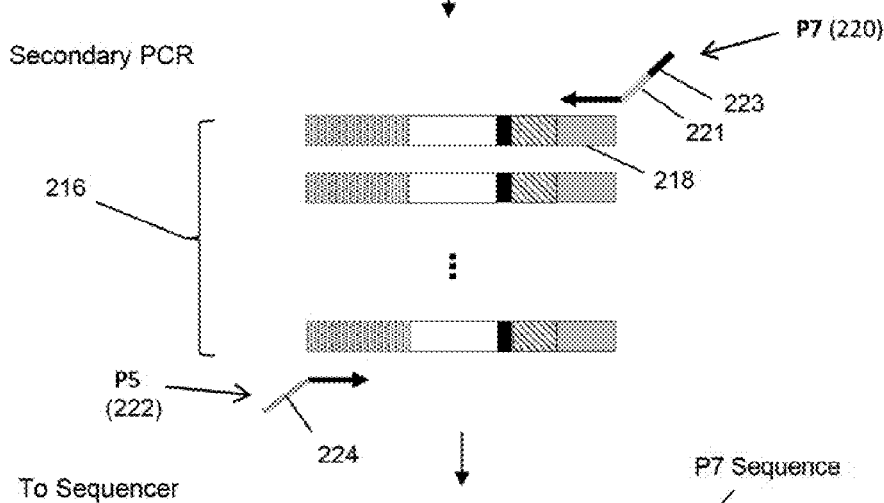
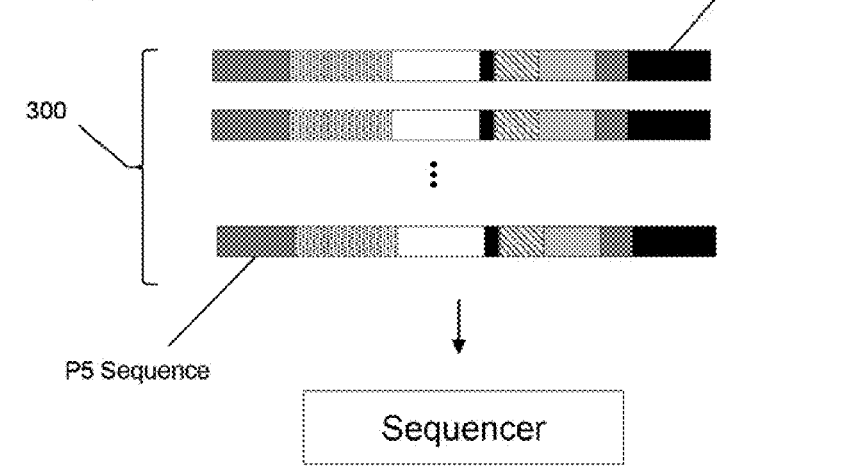

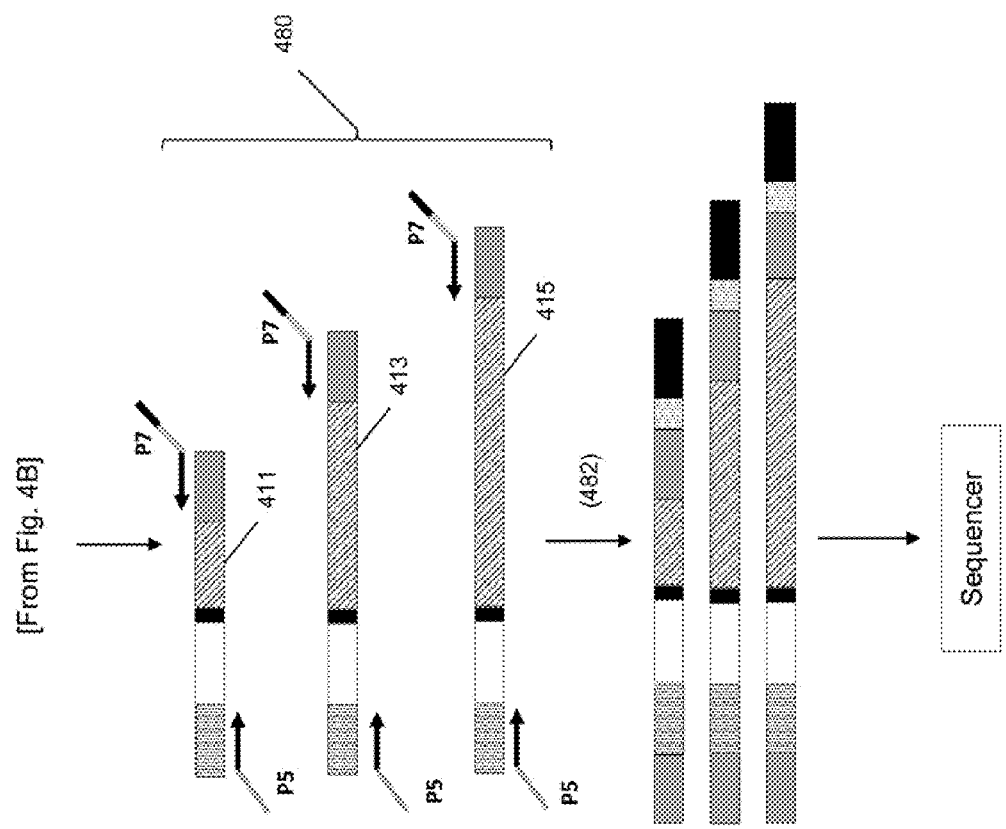

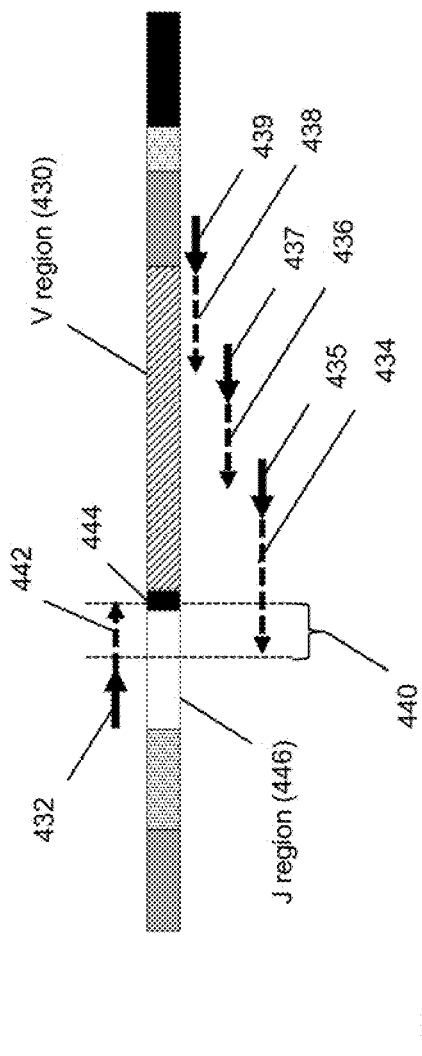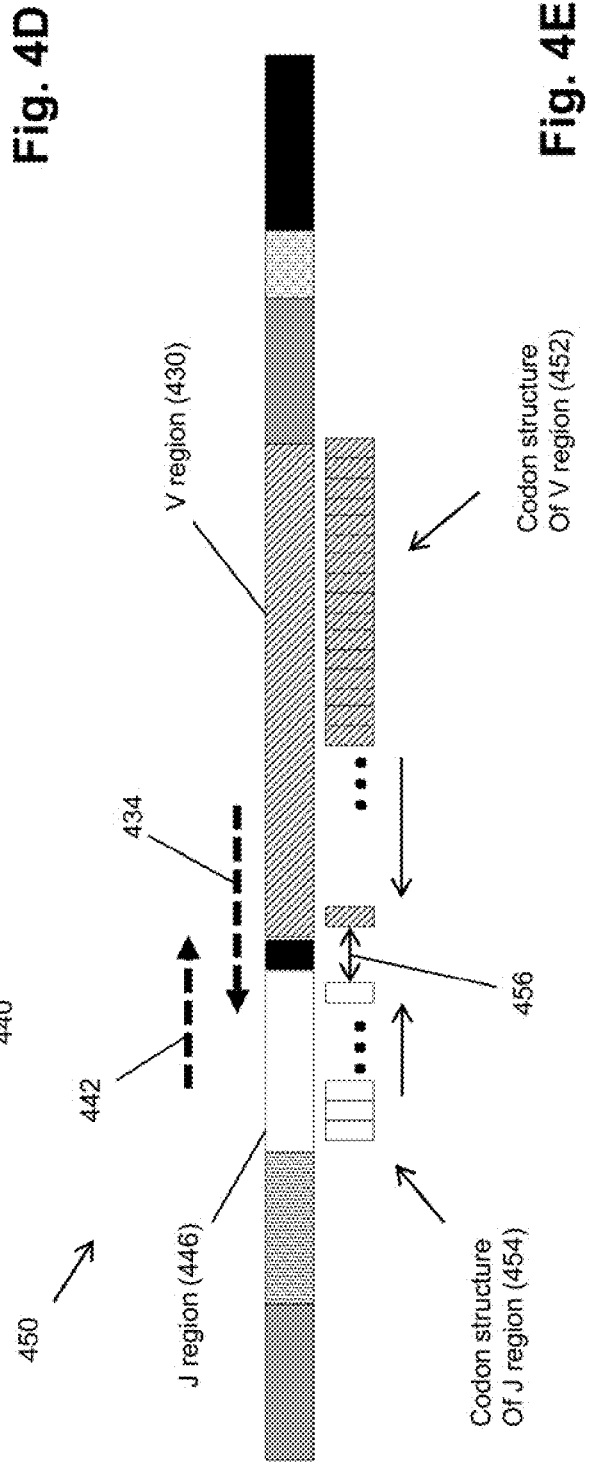

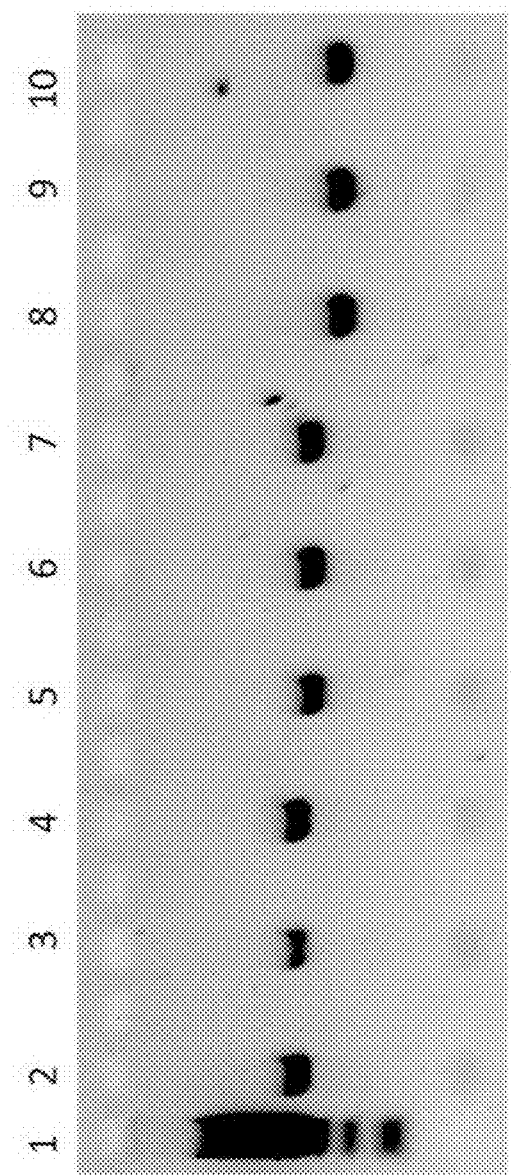

Amplification products after 2 stage PCRs with the 3 sets of V segment primers in stage 1 are shown. All use the J primers in the first stage. Lane 1 is the 100 bp size ladder (NEB), 2-4 amplification with primer set A, 5-7 with primer set B, and 8-10 with primer set C. The 3 different lanes for each primer set is for 3 different V segment primer concentrations. Since the second stage PCR primers are the same for all three pools, we have also shown that three products of the first stage PCR can be pooled to be amplified in the second stage PCR.

Fig. 8A

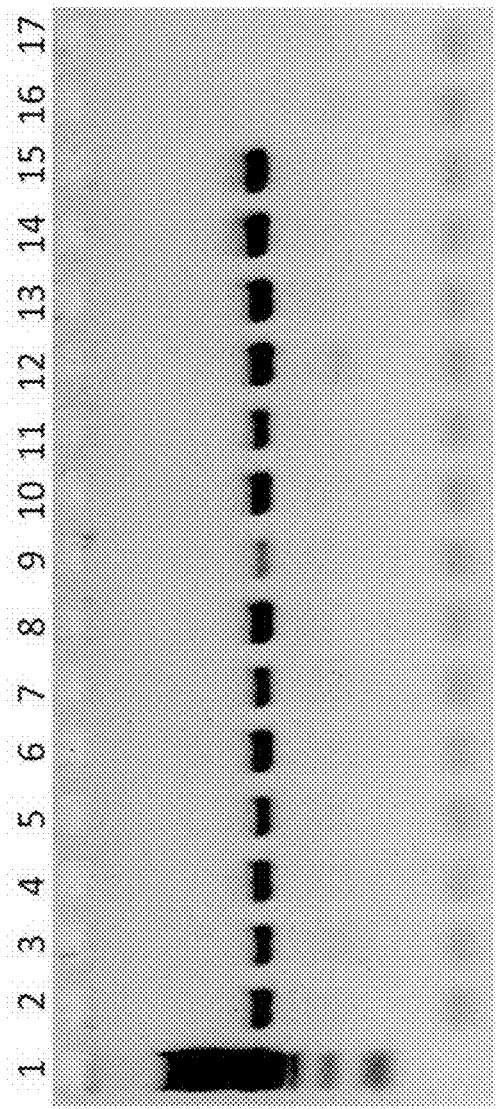

Amplification products after 2 stage PCRs with the J primers and the A set of V segment primers in stage 1 are shown. Lane 1 is the 100 bp size ladder (NEB), 2-9 use different amount of input blood genomic DNA (lane2-3: 250 ng, 4-5 and 10-11: 500 ng, 6-7: 1μg, and 8-9: 2.5 μg). Lanes 12-13 use 250 ng of spleen genomic DNA. Lanes 14-15 use 250 ng of the Raji B cell line (positive control), and lane 16-17 use 250 ng of Jurkat T cell line (negative control). The two reactions for each genomic DNA concentration use different primer concentrations.

Fig. 8B

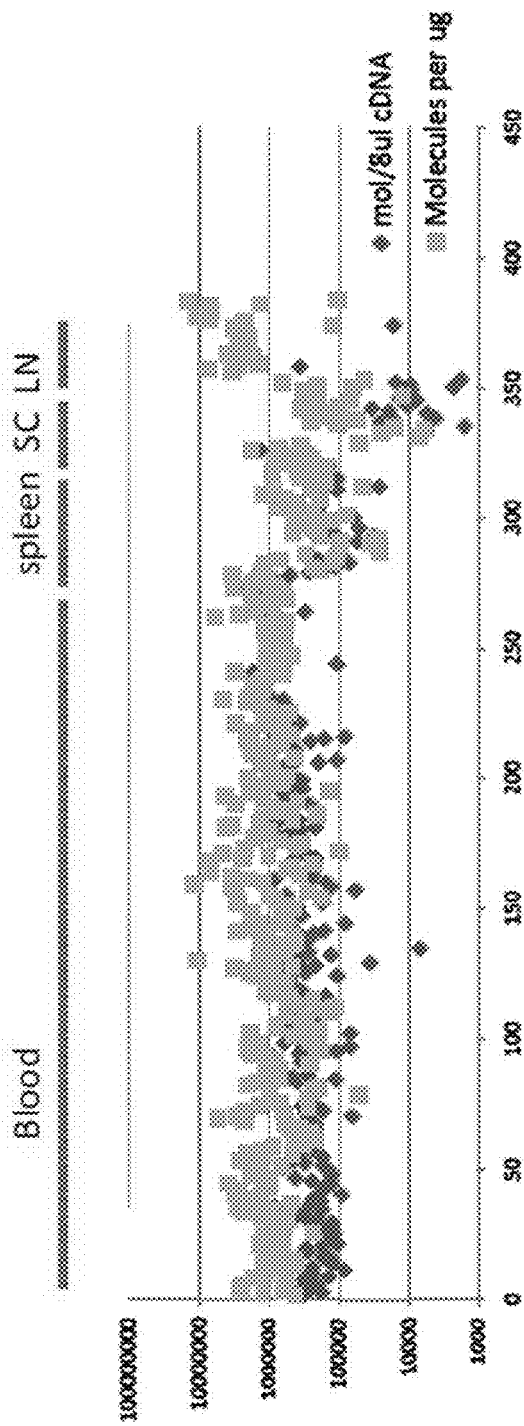

Fig. 9

Real time PCR using standards with known numbers of molecules were used to determine the number of TCRβ molecules in the input DNA. The dark colored dots depict the number of molecules that were ultimately amplified in the multiplex PCR, and the light colored dots show the number of molecules per μg RNA assuming a perfect 1:1 relationship between RNA and cDNA. (SC is spinal cord and LN is lymph node).

SEQUENCE LISTING

<160> NUMBER OF SEQ ID NOS: 144

<210> SEQ ID NO 1
<211> LENGTH: 20
<212> TYPE: DNA

<213> ORGANISM: Homo sapiens

<400> SEQUENCE: 1
agcgacctcg ggtgggaaca                              20

<210> SEQ ID NO 2
<211> LENGTH: 23
<212> TYPE: DNA
<213> ORGANISM: Homo sapiens

<400> SEQUENCE: 2
aactatgttt tggtatcgtc agt                          23

<210> SEQ ID NO 3
<211> LENGTH: 23
<212> TYPE: DNA
<213> ORGANISM: Homo sapiens

<400> SEQUENCE: 3
aactatgttt tggtatcgtc agt                          23

<210> SEQ ID NO 4
<211> LENGTH: 21
<212> TYPE: DNA
<213> ORGANISM: Homo sapiens

<400> SEQUENCE: 4
agtgtatcct ggtaccaaca g                            21

<210> SEQ ID NO 5
<211> LENGTH: 21
<212> TYPE: DNA
<213> ORGANISM: Homo sapiens

<400> SEQUENCE: 5
agtgtgtact ggtaccaaca g                            21

<210> SEQ ID NO 6
<211> LENGTH: 21
<212> TYPE: DNA
<213> ORGANISM: Homo sapiens

<400> SEQUENCE: 6
actgtgtcct ggtaccaaca g                            21

<210> SEQ ID NO 7
<211> LENGTH: 21
<212> TYPE: DNA
<213> ORGANISM: Homo sapiens

<400> SEQUENCE: 7
agtgtgtcct ggtaccaaca g                            21

<210> SEQ ID NO 8
<211> LENGTH: 21
<212> TYPE: DNA
<213> ORGANISM: Homo sapiens

<400> SEQUENCE: 8
tctgtgtact ggtaccaaca g                            21

<210> SEQ ID NO 9
<211> LENGTH: 20
<212> TYPE: DNA

```
<213> ORGANISM: Homo sapiens

<400> SEQUENCE: 9
ccctttactg gtaccgacag                                              20

<210> SEQ ID NO 10
<211> LENGTH: 20
<212> TYPE: DNA
<213> ORGANISM: Homo sapiens

<400> SEQUENCE: 10
gcctttactg gtaccgacag                                              20

<210> SEQ ID NO 11
<211> LENGTH: 21
<212> TYPE: DNA
<213> ORGANISM: Homo sapiens

<400> SEQUENCE: 11
ccctttactg gtaccgacaa a                                            21

<210> SEQ ID NO 12
<211> LENGTH: 19
<212> TYPE: DNA
<213> ORGANISM: Homo sapiens

<400> SEQUENCE: 12
ttttggtacc aacaggtcc                                               19

<210> SEQ ID NO 13
<211> LENGTH: 19
<212> TYPE: DNA
<213> ORGANISM: Homo sapiens

<400> SEQUENCE: 13
ttttggtacc aacaggccc                                               19

<210> SEQ ID NO 14
<211> LENGTH: 22
<212> TYPE: DNA
<213> ORGANISM: Homo sapiens

<400> SEQUENCE: 14
aaccctttat tggtatcaac ag                                           22

<210> SEQ ID NO 15
<211> LENGTH: 21
<212> TYPE: DNA
<213> ORGANISM: Homo sapiens

<400> SEQUENCE: 15
cgctatgtat tggtacaagc a                                            21

<210> SEQ ID NO 16
<211> LENGTH: 21
<212> TYPE: DNA
<213> ORGANISM: Homo sapiens

<400> SEQUENCE: 16
cgctatgtat tggtacaagc a                                            21

<210> SEQ ID NO 17
<211> LENGTH: 23
<212> TYPE: DNA
```

<213> ORGANISM: Homo sapiens

<400> SEQUENCE: 17
tttctggtac agacagacca tga                                    23

<210> SEQ ID NO 18
<211> LENGTH: 27
<212> TYPE: DNA
<213> ORGANISM: Homo sapiens

<400> SEQUENCE: 18
tactatgtat tggtataaac aggactc                                27

<210> SEQ ID NO 19
<211> LENGTH: 22
<212> TYPE: DNA
<213> ORGANISM: Homo sapiens

<400> SEQUENCE: 19
caaaatgtac tggtatcaac aa                                     22

<210> SEQ ID NO 20
<211> LENGTH: 22
<212> TYPE: DNA
<213> ORGANISM: Homo sapiens

<400> SEQUENCE: 20
caaaatgtac tggtatcaac aa                                     22

<210> SEQ ID NO 21
<211> LENGTH: 22
<212> TYPE: DNA
<213> ORGANISM: Homo sapiens

<400> SEQUENCE: 21
atgtactggt atcgacaaga cc                                     22

<210> SEQ ID NO 22
<211> LENGTH: 23
<212> TYPE: DNA
<213> ORGANISM: Homo sapiens

<400> SEQUENCE: 22
tgccatgtac tggtatagac aag                                    23

<210> SEQ ID NO 23
<211> LENGTH: 23
<212> TYPE: DNA
<213> ORGANISM: Homo sapiens

<400> SEQUENCE: 23
atacttgtcc tggtatcgac aag                                    23

<210> SEQ ID NO 24
<211> LENGTH: 22
<212> TYPE: DNA
<213> ORGANISM: Homo sapiens

<400> SEQUENCE: 24
atatgttctg gtatcgacaa ga                                     22

<210> SEQ ID NO 25
<211> LENGTH: 22
<212> TYPE: DNA

<213> ORGANISM: Homo sapiens

<400> SEQUENCE: 25
atatgtcctg gtatcgacaa ga					22

<210> SEQ ID NO 26
<211> LENGTH: 22
<212> TYPE: DNA
<213> ORGANISM: Homo sapiens

<400> SEQUENCE: 26
acatgtcctg gtatcgacaa ga					22

<210> SEQ ID NO 27
<211> LENGTH: 24
<212> TYPE: DNA
<213> ORGANISM: Homo sapiens

<400> SEQUENCE: 27
taatctttat tggtatcgac gtgt					24

<210> SEQ ID NO 28
<211> LENGTH: 20
<212> TYPE: DNA
<213> ORGANISM: Homo sapiens

<400> SEQUENCE: 28
gccatgtact ggtaccgaca					20

<210> SEQ ID NO 29
<211> LENGTH: 22
<212> TYPE: DNA
<213> ORGANISM: Homo sapiens

<400> SEQUENCE: 29
tcatgtttac tggtatcggc ag					22

<210> SEQ ID NO 30
<211> LENGTH: 21
<212> TYPE: DNA
<213> ORGANISM: Homo sapiens

<400> SEQUENCE: 30
caacctatac tggtaccgac a					21

<210> SEQ ID NO 31
<211> LENGTH: 22
<212> TYPE: DNA
<213> ORGANISM: Homo sapiens

<400> SEQUENCE: 31
catgctaccc tttactggta cc					22

<210> SEQ ID NO 32
<211> LENGTH: 22
<212> TYPE: DNA
<213> ORGANISM: Homo sapiens

<400> SEQUENCE: 32
cacaataccc tttactggta cc					22

<210> SEQ ID NO 33
<211> LENGTH: 26
<212> TYPE: DNA

```
<213> ORGANISM: Homo sapiens

<400> SEQUENCE: 33
atacttctat tggtacagac aaatct                                          26

<210> SEQ ID NO 34
<211> LENGTH: 21
<212> TYPE: DNA
<213> ORGANISM: Homo sapiens

<400> SEQUENCE: 34
cactgtctac tggtaccagc a                                               21

<210> SEQ ID NO 35
<211> LENGTH: 21
<212> TYPE: DNA
<213> ORGANISM: Homo sapiens

<400> SEQUENCE: 35
cgtcatgtac tggtaccagc a                                               21

<210> SEQ ID NO 36
<211> LENGTH: 21
<212> TYPE: DNA
<213> ORGANISM: unknown
<220> FEATURE:
<223> OTHER INFORMATION: primer

<400> SEQUENCE: 36
aatgatacgg cgaccaccga g                                               21

<210> SEQ ID NO 37
<211> LENGTH: 24
<212> TYPE: DNA
<213> ORGANISM: Unknown
<220> FEATURE:
<223> OTHER INFORMATION: primer

<400> SEQUENCE: 37
caagcagaag acggcatacg agat                                            24

<210> SEQ ID NO 38
<211> LENGTH: 34
<212> TYPE: DNA
<213> ORGANISM: Unknown
<220> FEATURE:
<223> OTHER INFORMATION: primer

<400> SEQUENCE: 38
agatcggaag agcacacgtc tgaactccag tcac                                 34

<210> SEQ ID NO 39
<211> LENGTH: 34
<212> TYPE: DNA
<213> ORGANISM: Unknown
<220> FEATURE:
<223> OTHER INFORMATION: primer

<400> SEQUENCE: 39
gtgactggag ttcagacgtg tgctcttccg atct                                 34

<210> SEQ ID NO 40
<211> LENGTH: 24
<212> TYPE: DNA
<213> ORGANISM: Homo sapiens
```

```
<400> SEQUENCE: 40
cctcagtgaa ggtctcctgc aagg                                          24

<210> SEQ ID NO 41
<211> LENGTH: 24
<212> TYPE: DNA
<213> ORGANISM: Homo sapiens

<400> SEQUENCE: 41
cctcggtgaa ggtctcctgc aagg                                          24

<210> SEQ ID NO 42
<211> LENGTH: 24
<212> TYPE: DNA
<213> ORGANISM: Homo sapiens

<400> SEQUENCE: 42
cctcagtgaa ggtttcctgc aagg                                          24

<210> SEQ ID NO 43
<211> LENGTH: 27
<212> TYPE: DNA
<213> ORGANISM: Homo sapiens

<400> SEQUENCE: 43
gggctacagt gaaaatctcc tgcaagg                                       27

<210> SEQ ID NO 44
<211> LENGTH: 26
<212> TYPE: DNA
<213> ORGANISM: Homo sapiens

<400> SEQUENCE: 44
aaacccacac agaccctcac gctgac                                        26

<210> SEQ ID NO 45
<211> LENGTH: 26
<212> TYPE: DNA
<213> ORGANISM: Homo sapiens

<400> SEQUENCE: 45
aaacccacag agaccctcac gctgac                                        26

<210> SEQ ID NO 46
<211> LENGTH: 26
<212> TYPE: DNA
<213> ORGANISM: Homo sapiens

<400> SEQUENCE: 46
aaacccacac agaccctcac actgac                                        26

<210> SEQ ID NO 47
<211> LENGTH: 25
<212> TYPE: DNA
<213> ORGANISM: Homo sapiens

<400> SEQUENCE: 47 ctgggggtc cctgagactc tcctg                                          25

<210> SEQ ID NO 48
<211> LENGTH: 25
<212> TYPE: DNA
<213> ORGANISM: Homo sapiens
```

```
<400> SEQUENCE: 48 ctgggggtc ccttagactc tcctg                                          25

<210> SEQ ID NO 49
<211> LENGTH: 25
<212> TYPE: DNA
<213> ORGANISM: Homo sapiens

<400> SEQUENCE: 49
cagggcggtc cctgagactc tcctg                                         25

<210> SEQ ID NO 50
<211> LENGTH: 25
<212> TYPE: DNA
<213> ORGANISM: Homo sapiens

<400> SEQUENCE: 50
cagggccgtc cctgagactc tcctg                                         25

<210> SEQ ID NO 51
<211> LENGTH: 25
<212> TYPE: DNA
<213> ORGANISM: Homo sapiens

<400> SEQUENCE: 51 ctgggggtc cctgaaactc tcctg                                          25

<210> SEQ ID NO 52
<211> LENGTH: 25
<212> TYPE: DNA
<213> ORGANISM: Homo sapiens

<400> SEQUENCE: 52
ctggcaggtc cctgagactc tcctg                                         25

<210> SEQ ID NO 53
<211> LENGTH: 25
<212> TYPE: DNA
<213> ORGANISM: Homo sapiens

<400> SEQUENCE: 53
ctggagggtc cctgagactc tcctg                                         25

<210> SEQ ID NO 54
<211> LENGTH: 25
<212> TYPE: DNA
<213> ORGANISM: Homo sapiens

<400> SEQUENCE: 54
ctgggaggtc cctgagactc tcctg                                         25

<210> SEQ ID NO 55
<211> LENGTH: 23
<212> TYPE: DNA
<213> ORGANISM: Homo sapiens

<400> SEQUENCE: 55 tggggggcc ctgagactct cct                                            23

<210> SEQ ID NO 56
<211> LENGTH: 25
<212> TYPE: DNA
<213> ORGANISM: Homo sapiens
```

```
<400> SEQUENCE: 56
cttcggagac cctgtccctc acctg                                          25

<210> SEQ ID NO 57
<211> LENGTH: 25
<212> TYPE: DNA
<213> ORGANISM: Homo sapiens

<400> SEQUENCE: 57
cttcggacac cctgtccctc acctg                                          25

<210> SEQ ID NO 58
<211> LENGTH: 25
<212> TYPE: DNA
<213> ORGANISM: Homo sapiens

<400> SEQUENCE: 58
cttcacagac cctgtccctc acctg                                          25

<210> SEQ ID NO 59
<211> LENGTH: 25
<212> TYPE: DNA
<213> ORGANISM: Homo sapiens

<400> SEQUENCE: 59
cttcggagac cccgtccctc acctg                                          25

<210> SEQ ID NO 60
<211> LENGTH: 22
<212> TYPE: DNA
<213> ORGANISM: Homo sapiens

<400> SEQUENCE: 60
cggggaccct gtccctcacc tg                                             22

<210> SEQ ID NO 61
<211> LENGTH: 29
<212> TYPE: DNA
<213> ORGANISM: Homo sapiens

<400> SEQUENCE: 61
gatctcctgt aagggttctg gatacagct                                      29

<210> SEQ ID NO 62
<211> LENGTH: 25
<212> TYPE: DNA
<213> ORGANISM: Homo sapiens

<400> SEQUENCE: 62
tcgcagaccc tctcactcac ctgtg                                          25

<210> SEQ ID NO 63
<211> LENGTH: 25
<212> TYPE: DNA
<213> ORGANISM: Homo sapiens

<400> SEQUENCE: 63
tggatcaggc agtccccatc gagag                                          25

<210> SEQ ID NO 64
<211> LENGTH: 20
<212> TYPE: DNA
<213> ORGANISM: Homo sapiens
```

-continued

```
<400> SEQUENCE: 64
gctgggtgcg ccagatgccc                                                    20

<210> SEQ ID NO 65
<211> LENGTH: 20
<212> TYPE: DNA
<213> ORGANISM: Homo sapiens

<400> SEQUENCE: 65
tggatccgtc agcccccagg                                                    20

<210> SEQ ID NO 66
<211> LENGTH: 20
<212> TYPE: DNA
<213> ORGANISM: Homo sapiens

<400> SEQUENCE: 66
tggatccgtc agcccccggg                                                    20

<210> SEQ ID NO 67
<211> LENGTH: 21
<212> TYPE: DNA
<213> ORGANISM: Homo sapiens

<400> SEQUENCE: 67
gtgcgacagg cccctggaca a                                                  21

<210> SEQ ID NO 68
<211> LENGTH: 23
<212> TYPE: DNA
<213> ORGANISM: Homo sapiens

<400> SEQUENCE: 68
gggtgcgaca ggccactgga caa                                                23

<210> SEQ ID NO 69
<211> LENGTH: 21
<212> TYPE: DNA
<213> ORGANISM: Homo sapiens

<400> SEQUENCE: 69
gtgcgccagg cccccggaca a                                                  21

<210> SEQ ID NO 70
<211> LENGTH: 23
<212> TYPE: DNA
<213> ORGANISM: Homo sapiens

<400> SEQUENCE: 70
gggtgcgaca ggctcgtgga caa                                                23

<210> SEQ ID NO 71
<211> LENGTH: 23
<212> TYPE: DNA
<213> ORGANISM: Homo sapiens

<400> SEQUENCE: 71
gggtgcaaca ggcccctgga aaa                                                23

<210> SEQ ID NO 72
<211> LENGTH: 23
<212> TYPE: DNA
<213> ORGANISM: Homo sapiens
```

```
<400> SEQUENCE: 72
gggtgcgaca ggctcctgga aaa                                          23

<210> SEQ ID NO 73
<211> LENGTH: 21
<212> TYPE: DNA
<213> ORGANISM: Homo sapiens

<400> SEQUENCE: 73
gtgcgacagg cccccggaca a                                            21

<210> SEQ ID NO 74
<211> LENGTH: 21
<212> TYPE: DNA
<213> ORGANISM: Homo sapiens

<400> SEQUENCE: 74
gtgcgacagg cccccagaca a                                            21

<210> SEQ ID NO 75
<211> LENGTH: 21
<212> TYPE: DNA
<213> ORGANISM: Homo sapiens

<400> SEQUENCE: 75
tccgccagcc cccagggaag g                                            21

<210> SEQ ID NO 76
<211> LENGTH: 21
<212> TYPE: DNA
<213> ORGANISM: Homo sapiens

<400> SEQUENCE: 76
tccggcagcc cccagggaag g                                            21

<210> SEQ ID NO 77
<211> LENGTH: 21
<212> TYPE: DNA
<213> ORGANISM: Homo sapiens

<400> SEQUENCE: 77
tccggcagcc accagggaag g                                            21

<210> SEQ ID NO 78
<211> LENGTH: 21
<212> TYPE: DNA
<213> ORGANISM: Homo sapiens

<400> SEQUENCE: 78
tccgccagca cccagggaag g                                            21

<210> SEQ ID NO 79
<211> LENGTH: 19
<212> TYPE: DNA
<213> ORGANISM: Homo sapiens

<400> SEQUENCE: 79
tccggcagcc cgccgggaa                                               19

<210> SEQ ID NO 80
<211> LENGTH: 19
<212> TYPE: DNA
<213> ORGANISM: Homo sapiens
```

<400> SEQUENCE: 80
tccggcagcc gccggggaa                                          19

<210> SEQ ID NO 81
<211> LENGTH: 21
<212> TYPE: DNA
<213> ORGANISM: Homo sapiens

<400> SEQUENCE: 81
tccggcagcc cgctgggaag g                                       21

<210> SEQ ID NO 82
<211> LENGTH: 21
<212> TYPE: DNA
<213> ORGANISM: Homo sapiens

<400> SEQUENCE: 82
tccgccagcc cctagggaag g                                       21

<210> SEQ ID NO 83
<211> LENGTH: 21
<212> TYPE: DNA
<213> ORGANISM: Homo sapiens

<400> SEQUENCE: 83
ggtccgccag gctccaggga a                                       21

<210> SEQ ID NO 84
<211> LENGTH: 21
<212> TYPE: DNA
<213> ORGANISM: Homo sapiens

<400> SEQUENCE: 84
gttccgccag gctccaggga a                                       21

<210> SEQ ID NO 85
<211> LENGTH: 21
<212> TYPE: DNA
<213> ORGANISM: Homo sapiens

<400> SEQUENCE: 85
ggtccgccag gcttccggga a                                       21

<210> SEQ ID NO 86
<211> LENGTH: 21
<212> TYPE: DNA
<213> ORGANISM: Homo sapiens

<400> SEQUENCE: 86
ggtccgtcaa gctccgggga a                                       21

<210> SEQ ID NO 87
<211> LENGTH: 21
<212> TYPE: DNA
<213> ORGANISM: Homo sapiens

<400> SEQUENCE: 87
gatccgccag gctccaggga a                                       21

<210> SEQ ID NO 88
<211> LENGTH: 21
<212> TYPE: DNA
<213> ORGANISM: Homo sapiens

```
<400> SEQUENCE: 88
ggtccgccaa gctccaggga a                                              21

<210> SEQ ID NO 89
<211> LENGTH: 21
<212> TYPE: DNA
<213> ORGANISM: Homo sapiens

<400> SEQUENCE: 89
ggtccgccag gctccaggca a                                              21

<210> SEQ ID NO 90
<211> LENGTH: 21
<212> TYPE: DNA
<213> ORGANISM: Homo sapiens

<400> SEQUENCE: 90
ggtccgccag gctccaggca a                                              21

<210> SEQ ID NO 91
<211> LENGTH: 21
<212> TYPE: DNA
<213> ORGANISM: Homo sapiens

<400> SEQUENCE: 91
ggtccgccag gctccgggca a                                              21

<210> SEQ ID NO 92
<211> LENGTH: 24
<212> TYPE: DNA
<213> ORGANISM: Homo sapiens

<400> SEQUENCE: 92
gggtccgtca agctccaggg aagg                                           24

<210> SEQ ID NO 93
<211> LENGTH: 24
<212> TYPE: DNA
<213> ORGANISM: Homo sapiens

<400> SEQUENCE: 93
ctgggtccgc caagctacag gaaa                                           24

<210> SEQ ID NO 94
<211> LENGTH: 21
<212> TYPE: DNA
<213> ORGANISM: Homo sapiens

<400> SEQUENCE: 94
ggtccgccag cctccaggga a                                              21

<210> SEQ ID NO 95
<211> LENGTH: 21
<212> TYPE: DNA
<213> ORGANISM: Homo sapiens

<400> SEQUENCE: 95
ggtccggcaa gctccaggga a                                              21

<210> SEQ ID NO 96
<211> LENGTH: 25
<212> TYPE: DNA
<213> ORGANISM: Homo sapiens
```

```
<400> SEQUENCE: 96
ctaaaggctg aggacactgc cgtgt                                              25

<210> SEQ ID NO 97
<211> LENGTH: 25
<212> TYPE: DNA
<213> ORGANISM: Homo sapiens

<400> SEQUENCE: 97
ctctgtgact cccgaggaca cggct                                              25

<210> SEQ ID NO 98
<211> LENGTH: 22
<212> TYPE: DNA
<213> ORGANISM: Homo sapiens

<400> SEQUENCE: 98
agtggagcag cctgaaggcc tc                                                 22

<210> SEQ ID NO 99
<211> LENGTH: 25
<212> TYPE: DNA
<213> ORGANISM: Homo sapiens

<400> SEQUENCE: 99
tgaccaacat ggaccctgtg gacac                                              25

<210> SEQ ID NO 100
<211> LENGTH: 25
<212> TYPE: DNA
<213> ORGANISM: Homo sapiens

<400> SEQUENCE: 100
acatggagct gagcagcctg agatc                                              25

<210> SEQ ID NO 101
<211> LENGTH: 25
<212> TYPE: DNA
<213> ORGANISM: Homo sapiens

<400> SEQUENCE: 101
acatggagct gagcaggctg agatc                                              25

<210> SEQ ID NO 102
<211> LENGTH: 25
<212> TYPE: DNA
<213> ORGANISM: Homo sapiens

<400> SEQUENCE: 102
acatggagct gaggagcctg agatc                                              25

<210> SEQ ID NO 103
<211> LENGTH: 28
<212> TYPE: DNA
<213> ORGANISM: Homo sapiens

<400> SEQUENCE: 103
acatggagct gaggagccta agatctga                                           28

<210> SEQ ID NO 104
<211> LENGTH: 22
<212> TYPE: DNA
<213> ORGANISM: Homo sapiens
```

-continued

```
<400> SEQUENCE: 104
gagctctgtg accgccgcgg ac                                    22

<210> SEQ ID NO 105
<211> LENGTH: 23
<212> TYPE: DNA
<213> ORGANISM: Homo sapiens

<400> SEQUENCE: 105
gagctctgtg accgccgtgg aca                                   23

<210> SEQ ID NO 106
<211> LENGTH: 25
<212> TYPE: DNA
<213> ORGANISM: Homo sapiens

<400> SEQUENCE: 106
gagctctgtg accgctgcag acacg                                 25

<210> SEQ ID NO 107
<211> LENGTH: 23
<212> TYPE: DNA
<213> ORGANISM: Homo sapiens

<400> SEQUENCE: 107
gagctctgtg accgctgcgg aca                                   23

<210> SEQ ID NO 108
<211> LENGTH: 25
<212> TYPE: DNA
<213> ORGANISM: Homo sapiens

<400> SEQUENCE: 108
gagctctgtg actgccgcag acacg                                 25

<210> SEQ ID NO 109
<211> LENGTH: 25
<212> TYPE: DNA
<213> ORGANISM: Homo sapiens

<400> SEQUENCE: 109
gagctctgtg actgcagcag acacg                                 25

<210> SEQ ID NO 110
<211> LENGTH: 23
<212> TYPE: DNA
<213> ORGANISM: Homo sapiens

<400> SEQUENCE: 110
gagctctgtg actgccgcgg aca                                   23

<210> SEQ ID NO 111
<211> LENGTH: 22
<212> TYPE: DNA
<213> ORGANISM: Homo sapiens

<400> SEQUENCE: 111
gagctctgtg accgcggacg cg                                    22

<210> SEQ ID NO 112
<211> LENGTH: 21
<212> TYPE: DNA
<213> ORGANISM: Homo sapiens
```

<400> SEQUENCE: 112
ggctctgtga ccgccgcgga c                                         21

<210> SEQ ID NO 113
<211> LENGTH: 23
<212> TYPE: DNA
<213> ORGANISM: Homo sapiens

<400> SEQUENCE: 113
gagctctgtg accgccgcag aca                                       23

<210> SEQ ID NO 114
<211> LENGTH: 23
<212> TYPE: DNA
<213> ORGANISM: Homo sapiens

<400> SEQUENCE: 114
gagctctgtg accgctgaca cgg                                       23

<210> SEQ ID NO 115
<211> LENGTH: 28
<212> TYPE: DNA
<213> ORGANISM: Homo sapiens

<400> SEQUENCE: 115
caaatgaaca gcctgagagc cgaggaca                                  28

<210> SEQ ID NO 116
<211> LENGTH: 28
<212> TYPE: DNA
<213> ORGANISM: Homo sapiens

<400> SEQUENCE: 116
caaatgaaca gcctgaaaac cgaggaca                                  28

<210> SEQ ID NO 117
<211> LENGTH: 28
<212> TYPE: DNA
<213> ORGANISM: Homo sapiens

<400> SEQUENCE: 117
caaatgaaca gtctgaaaac cgaggaca                                  28

<210> SEQ ID NO 118
<211> LENGTH: 28
<212> TYPE: DNA
<213> ORGANISM: Homo sapiens

<400> SEQUENCE: 118
caaatgatca gcctgaaaac cgaggaca                                  28

<210> SEQ ID NO 119
<211> LENGTH: 30
<212> TYPE: DNA
<213> ORGANISM: Homo sapiens

<400> SEQUENCE: 119
caaatgaaca gtctgagaac tgaggacacc                                30

<210> SEQ ID NO 120
<211> LENGTH: 28
<212> TYPE: DNA
<213> ORGANISM: Homo sapiens

<400> SEQUENCE: 120
caaatgaaca gtctgagagc cgaggaca          28

<210> SEQ ID NO 121
<211> LENGTH: 28
<212> TYPE: DNA
<213> ORGANISM: Homo sapiens

<400> SEQUENCE: 121
caaatgaaca gcctgagagc tgaggaca          28

<210> SEQ ID NO 122
<211> LENGTH: 28
<212> TYPE: DNA
<213> ORGANISM: Homo sapiens

<400> SEQUENCE: 122
caaatgagca gcctgagagc tgaggaca          28

<210> SEQ ID NO 123
<211> LENGTH: 28
<212> TYPE: DNA
<213> ORGANISM: Homo sapiens

<400> SEQUENCE: 123
caaatgaaca gcctgagaga cgaggaca          28

<210> SEQ ID NO 124
<211> LENGTH: 28
<212> TYPE: DNA
<213> ORGANISM: Homo sapiens

<400> SEQUENCE: 124
caaatgggca gcctgagagc tgaggaca          28

<210> SEQ ID NO 125
<211> LENGTH: 26
<212> TYPE: DNA
<213> ORGANISM: Homo sapiens

<400> SEQUENCE: 125
caaatgaaca gcctgagagc cggga          26

<210> SEQ ID NO 126
<211> LENGTH: 28
<212> TYPE: DNA
<213> ORGANISM: Homo sapiens

<400> SEQUENCE: 126
caaatgaaca gtctgagagc tgaggaca          28

<210> SEQ ID NO 127
<211> LENGTH: 28
<212> TYPE: DNA
<213> ORGANISM: Homo sapiens

<400> SEQUENCE: 127
caaatgagca gtctgagagc tgaggaca          28

<210> SEQ ID NO 128
<211> LENGTH: 20
<212> TYPE: DNA
<213> ORGANISM: Homo sapiens

```
<400> SEQUENCE: 128
gccaggggga agaccgatgg                                                  20

<210> SEQ ID NO 129
<211> LENGTH: 20
<212> TYPE: DNA
<213> ORGANISM: Homo sapiens

<400> SEQUENCE: 129
gccaggggga agacggatgg                                                  20

<210> SEQ ID NO 130
<211> LENGTH: 50
<212> TYPE: DNA
<213> ORGANISM: Homo sapiens

<400> SEQUENCE: 130
aatgatacgg cgaccaccga gatctgggaa gacgatgggc ccttggtgga                 50

<210> SEQ ID NO 131
<211> LENGTH: 22
<212> TYPE: DNA
<213> ORGANISM: Homo sapiens

<400> SEQUENCE: 131
gtgtgagctg gatccgtcag cc                                               22

<210> SEQ ID NO 132
<211> LENGTH: 22
<212> TYPE: DNA
<213> ORGANISM: Homo sapiens

<400> SEQUENCE: 132
gtgtgggctg gatccgtcag cc                                               22

<210> SEQ ID NO 133
<211> LENGTH: 22
<212> TYPE: DNA
<213> ORGANISM: Homo sapiens

<400> SEQUENCE: 133
gtgcgagctg gatccgtcag cc                                               22

<210> SEQ ID NO 134
<211> LENGTH: 24
<212> TYPE: DNA
<213> ORGANISM: Homo sapiens

<400> SEQUENCE: 134
gcagcctaaa ggctgaggac actg                                             24

<210> SEQ ID NO 135
<211> LENGTH: 24
<212> TYPE: DNA
<213> ORGANISM: Homo sapiens

<400> SEQUENCE: 135
gcacgctaaa ggctgaggac actg                                             24

<210> SEQ ID NO 136
<211> LENGTH: 41
<212> TYPE: DNA
<213> ORGANISM: Homo sapiens
<220> FEATURE:
```

```
<221> NAME/KEY: misc_feature
<222> LOCATION: (19)..(19)
<223> OTHER INFORMATION: n is a, c, g, or t

<400> SEQUENCE: 136
acgagcctca tgcgtaganc tcacctgagg agacggtgac c        41

<210> SEQ ID NO 137
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 137
acgagcctca tgcgtaganc tcacctgagg agacagtgac c        41

<210> SEQ ID NO 138
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 138
acgagcctca tgcgtaganc ttacctgaag agacggtgac c        41

<210> SEQ ID NO 139
<211> LENGTH: 41
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t

<400> SEQUENCE: 139
acgagcctca tgcgtaganc ttacctgagg agacggtgac c        41

<210> SEQ ID NO 140
<211> LENGTH: 25
<212> TYPE: DNA
<213> ORGANISM: Homo sapiens

<400> SEQUENCE: 140
aatgatacgg cgaccaccga gatct                          25

<210> SEQ ID NO 141
<211> LENGTH: 64
<212> TYPE: DNA
<213> ORGANISM: Unknown
<220> FEATURE:
<223> OTHER INFORMATION: primer
<220> FEATURE:
<221> NAME/KEY: misc_feature
<222> LOCATION: (25)..(30)
<223> OTHER INFORMATION: n is a, c, g, or t

<400> SEQUENCE: 141
caagcagaag acggcatacg agatnnnnnn gtgactggag ttcagacgtg tgctcttccg   60
atct                                                 64

<210> SEQ ID NO 142
```

```
<211> LENGTH: 23
<212> TYPE: DNA
<213> ORGANISM: mouse

<400> SEQUENCE: 142
tgatggctca aacaaggaga cct                                           23

<210> SEQ ID NO 143
<211> LENGTH: 57
<212> TYPE: DNA
<213> ORGANISM: mouse

<400> SEQUENCE: 143
aatgatacgg cgaccaccga gatctgacct tgggtggagt cacatttctc agatcct      57

<210> SEQ ID NO 144
<211> LENGTH: 58
<212> TYPE: DNA
<213> ORGANISM: Homo sapiens

<400> SEQUENCE: 144
aatgatacgg cgaccaccga gatctacact ctttccctac acgagcctca tgcgtaga     58
```

SEQUENCE ANALYSIS OF COMPLEX AMPLICONS

This application is a continuation-in-part of U.S. patent application Ser. No. 12/615,263 filed on 9 Nov. 2009, now U.S. Pat. No. 8,236,503 which claims the benefit of U.S. provisional application Ser. No. 61/112,693 filed on 7 Nov. 2008. This application also claims the benefit of U.S. provisional application Ser. Nos. 61/455,743 filed on 25 Oct. 2010; 61/446,822 filed on 25 Feb. 2011; and 61/332,175 filed on 6 May 2010. Each of the foregoing patent applications are hereby incorporated by reference in their entireties.

TECHNICAL FIELD

The invention relates generally to methods for characterizing complex populations of nucleic acid sequences, such as amplicons, and more particularly, to methods for constructing profiles of immune system molecules using high throughput DNA sequencing.

BACKGROUND OF THE INVENTION

Analysis of biological or medical samples often requires the determination of nucleic acid sequences of large and complex populations of DNA and/or RNA, e.g. Gloor et al, PLoS ONE 5(10): e15406 (2010); Petrosino et al, Clinical Chemistry, 55(5): 856-866 (2009); Arstila et al, Science, 286: 958-961 (1999). In particular, profiles of nucleic acids encoding immune molecules, such as T cell or B cell receptors, or their components, contain a wealth of information on the state of health or disease of an organism, so that the use of such profiles as diagnostic or prognostic indicators has been proposed for a wide variety of conditions, e.g. Faham and Willis, U.S. patent publication 2010/0151471; Freeman et al, Genome Research, 19: 1817-1824 (2009); Boyd et al, Sci. Transl. Med., 1(12): 12ra23 (2009): He et al, Oncotarget (Mar. 8, 2011). Such sequence-based profiles provide much greater sensitivity than approaches based on size distributions of amplified target nucleic acids, sequence sampling by microarrays, hybridization kinetics curves from PCR amplicons, or the like, e.g. Morley et al, U.S. Pat. No. 5,418,134; van Dongen et al, Leukemia, 17: 2257-2317 (2003); Ogle et al, Nucleic Acids Research, 31: e139 (2003); Wang et al, BMC Genomics, 8: 329 (2007); Baum et al, Nature Methods, 3(11): 895-901 (2006). However, because of the size and diversity of such nucleic acid populations, constructing useful profiles by sequence analysis poses significant challenges even for next-generation sequencing platforms, e.g. Warren et al, Bioinformatics, 25: 458-464 (2009); Warren et al, Genome Research (Epub 24 Feb. 2011); Garcia-Castillo et al, Cardiovascular & Haematological Disorders-Drug Targets, 9: 124-135 (2009).

Such challenges include uniform amplification of target populations so that nucleic acid quality of sequence reads; and selection of the number, composition and positioning of sequencing primers, in view of unknown target sequence variability, for example, caused by somatic hypermutation, clonal evolution, or like phenomena, e.g. Li et al, Blood, 102(13): 4520-4526 (2003); Tichopad et al, Clin. Chem., 55: 1816-1823 (2009); Brockman et al, Genome Research. 18: 763-770 (2008).

It would be very useful and advantageous for many fields in medicine and biology, if methods were available for overcoming drawbacks of current methodologies for analyzing complex populations of nucleic acids, particularly with respect to high-throughput sequencing platforms having limited sequence read lengths or significantly declining sequence quality as a function of read length.

SUMMARY OF THE INVENTION

The present invention is drawn to methods for producing sequence-based profiles of complex nucleic acid populations. The invention is exemplified in a number of implementations and applications, some of which are summarized below and throughout the specification.

In one aspect the invention is directed to a method for determining a clonotype profile of T cell receptors and/or B cell receptors of an individual comprising the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated; (c) sequencing said spatially isolated individual molecules; and (d) determining abundances of different sequences of the nucleic acid molecules from the nucleic acid sample to generate the clonotype profile.

In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules, complete IgK molecules, IgK inactive molecules, TCRβ molecules, TCRγ molecules, complete TCRδ molecules, and incomplete TCRδ molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100. In another embodiment, the step of sequencing spatially isolated individual molecules comprises disposing such molecules on a solid surface where they are sequenced. Further to the latter embodiment, the step of disposing includes amplifying such molecules on the solid surface by bridge PCR. Still further to the latter embodiment, the step of sequencing such molecules is carried out by a sequencing-by-synthesis technique.

In another aspect, the invention provides a method for characterizing a clonotype comprising a V(D)J region or a portion thereof comprising the following steps: (a) generating at least one J region sequence read that begins in a J region and extends through an NDN region to a V region and at least one V region sequence read that begins in the V region and extends through the NDN region to the J region, the J region sequence read and the V region sequence read overlapping, and the J region and the V region each having a codon structure: and (b) determining whether the codon structure of the J region extended into the NDN region is in frame with the codon structure of the V region extended into the NDN region.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the invention.

BRIEF DESCRIPTION OF THE DRAWINGS

The novel features of the invention are set forth with particularity in the appended claims. A better understanding of the features and advantages of the present invention is obtained by reference to the following detailed description that sets forth illustrative embodiments, in which the principles of the invention are utilized, and the accompanying drawings of which:

FIGS. 2A-2B show a two-staged PCR scheme for amplifying TCRβ genes.

FIG. 3A illustrates a PCR product to be sequenced that was amplified using the scheme of FIGS. 2A-2B.

FIGS. 4B-4C illustrates a PCR scheme for generating three sequencing templates from an IgH chain in three separate reactions after which the resulting amplicons are combined for a secondary PCR to add P5 and P7 primer binding sites. FIG. 4D illustrates the locations of sequence reads generated for an IgH chain. FIG. 4E illustrates the use of the codon structure of V and J regions to improve base calls in the NDN region.

FIG. 8 the number of TCRβ molecules from samples. 8A and 8B show data from IgH amplification from genomic DNA FIG. 9 shows data indicating that multiplex amplifications in accordance with the invention have minimal amplification bias.

DETAILED DESCRIPTION OF THE INVENTION

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual; and Molecular Cloning: A Laboratory Manual* (all from Cold Spring Harbor Laboratory Press); and the like.

Figure 1A:
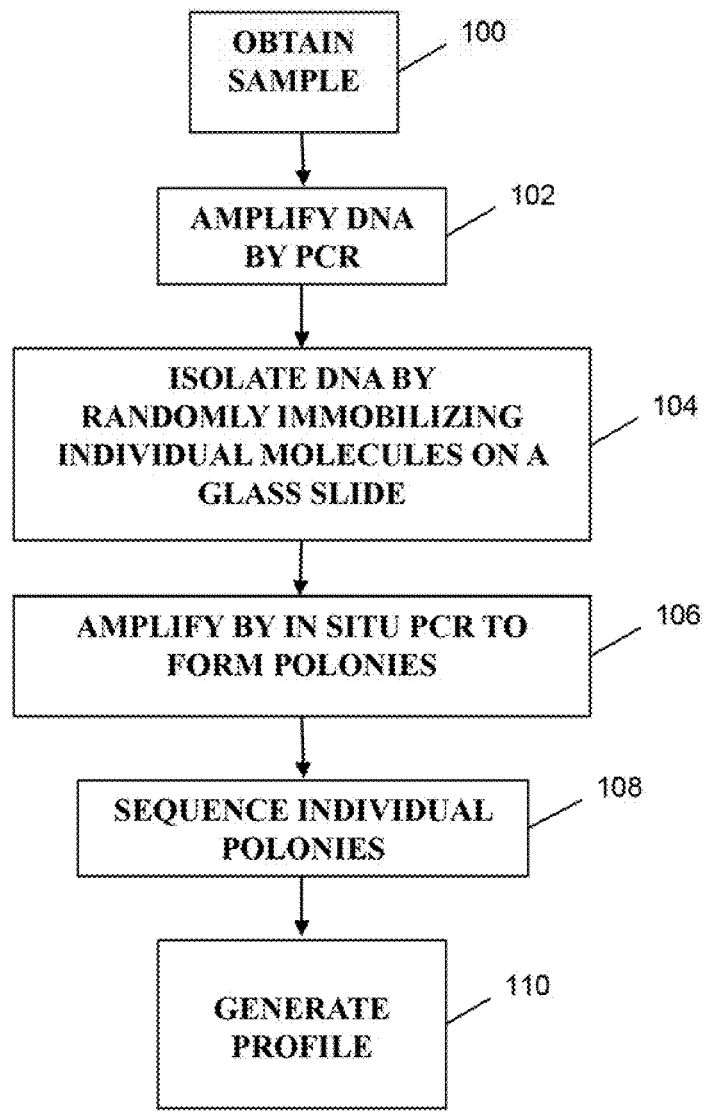
FIG. 1A is a flow diagram of an embodiment of a method of the provided invention for determining clonotype profiles.

One aspect, the invention utilizes next generation sequencing technologies to generate sequence profiles of complex nucleic acid populations, which, in turn, permit sequence-based identification of biological phenomena, such as organisms, disease conditions, histories of infection, and the like. Exemplary nucleic acid populations amenable to such analysis include amplicons of 16S rDNA of microbial communities, TCR or BCR rearrangements in a population of lymphocytes, and the like. In one aspect, multiplex amplification to amplify all the different types of sequences of a specific portion of gene or transcript can be accomplished from a sample, such as from blood or bone marrow DNA, for measuring clonotype profiles. For example, to amplify IgH sequences, several primers complementary to all the known V segments and alleles can be used along with several primers complementary to all the J segments and alleles. FIG. 1A illustrates steps of such a method for an embodiment employing one class of DNA sequencers for profiling clonotypes of a sample of a TCR or BCR repertoire. A sample containing B cells or T cells is obtained (100) after which DNA or RNA is extracted and amplified (102) in a reaction that preferentially amplifies clonotypes and attaches terminal sequences for subsequent amplification and sequencing. Individual molecules of the amplified clonotypes are randomly distributed on a solid surface (104), such as, a glass surface, which has been configured to permit a second in situ amplification to produce clonal populations (or polonies or clusters) of each individual molecule (106). The molecules of each cluster are then sequenced (108), for example, using a sequencing-by-synthesis technique, after which the types and abundances of the sequences are tabulated to form a profile (110), such as a clonotype profile, or equivalently a repertoire profile. The method can be performed with little amplification bias among the different sequences.

Figure 1B:
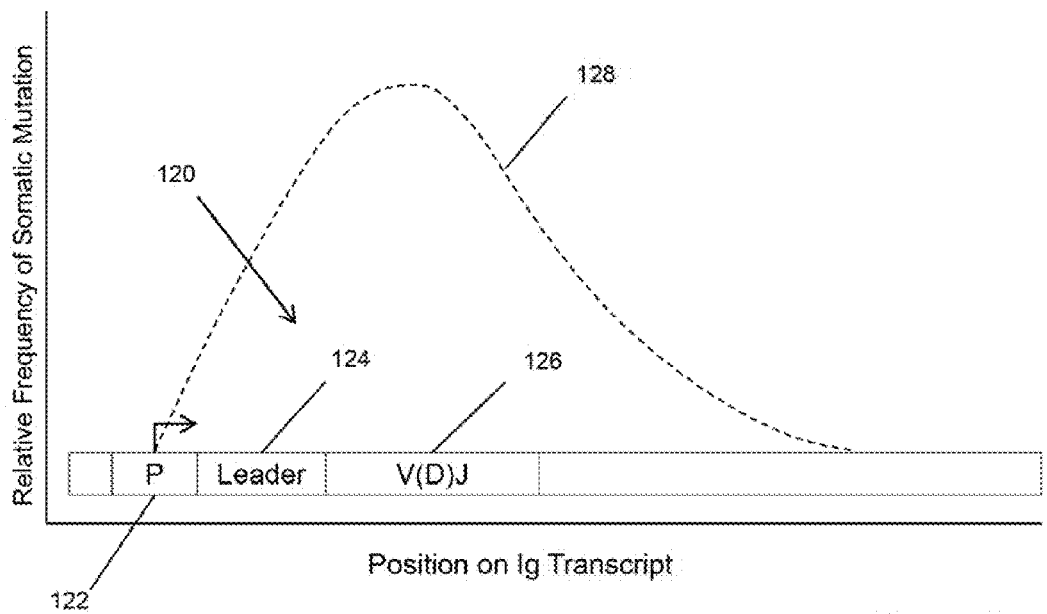
FIG. 1B illustrates the relative distribution of somatic mutations that occurs in immunoglobulins produced by B cells.

In another aspect the invention is directed to methods of analyzing sequences of complex populations of nucleic acids, particularly those having sequence variability in confined regions, such as V(D)J regions of immunoglobulin genes and transcripts or hypervariable regions in the microbial 16S rDNA gene. In one aspect, such complex populations are amplified and/or sequenced by using redundant primers annealing to different sites in regions of sequence variability. This is particularly advantageous where a sequencing chemistry is employed that has a relatively high error rate or where such sequence variability is difficult or impossible to know beforehand, such as in regions of somatically hypermutated immunoglobulin genes or transcripts. Thus, in the latter case, primer extension for amplification or generation of sequence reads takes place even if one or more primer binding sites are inoperable, or substantially inoperable, because of mismatches caused (for example) by one or more somatic mutations. FIG. 1B illustrates the distribution of mutations in IgH transcripts (120). Starting from promoter P (122) relative frequency shown by curve (128) climbs through leader region (124) to a maximum over the V(D)J region (126) of the transcript after which it drop to near zero. In one aspect of the invention, a segment of recombined B cell nucleic acid is amplified by a PCR with a plurality of forward primers or a plurality of reverse primers to generate a nested set of templates (see FIGS. 4A and 4B and their descriptions below). Templates from such a set may be further amplified on a surface to form separate amplicons (e.g. by bridge PCR using a cBot instrument, Illumina, San Diego, Calif.). Templates from the same nested set may be associated with one another by sequence reads generated at their common ends. Nested sets of templates allow a sequencing chemistry with relative high error rates to be used to analyze longer sequences than otherwise would be possible, while at the same time maintaining high average quality scores over the entire length of the sequence. The nested sets also ensure that at least one sequence read is obtained from a V region even if it has been subjected to somatic hypermutation. In one embodiment, sequencing chemistries may be used for analyzing highly variable nucleic acids, such as IgH molecules, that have error rates no better than the following: 0.2 percent of sequence reads contain at least one error in positions 1-50; 0.2-1.0 percent of sequence reads contain at least one error in positions 51-75; 0.5-1.5 percent of sequence reads contain at least one error in positions 76-100; and 1-5 percent of sequence reads contain at least one error in positions 101-125. In another embodiment, sequencing primer binding sites are positioned so that when extended they produce a series of sequence reads where each sequence read except the last overlaps its immediately adjacent downstream primer binding site and/or sequence read, thereby providing continuous sequence coverage with higher quality scores than would be possible if a single long template were used to generate a single long sequence read.

Complex populations of nucleic acids for analysis may arise from a variety of sources. Immune system repertoires may be obtained from samples of immune cells. For example, immune cells can include T-cells and/or B-cells. T-cells (T lymphocytes) include, for example, cells that express T cell receptors. T-cells include Helper T cells (effector T cells or Th cells), cytotoxic T cells (CTLs), memory T cells, and regulatory T cells. The sample can include a single cell in some applications or more generally at least 1,000, at least 10,000, at least 100,000, at least 250,000, at least 500,000, at least 750,000, or at least 1,000,000 T-cells.

B-cells include, for example, plasma B cells, memory B cells, B1 cells, B2 cells, marginal-zone B cells, and follicular B cells. B-cells can express immunoglobulins (antibodies, B cell receptor). The sample can include a single cell in some applications (e.g., a calibration test to define relevant B cells) or more generally at least 1,000, at least 10,000, at least 100,000, at least 250,000, at least 500,000, at least 750,000, or at least 1,000,000 B-cells.

The sample can include nucleic acid, for example, DNA (e.g., genomic DNA or mitochondrial DNA) or RNA (e.g., messenger RNA or microRNA). The nucleic acid can be cell-free DNA or RNA, e.g., extracted from the circulatory system, Vlassov et al, Curr. Mol. Med., 10: 142-165 (2010); Swamp et al. FEBS Lett., 581: 795-799 (2007). In the methods of the provided invention, the amount of RNA or DNA from a subject that can be analyzed includes, for example, as low as a single cell in some applications (e.g., a calibration test) and as many as 10 million of cells or more translating to a range of DNA of 6 pg-60 ug, and RNA of approximately 1 pg-10 ug.

As discussed more fully below (Definitions), a sample of lymphocytes is sufficiently large so that substantially every T cell or B cell with a distinct clonotype is represented therein, thereby forming a repertoire (as the term is used herein). In one embodiment, a sample is taken that contains with a probability of ninety-nine percent every clonotype of a population present at a frequency of 0.001 percent or greater. In another embodiment, a sample is taken that contains with a probability of ninety-nine percent every clonotype of a population present at a frequency of 0.0001 percent or greater. In one embodiment, a sample of B cells or T cells includes at least a half million cells, and in another embodiment such sample includes at least one million cells.

Whenever a source of material from which a sample is taken is scarce, such as, clinical study samples, or the like, DNA from the material may be amplified by a non-biasing technique, such as whole genome amplification (WGA), multiple displacement amplification (MDA); or like technique. e.g. Hawkins et al, Curr. Opin. Biotech., 13: 65-67 (2002); Dean et al, Genome Research. 11: 1095-1099 (2001); Wang et al, Nucleic Acids Research, 32: e76 (2004); Hosono et al. Genome Research. 13: 954-964 (2003); and the like.

Blood samples are of particular interest, especially in monitoring lymphoid neoplasms, such as lymphomas, leukemias, or the like, and may be obtained using conventional techniques, e.g. Innis et al, editors, PCR Protocols (Academic Press, 1990); or the like. For example, white blood cells may be separated from blood samples using convention techniques, e.g. RosetteSep kit (Stem Cell Technologies, Vancouver, Canada). Blood samples may range in volume from 100 µL to 10 mL; in one aspect, blood sample volumes are in the range of from 200 100 µL to 2 mL. DNA and/or RNA may then be extracted from such blood sample using conventional techniques for use in methods of the invention, e.g. DNeasy Blood & Tissue Kit (Qiagen, Valencia, Calif.). Optionally, subsets of white blood cells, e.g. lymphocytes, may be further isolated using conventional techniques, e.g. fluorescently activated cell sorting (FACS)(Becton Dickinson, San Jose, Calif.), magnetically activated cell sorting (MACS)(Miltenyi Biotec, Auburn, Calif.), or the like.

In other embodiments, nucleic acids are analyzed from a sample of a subset of cells. A method to separate cells, for example by using a cell surface marker, can be employed. For example, cells can be isolated by cell sorting flow-cytometry, flow-sorting, fluorescent activated cell sorting (FACS), bead based separation such as magnetic cell sorting (MACS; e.g., using antibody coated magnetic particles), size-based separation (e.g., a sieve, an array of obstacles, or a filter), sorting in a microfluidics device, antibody-based separation, sedimentation, affinity adsorption, affinity extraction, or density gradient centrifugation. Cells can be purified by laser capture microdissection. Sorting can be based on cell size, morphology, or intracellular or extracellular markers. Methods for isolating or sorting tumor cells are described, for example, in Nagrath S. et al. (2007) Nature 450:1235-1239; U.S. Pat. Nos. 6,008,002, 7,232,653, and 7,332,288; PCT Publication No. WO2008157220A1; and US Patent Application Nos. US20080138805A1 and US20090186065; and Rosenberg R. et al. (2002) Cytometry 49:150-158, each of which is herein incorporated by reference in their entireties.

Since the identifying recombinations are present in the DNA of each individual's adaptive immunity cell as well as their associated RNA transcripts, either RNA or DNA can be sequenced in the methods of the provided invention. A recombined sequence from a T-cell or B-cell encoding a T cell receptor or immunoglobulin molecule, or a portion thereof, is referred to as a clonotype. The DNA or RNA can correspond to sequences from T-cell receptor (TCR) genes or immunoglobulin genes that encode antibodies. For example, the DNA and RNA can correspond to sequences encoding α, β, γ, or δ chains of a TCR. In a majority of T-cells, the TCR is a heterodimer consisting of an α-chain and β-chain. The TCRα chain is generated by VJ recombination, and the β chain receptor is generated by V(D)J recombination. For the TCRβ chain, in humans there are 48 V segments, 2 D segments, and 13 J segments. Several bases may be deleted and others added (called N and P nucleotides) at each of the two junctions. In a minority of T-cells, the TCRs consist of γ and δ delta chains. The TCR γ chain is generated by VJ recombination, and the TCR δ chain is generated by V(D)J recombination (Kenneth Murphy, Paul Travers, and Mark Walport, *Janeway Immunology* 7th edition, Garland Science, 2007, which is herein incorporated by reference in its entirety).

The DNA and RNA analyzed in the methods of the invention can correspond to sequences encoding heavy chain immunoglobulins (IgH) with constant regions (α, δ, ε, γ, or μ) or light chain immunoglobulins (IgK or IgL) with constant regions λ or κ. Each antibody has two identical light chains and two identical heavy chains. Each chain is composed of a constant (C) and a variable region. For the heavy chain, the variable region is composed of a variable (V), diversity (D), and joining (J) segments. Several distinct sequences coding for each type of these segments are present in the genome. A specific VDJ recombination event occurs during the development of a B-cell, marking that cell to generate a specific heavy chain. Diversity in the light chain is generated in a similar fashion except that there is no D region so there is only VJ recombination. Somatic mutation often occurs close to the site of the recombination, causing the addition or deletion of several nucleotides, further increasing the diversity of heavy and light chains generated by B-cells. The possible diversity of the antibodies generated by a B-cell is then the product of the different heavy and light chains. The variable regions of the heavy and light chains contribute to form the antigen recognition (or binding) region or site. Added to this diversity is a process of somatic hypermutation which can occur after a specific response is mounted against some epitope.

As mentioned above, in accordance with the invention, primers may be selected to generate amplicons of subsets of recombined nucleic acids extracted from lymphocytes. Such subsets may be referred to herein as "somatically rearranged regions." Somatically rearranged regions may comprise nucleic acids from developing or from fully developed lymphocytes, where developing lymphocytes are cells in which rearrangement of immune genes has not been completed to form molecules having full V(D)J regions. Exemplary incomplete somatically rearranged regions include incomplete IgH molecules (such as, molecules containing only D-J regions), incomplete TCRδ molecules (such as, molecules containing only D-J regions), and inactive IgK (for example, comprising Kde-V regions).

Adequate sampling of the cells is an important aspect of interpreting the repertoire data, as described further below in the definitions of "clonotype" and "repertoire." For example, starting with 1,000 cells creates a minimum frequency that the assay is sensitive to regardless of how many sequencing reads are obtained. Therefore one aspect of this invention is the development of methods to quantitate the number of input immune receptor molecules. This has been implemented this for TCRβ and IgH sequences. In either case the same set of primers are used that are capable of amplifying all the different sequences. In order to obtain an absolute number of copies, a real time PCR with the multiplex of primers is performed along with a standard with a known number of immune receptor copies. An example of real time PCR data for the mouse vaccination example is shown in FIG. 9. This real time PCR measurement can be made from the amplification reaction that will subsequently be sequenced or can be done on a separate aliquot of the same sample. In the case of DNA, the absolute number of rearranged immune receptor molecules can be readily converted to number of cells (within 2 fold as some cells will have 2 rearranged copies of the specific immune receptor assessed and others will have one). In the case of cDNA the measured total number of rearranged molecules in the real time sample can be extrapolated to define the total number of these molecules used in another amplification reaction of the same sample. In addition, this method can be combined with a method to determine the total amount of RNA to define the number of rearranged immune receptor molecules in a unit amount (say 1 μg) of RNA assuming a specific efficiency of cDNA synthesis. If the total amount of cDNA is measured then the efficiency of cDNA synthesis need not be considered. If the number of cells is also known then the rearranged immune receptor copies per cell can be computed. If the number of cells is not known, one can estimate it from the total RNA as cells of specific type usually generate comparable amount of RNA. Therefore from the copies of rearranged immune receptor molecules per 1 μg one can estimate the number of these molecules per cell.

One disadvantage of doing a separate real time PCR from the reaction that would be processed for sequencing is that there might be inhibitory effects that are different in the real time PCR from the other reaction as different enzymes, input DNA, and other conditions may be utilized. Processing the products of the real time PCR for sequencing would ameliorate this problem. However low copy number using real time PCR can be due to either low number of copies or to inhibitory effects, or other suboptimal conditions in the reaction.

Another approach that can be utilized is to add a known amount of unique immune receptor rearranged molecules with a known sequence, i.e. known amounts of one or more internal standards, to the cDNA or genomic DNA from a sample of unknown quantity. By counting the relative number of molecules that are obtained for the known added sequence compared to the rest of the sequences of the same sample, one can estimate the number of rearranged immune receptor molecules in the initial cDNA sample. (Such techniques for molecular counting are well-known, e.g. Brenner et al, U.S. Pat. No. 7,537,897, which is incorporated herein by reference). Data from sequencing the added unique sequence can be used to distinguish the different possibilities if a real time PCR calibration is being used as well. Low copy number of rearranged immune receptor in the DNA (or cDNA) would create a high ratio between the number of molecules for the spiked sequence compared to the rest of the sample sequences. On the other hand, if the measured low copy number by real time PCR is due to inefficiency in the reaction, the ratio would not be high.

In one aspect, the invention provides methods for measuring clonotype expression at a cellular level. That is, as noted above, clonotypes may be used to count lymphocytes; therefore, by measuring clonotypes derived from genomic DNA and the same clonotypes derived from RNA, cell-based expression of clonotypes may be determined. A method for simultaneously measuring lymphocyte numbers and clonotype expression levels in a sample may comprise the steps of: (a) obtaining from an individual a sample comprising T cells and/or B cells; (b) sequencing spatially isolated individual molecules derived from genomic DNA of said cells, such spatially isolated individual molecules comprising a number of clonotypes corresponding to a number of lymphocytes in the sample; (c) sequencing spatially isolated individual molecules derived from RNA of said cells, such spatially isolated individual molecules comprising numbers of clonotypes corresponding to expression levels thereof in the lymphocytes of the sample: and (d) determining clonotype expression levels in lymphocytes of the sample by comparing for each clonotype the number determined from isolated individual molecules derived from genomic DNA of said cells and the number determined from isolated individual molecules derived from RNA of said cells. Genomic DNA and RNA are readily extracted from the same sample using commercially available kits, such as the AllPrep DNA/RNA Mini Kit (Qiagen GmbH, Germany). As mentioned above, in one embodiment, the step of determining further includes determining said number of lymphocytes in said sample by adding a known quantity of an internal standard to said genomic DNA. In another embodiment, where for example the sample is peripheral blood, the sample has a defined volume which permits a concentration of said lymphocytes to be determined in said sample. Typically, such a defined volume is in the range of from 1 mL to 50 mL, and more usually, in the range of from 1 mL to 10 mL. In another embodiment, numbers of the same clonotype derived from genomic DNA and RNA are compared by simply dividing the number of clonotypes determined from the isolated individual molecules derived from the RNA by the number of clonotypes determined from the isolated individual molecules derived from said genomic DNA. Such two sets of clonotypes are readily distinguished in the same sequencing run by the use of labels, particularly oligonucleotide tags that are attached during the sample preparation process. For Solexa-based sequencing, such labels may be incorporated with the tags used to identify different samples by (for example) adding a single nucleotide to the tag to indicate DNA or RNA, or simply using an additional tag so that each patient sample is labeled with two tags, one for the genomic DNA fraction and one for the RNA fraction. Thus, said step of sequencing said spatially isolation individual molecules derived from said RNA may include labeling each of said spatially isolated individual molecules with a first label indicating its RNA origin and said step of sequencing said spatially isolation individual molecules derived from said genomic DNA may include labeling each of said spatially isolated individual molecules with a second label indicating its genomic DNA origin such that the first label is distinguishable from the second label. In one embodiment, such labels are distinct oligonucleotide tags that are identified by sequencing.

Likewise, the invention may be used to provide simultaneously (this is, based on measurements on a single sample) lymphocyte number and clonality. Such embodiment may be implemented with the following steps: (a) obtaining from an individual a sample comprising T cells and/or B cells: (b) sequencing spatially isolated individual molecules derived from nucleic acid of said cells, such spatially isolated individual molecules comprising a number of clonotypes corresponding to a number of lymphocytes in the sample; (c) determining the number of lymphocytes from the number of spatially isolated individual molecules; (d) determining abundances of different sequences of the spatially isolated individual molecules to generate a clonotype profile and a measure of clonality based thereon. The nucleic acid from the lymphocytes may be genomic DNA and/or RNA; however, preferably the nucleic acid is genomic DNA. Similarly as above, in one embodiment, the step of determining said number further includes determining said number of lymphocytes in said sample by adding a known quantity of an internal standard to said genomic DNA. And similarly, when the sample is a peripheral blood sample it has a defined volume so that a concentration of said lymphocytes in said sample is determined. In some embodiments of the above, only B cells are employed and in other embodiments only T cells are employed.

Amplification of Nucleic Acid Populations

As noted below, amplicons of target populations of nucleic acids may be generated by a variety of amplification techniques. In one aspect of the invention, multiplex PCR is used to amplify members of a mixture of nucleic acids, particularly mixtures comprising recombined immune molecules such as T cell receptors, B cell receptors, or portions thereof. Guidance for carrying out multiplex PCRs of such immune molecules is found in the following references, which are incorporated by reference: Morley. U.S. Pat. No. 5,296,351; Gorski, U.S. Pat. No. 5,837,447; Dau. U.S. Pat. No. 6,087,096; Von Dongen et al, U.S. patent publication 2006/0234234; European patent publication EP 1544308B1; and the like. The foregoing references describe the technique referred to as "spectratyping," where a population of immune molecules are amplified by multiplex PCR after which the sequences of the resulting amplicon are physically separated, e.g. by electrophoresis, in order to determine whether there is a predominant size class. Such a class would indicate a predominant clonal population of lymphocytes which, in turn, would be indicative of disease state. In spectratyping, it is important to select primers that display little or no cross-reactivity (i.e. that do not anneal to binding sites of other primers); otherwise there may be a false representation of size classes in the amplicon. In the present invention, so long as the nucleic acids of a population are uniformly amplified, cross-reactivity of primers is permissible because the sequences of the amplified nucleic acids are analyzed in the present invention, not merely their sizes. As described more fully below, in one aspect, the step of spatially isolating individual nucleic acid molecules is achieved by carrying out a primary multiplex amplification of a preselected somatically rearranged region or portion thereof (i.e. target sequences) using forward and reverse primers that each have tails non-complementary to the target sequences to produce a first amplicon whose member sequences have common sequences at each end that allow further manipulation. For example, such common ends may include primer binding sites for continued amplification using just a single forward primer and a single reverse primer instead of multiples of each, or for bridge amplification of individual molecules on a solid surface, or the like. Such common ends may be added in a single amplification as described above, or they may be added in a two-step procedure to avoid difficulties associated with manufacturing and exercising quality control over mixtures of long primers (e.g. 50-70 bases or more). In such a two-step process (described more fully below and illustrated in FIGS. 4A-4B), the primary amplification is carried out as described above, except that the primer tails are limited in length to provide only forward and reverse primer binding sites at the ends of the sequences of the first amplicon. A secondary amplification is then carried out using secondary amplification primers specific to these primer binding sites to add further sequences to the ends of a second amplicon. The secondary amplification primers have tails non-complementary to the target sequences, which form the ends of the second amplicon and which may be used in connection with sequencing the clonotypes of the second amplicon. In one embodiment, such added sequences may include primer binding sites for generating sequence reads and primer binding sites for carrying out bridge PCR on a solid surface to generate clonal populations of spatially isolated individual molecules, for example, when Solexa-based sequencing is used. In this latter approach, a sample of sequences from the second amplicon are disposed on a solid surface that has attached complementary oligonucleotides capable of annealing to sequences of the sample, after which cycles of primer extension, denaturation, annealing are implemented until clonal populations of templates are formed. Preferably, the size of the sample is selected so that (i) it includes an effective representation of clonotypes in the original sample, and (ii) the density of clonal populations on the solid surface is in a range that permits unambiguous sequence determination of clonotypes.

TCR or BCR sequences or portions thereof can be amplified from nucleic acid in a multiplex reaction using at least one primer that anneals to the C region and one or more primers that can anneal to one or more V segments (as illustrated in FIGS. 2A-2B and FIGS. 4A-4B and discussed more fully below). The number of primers that anneal to V segments in a multiplex reaction can be, for example, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80. The number of primers that anneal to V segments in a multiplex reaction can be, for example, 10-60, 20-50, 30-50, 40-50, 20-40, 30-40, or 35-40. The primers can anneal to different V segments. For IgH genes, because of the possibility of somatic mutations in the V segments, multiple primers that anneal to each V segment can be used: for example, 1, 2, 3, 4, or 5 primers per V segment. The number of primers that anneal to C segments in a multiplex reaction can include, for example, at least 1, 2, 3, 4, 5, 6, 7, 8, 9, 10, 11, 12, 13, 14, or 15. The number of primers that anneal to C segments in a multiplex reaction can be 1-10, 2-9, 3-8, 4-7, 3-8, or 3-6. Amplification of TCR or immunoglobulin genes can occur as described in Example 3 and/or Example 4.

The region to be amplified can include the full clonal sequence or a subset of the clonal sequence, including the V-D junction, D-J junction of an immunoglobulin or T-cell receptor gene, the full variable region of an immunoglobulin or T-cell receptor gene, the antigen recognition region, or a CDR, e.g., complementarity determining region 3 (CDR3).

Figure 3B:
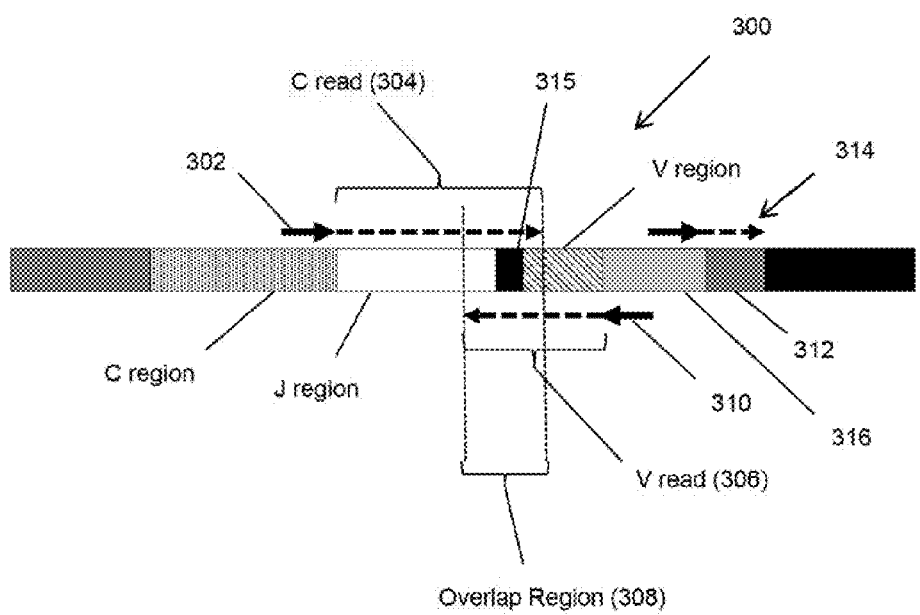
FIG. 3B illustrates details of determining a nucleotide sequence of the PCR product of FIG. 3A.

The TCR or immunoglobulin sequence can amplified using a primary and a secondary amplification step. Each of the different amplification steps can comprise different primers. The different primers can introduce sequence not originally present in the immune gene sequence. For example, the amplification procedure can add new primer binding sites to the ends of the target sequences to convert a multiplex amplification to a singleplex amplification or the amplification procedure can acid one or more tags to the 5' and/or 3' end of amplified TCR or immunoglobulin sequence (as illustrated in FIGS. 3A-3B). The tag can be sequence that facilitates subsequent sequencing of the amplified DNA. The tag can be sequence that facilitates binding the amplified sequence to a solid support.

Other methods for amplification may not employ any printers in the V region. Instead, a specific primer can be used from the C segment and a generic primer can be put in the other side (5'). The generic primer can be appended in the cDNA synthesis through different methods including the well described methods of strand switching. Similarly, the generic primer can be appended after cDNA making through different methods including ligation.

Other means of amplifying nucleic acid that can be used in the methods of the provided invention include, for example, reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification, Circle to Circle Amplification, SPIA amplification, Target Amplification by Capture and Ligation (TACL) amplification, and RACE amplification.

The information in RNA in a sample can be converted to cDNA by using reverse transcription. PolyA printers, random primers, and/or gene specific primers can be used in reverse transcription reactions in accordance with conventional protocols.

After amplification of DNA from the genome (or amplification of nucleic acid in the form of cDNA by reverse transcribing RNA), the individual nucleic acid molecules can be isolated, optionally re-amplified, and then sequenced individually. Exemplary amplification protocols may be found in van Dongen et al, Leukemia, 17: 2257-2317 (2003) or van Dongen et al, U.S. patent publication 2006/0234234, which is incorporated by reference. Briefly, an exemplary protocol is as follows: Reaction buffer: ABI Buffer II or ABI Gold Buffer (Life Technologies, San Diego, Calif.); 50 µL final reaction volume; 100 ng sample DNA; 10 pmol of each primer (subject to adjustments to balance amplification as described below); dNTPs at 200 µM final concentration; $MgCl_2$ at 1.5 mM final concentration (subject to optimization depending on target sequences and polymerase); Taq polymerase (1-2 U/tube); cycling conditions: preactivation 7 min at 95° C.; annealing at 60° C.; cycling times: 30 s denaturation; 30 s annealing; 30 s extension.

Polymerases that can be used for amplification in the methods of the invention are commercially available and include, for example, Taq polymerase. AccuPrime polymerase, or Pfu. The choice of polymerase to use can be based on whether fidelity or efficiency is preferred.

Methods for isolation of nucleic acids from a pool include subcloning nucleic acid into DNA vectors and transforming bacteria (bacterial cloning), spatial separation of the molecules in two dimensions on a solid substrate (e.g., glass slide), spatial separation of the molecules in three dimensions in a solution within micelles (such as can be achieved using oil emulsions with or without immobilizing the molecules on a solid surface such as beads), or using microreaction chambers in, for example, microfluidic or nano-fluidic chips. Dilution can be used to ensure that on average a single molecule is present in a given volume, spatial region, bead, or reaction chamber. Guidance for such methods of isolating individual nucleic acid molecules is found in the following references: Sambrook, Molecular Cloning: A Laboratory Manual (Cold Spring Harbor Laboratory Press, 2001s); Shendure et al, Science, 309: 1728-1732 (including supplemental material) (2005); U.S. Pat. No. 6,300,070; Bentley et al, Nature, 456: 53-59 (including supplemental material) (2008); U.S. Pat. No. 7,323,305; Matsubara et al, Biosensors & Bioelectronics, 20:1482-1490 (2005): U.S. Pat. No. 6,753,147; and the like.

Real time PCR, picogreen staining, nanofluidic electrophoresis (e.g. LabChip) or UV absorption measurements can be used in an initial step to judge the functional amount of amplifiable material.

Methods for re-amplification of nucleic acids include bacterial growth of isolated colonies transformed with nucleic acid, amplification on a slide (e.g., PCR colonies (polonies)), and amplification on a bead (e.g. in an emulsion PCR). The same method can be used to amplify and re-amplify the nucleic acid or a different method can be used to amplify and reamplify the nucleic acid.

In certain embodiments the subcloning steps include a step in which a common primer is attached to the DNA or RNA through an amplification or ligation step. This primer is then used to amplify the clones and as a recognition sequence for hybridization of a primer for sequencing (e.g. as illustrated in FIGS. 2A-2B and 4A-4B, and discussed more fully below).

In one aspect, multiplex amplifications are carried out so that relative amounts of sequences in a starting population are substantially the same as those in the amplified population, or amplicon. That is, multiplex amplifications are carried out with minimal amplification bias among member sequences of a sample population. In one embodiment, such relative amounts are substantially the same if each relative amount in an amplicon is within five fold of its value in the starting sample. In another embodiment, such relative amounts are substantially the same if each relative amount in an amplicon is within two fold of its value in the starting sample. As discussed more fully below, amplification bias in PCR may be detected and corrected using conventional techniques so that a set of PCR primers may be selected for a predetermined repertoire that provide unbiased amplification of any sample.

In regard to many repertoires based on TCR or BCR sequences, a multiplex amplification optionally uses all the V segments. The reaction is optimized to attempt to get amplification that maintains the relative abundance of the sequences amplified by different V segment primers. Some of the primers are related, and hence many of the primers may "cross talk," amplifying templates that are not perfectly matched with it. The conditions are optimized so that each template can be amplified in a similar fashion irrespective of which primer amplified it. In other words if there are two templates, then after 1,000 fold amplification both templates can be amplified approximately 1,000 fold, and it does not matter that for one of the templates half of the amplified products carried a different primer because of the cross talk. In subsequent analysis of the sequencing data the primer sequence is eliminated from the analysis, and hence it does not matter what primer is used in the amplification as long as the templates are amplified equally.

Since the amount of each template is not known in a cDNA population generated from mRNA, a set of standards may be generated using singleplex PCRs of a cDNA population of clonotypes. This was carried out for a repertoire of TCRβ clonotypes. The product in each of 34 such PCRs (using in the separate reactions primers of Example 3) comprised a plurality of sequences with one V primer. The different products were carefully quantitated to create a set of standards at the same concentration. A pool of all 34 primers was used and 34 real time PCRs were performed using the pool of primers and each of the standard sequences as a template. Ideally without bias all the 34 standards will show equal efficiency of amplification by real time PCR. That suggests that each sequence is amplified equally even though the presence of cross talk makes it unclear what primers are carrying out the amplification. This optimization is consistent with the goal of having equal amplification irrespective of the actual primers that is incorporated in the amplification product. Increasing the total primer pool concentration significantly reduced the dynamic range as expected from increasing the efficiency of the amplification. Furthermore for templates that seemed to amplify more efficiently than the average, the concentration of their perfectly matched printer in the pool was decreased. Conversely for templates that were inefficiently amplified the concentration of their perfectly matched primer was increased. This optimization demonstrated that all the templates are amplified within two fold of the average amplification.

Amplification bias may also be avoided by carrying out a two-stage amplification (as illustrated in FIGS. 2A-2B) wherein a small number of amplification cycles are implemented in a first, or primary, stage using primers having tails non-complementary with the target sequences. The tails include primer binding sites that are added to the ends of the sequences of the primary amplicon so that such sites are used in a second stage amplification using only a single forward printer and a single reverse primer, thereby eliminating a primary cause of amplification bias. Preferably, the primary PCR will have a small enough number of cycles (e.g. 5-10) to minimize the differential amplification by the different primers. The secondary amplification is done with one pair of primers and hence the issue of differential amplification is minimal. One percent of the primary PCR is taken directly to the secondary PCR. Thirty-five cycles (equivalent to ~28 cycles without the 100 fold dilution step) used between the two amplifications were sufficient to show a robust amplification irrespective of whether the breakdown of cycles were: one cycle primary and 34 secondary or 25 primary and 10 secondary. Even though ideally doing only 1 cycle in the primary PCR may decrease the amplification bias, there are other considerations. One aspect of this is representation. This plays a role when the starting input amount is not in excess to the number of reads ultimately obtained. For example, if 1,000,000 reads are obtained and starting with 1,000,000 input molecules then taking only representation from 100,000 molecules to the secondary amplification would degrade the precision of estimating the relative abundance of the different species in the original sample. The 100 fold dilution between the 2 steps means that the representation is reduced unless the primary PCR amplification generated significantly more than 100 molecules. This indicates that a minimum 8 cycles (256 fold), but more comfortably 10 cycle (~1,000 fold), may be used. The alternative to that is to take more than 1% of the primary PCR into the secondary but because of the high concentration of primer used in the primary PCR, a big dilution factor is can be used to ensure these primers do not interfere in the amplification and worsen the amplification bias between sequences. Another alternative is to add a purification or enzymatic step to eliminate the primers from the primary PCR to allow a smaller dilution of it. In this example, the primary PCR was 10 cycles and the second 25 cycles.

Figure 5:
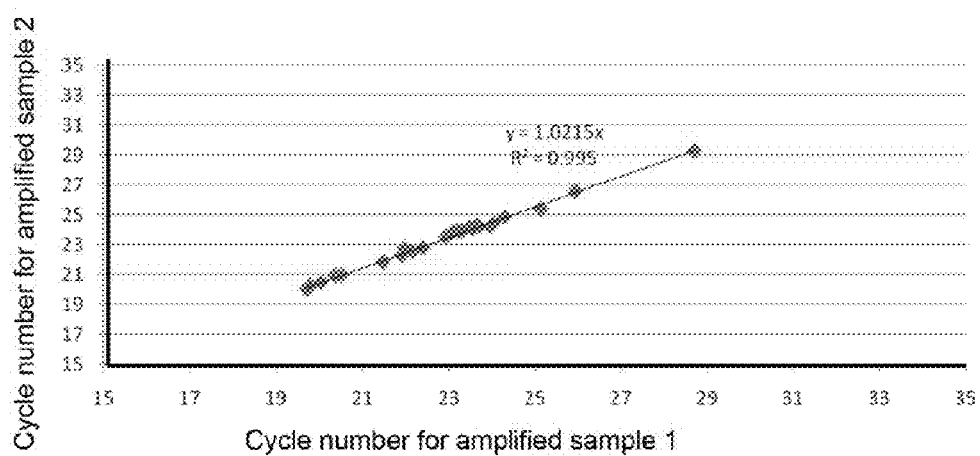
FIG. 5 shows data evidencing the reproducibility of multiplex PCRs of the invention.

The reproducibility of a multiplex PCR may be assessed as follows, as exemplified with the test set of primers from Example 2. Two primary PCR reactions are performed using the test set of primers, e.g. the pooled TCRβ primers and the C primer (of Example 2) and one cDNA sample as a template. The relative abundance in each amplified template is assessed using real time PCR. Using each of the two amplified products as a template, thirty four different real time PCR reactions were performed using the C primer and one of the V primers in each reaction. The data shown in FIG. 5 demonstrate that the relative abundance determined by real time PCR was highly reproducible using all the V primers for two samples, indicating that the multiplexed amplification is highly reproducible. The cycle number (Ct value) for each of the real time PCR amplifications using the one multiplexed amplification product as a template is shown on the X axis and using the second multiplexed amplification product as a template is depicted on the Y axis.

Figure 6:
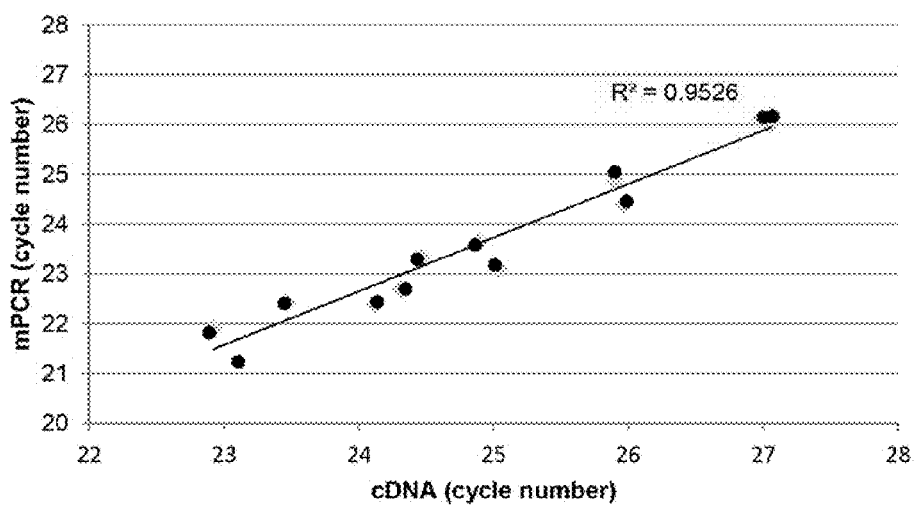
FIG. 6 shows data that demonstrate that multiplex PCRs of the invention introduce minimal amplification bias.

The amount of amplification bias of a set of primers may be assessed using the following procedure, which is exemplified using the primer set of Example 2. The test primer set (as above) is used to amplify a cDNA as a template (e.g. obtained from mRNA extracted from lymphocytes). The amount of template amplified by each of the 34 different primers (along with C segment primer) is determined using real time PCR and that amount is compared with the amount amplified using the same primers with the cDNA. Since there may be cross talk even if the relative abundance among the internal sequences in the amplified product and the cDNA were the same, only significant differences in amplification may be detected using this readout. This possibility may be tested by synthesizing collection of primers to amplify internal segments of a number of the starting cDNA sequences. For example, 12 oligos were designed that can, when used with C segment primer, amplify sequences internal to the above V segment primers. If there is minimal amplification bias, then the concentration of these internal sequences should change little between the starting cDNA and the amplified products. Data from this example is shown in FIG. 6. There, a cDNA sample was used as a template for a multiplexed amplification using the pooled TCRβ primers and the C primer (from Example 2). The C primer and the downstream internal primers were used for the initial amplification of template material from the multiplex amplification. Similarly real time PCR was used to assess the relative abundance of these same sequences in the cDNA. If the multiplexed amplification had any signifcant biases, the relative abundance in the amplified material would be very different from that in the cDNA. As can be seen in FIG. 6, high correlation was seen demonstrating minimal amplification bias in the multiplexed amplification. The cycle number (Ct value) for each of the real time PCR amplification using internal primers, and cDNA and the multiplexed amplification product as template is shown on X and Y axis, respectively.

The initial amplification can be done from DNA or RNA (e.g., after conversion to cDNA).

Sequencing Nucleic Acid Populations

Any high-throughput technique for sequencing nucleic acids can be used in the method of the invention. DNA sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of the separated molecules has more recently been demonstrated by sequential or single extension reactions using polymerases or ligases as well as by single or sequential differential hybridizations with libraries of probes. These reactions have been performed on many clonal sequences in parallel including demonstrations in current commercial applications of over 100 million sequences in parallel. These sequencing approaches can thus be used to study the repertoire of T-cell receptor (TCR) and/or B-cell receptor (BCR). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores, produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect, for each sample from an individual, the sequencing technique used in the methods of the invention generates sequences of least 1000 clonotypes per run: in another aspect, such technique generates sequences of at least 10,000 clonotypes per run; in another aspect, such technique generates sequences of at least 100,000 clonotypes per run; in another aspect, such technique generates sequences of at least 500,000 clonotypes per run; and in another aspect, such technique generates sequences of at least 1,000,000 clonotypes per run. In still another aspect, such technique generates sequences of between 100,000 to 1,000,000 clonotypes per run per individual sample.

The sequencing technique used in the methods of the provided invention can generate about 30 bp, about 40 bp, about 50 bp, about 60 bp, about 70 bp, about 80 bp, about 90 bp, about 100 bp, about 110, about 120 bp per read, about 150 bp, about 200 bp, about 250 bp, about 300 bp, about 350 bp, about 400 bp, about 450 bp, about 500 bp, about 550 bp, or about 600 bp per read.

The sequencing technique used in the methods of the provided invention can generate at least 30, 40, 50, 60, 70, 80, 90, 100, 110, 120, 150, 200, 250, 300, 350, 400, 450, 500, 550, or 600 bp per read.

In one aspect, a sequence-based clonotype profile of an individual is obtained using the following steps: (a) obtaining a nucleic acid sample from T-cells and/or B-cells of the individual; (b) spatially isolating individual molecules derived from such nucleic acid sample, the individual molecules comprising nested sets of templates each generated from a nucleic acid in the sample and each containing a somatically rearranged region or a portion thereof, each nested set being capable of producing a plurality of sequence reads each extending in the same direction and each starting from a different position on the nucleic acid from which the nested set was generated; (c) sequencing said spatially isolated individual molecules; and (d) determining abundances of different sequences of the nucleic acid molecules from the nucleic acid sample to generate the clonotype profile. In one embodiment, the step of sequencing includes producing a plurality of sequence reads for each of the nested sets. In another embodiment, each of the somatically rearranged regions comprise a V region and a J region, and each of the plurality of sequence reads starts from a different position in the V region and extends in the direction of its associated J region. In another embodiment, the step of sequencing comprises bidirectionally sequencing each of the spatially isolated individual molecules to produce at least one forward sequence read and at least one reverse sequence read. Further to the latter embodiment, at least one of the forward sequence reads and at least one of the reverse sequence reads have an overlap region such that bases of such overlap region are determined by a reverse complementary relationship between such sequence reads. In still another embodiment, each of the somatically rearranged regions comprise a V region and a J region and the step of sequencing further includes determining a sequence of each of the individual nucleic acid molecules from one or more of its forward sequence reads and at least one reverse sequence read starting from a position in a J region and extending in the direction of its associated V region. In another embodiment, individual molecules comprise nucleic acids selected from the group consisting of complete IgH molecules, incomplete IgH molecules, complete IgK molecules, IgK inactive molecules, TCRβ molecules, TCRγ molecules, complete TCRδ molecules, and incomplete TCRδ molecules. In another embodiment, the step of sequencing comprises generating the sequence reads having monotonically decreasing quality scores. Further to the latter embodiment, monotonically decreasing quality scores are such that the sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100.

As noted below in the definition of repertoire, different predetermined regions of immunoglobulin or T cell receptor genes can be sequenced. In some embodiments, the full sequence of the variable regions can be sequenced to identify and quantify a clonotype.

A unique subset of the full clonal sequences can be sequenced. In some embodiments, nucleotides comprising the VD and the DJ junctions are sequenced to uniquely identify and quantify a clonotype. In other embodiments, the fragment that can be sequenced is the full variable region. In yet another embodiment, the antigen recognition region or the complementarity determining region 3 (CDR3) is sequenced. A fragment containing the full CDR3 or the full variable region can be amplified to allow the sequencing of the CDR3 comprising parts of the V, D, and J segments.

In one embodiment, only the CDR3 is amplified and sequenced. Amplification and sequencing of the CDR3 can be accomplished by using primers specific to one or more V segment sequences (as well as one or more primer(s) on the other side of the amplicon in the C segment). Primers for each of the V segments can be utilized in one or more amplification reactions leading to the amplification of the full repertoire of sequences. This repertoire of sequences can then be mixed and subjected to separation, with or without amplification, and sequenced using any of the sequencing techniques described. When the amplification with the various V primers is done in separate tubes, the number of molecules carrying the different V segments can be "normalized" due to PCR saturation. For example, if one particular V segment had one or several clonal expansions leading to its representation more than other segments this information may be erased or decreased since the PCR reaction for each segment can be driven to saturation or close to it. Real time PCR can be used to quantify how much of each V segment is present. The full CDR3 can be sequenced, or a subset of the sequence CDR3 can be sequenced.

In one embodiment, only a subset of clonotypes is analyzed. This can be accomplished by amplifying with a primer specific to the subset of clonotypes, for example, a primer that is specific to the V segment. Unique clonotypes can be identified by sequencing with long contiguous reads that provide full connectivity. In some embodiments, when several sequences of interest are present, a short read length across only one of the junctions can generate degenerate tags that are not unique to a specific clonotype but are shared among multiple clonotypes. For example sequencing across the V/J junction can lump all the sequences with the same V/J irrespective of the D segment as one clonotype. Information on the full connectivity of all segments allows sequences to be distinguished that may share the same V and J segments but are connected to different D segments, for example.

Clonotype Determination from Sequence Data

Figure 4A:
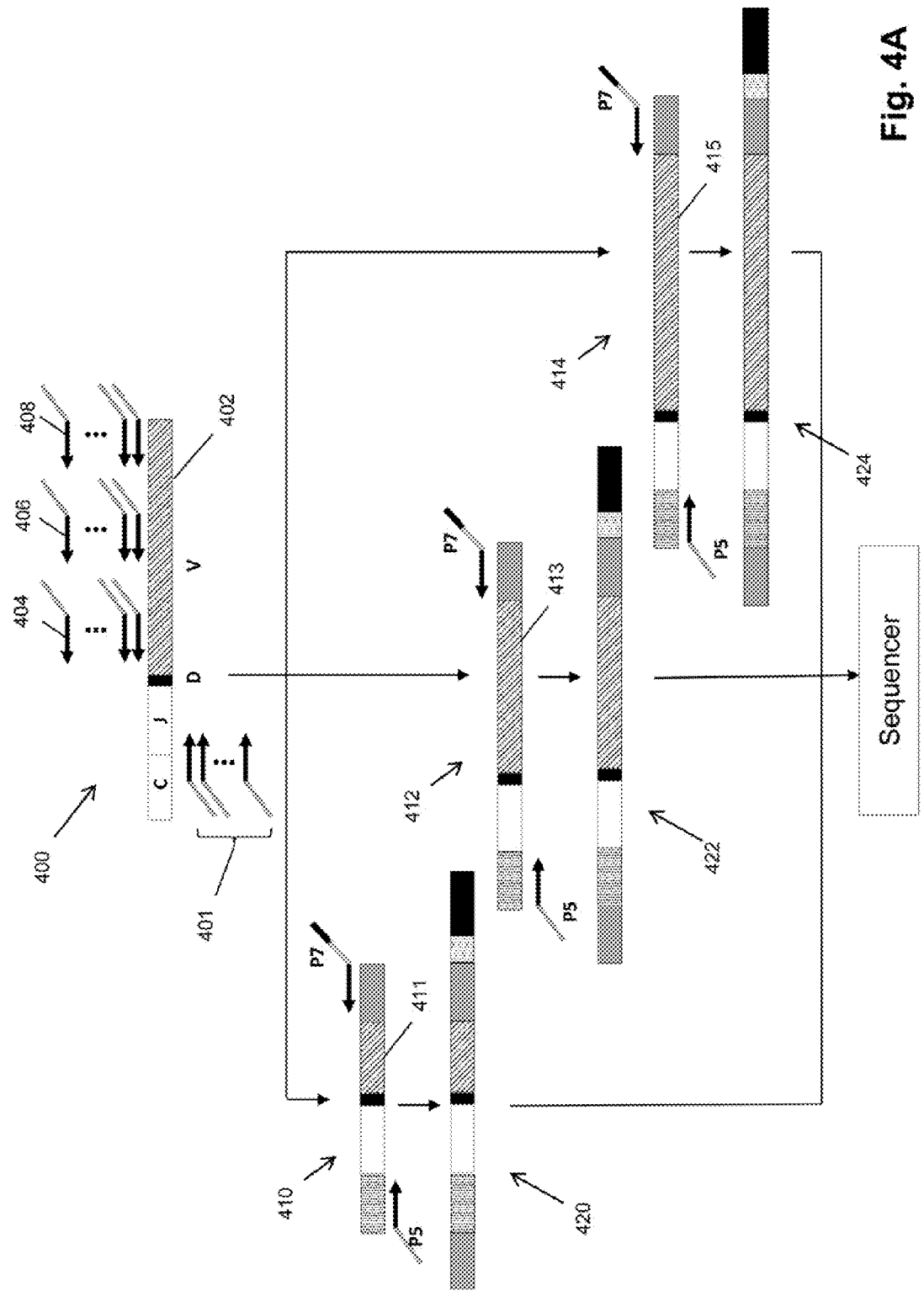
FIG. 4A illustrates a PCR scheme for generating three sequencing templates from an IgH chain in a single reaction.
Figure 4B:
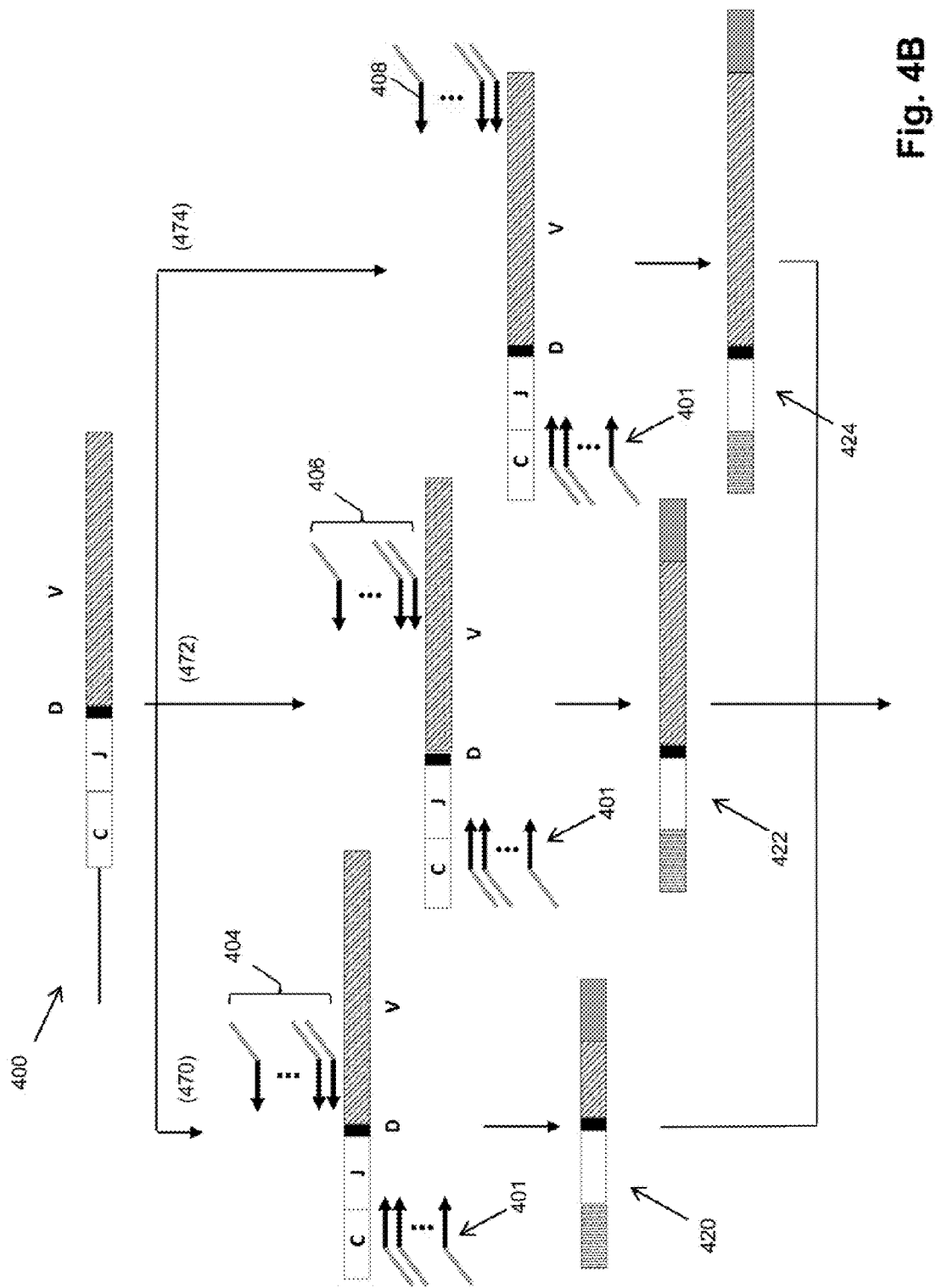

In one aspect of the invention, sequences of clonotypes (including but not limited to those derived from IgH, TCRα, TCRβ, TCRγ, and/or IgLκ (IgK)) may be determined by combining information from one or more sequence reads, for example, along the V(D)J regions of the selected chains. In another aspect, sequences of clonotypes are determined by combining information from a plurality of sequence reads. (As used herein, a "sequence read" is a sequence of data generated by a sequencing technique from which a sequence of nucleotides is determined. Typically, sequence reads are made by extending a primer along a template nucleic acid, e.g. with a DNA polymerase or a DNA ligase. Data is generated by recording signals, such as optical, chemical (e.g. pH change), or electrical signals, associated with such extension.) Such pluralities of sequence reads may include one or more sequence reads along a sense strand (i.e. "forward" sequence reads) and one or more sequence reads along its complementary strand (i.e. "reverse" sequence reads). When multiple sequence reads are generated along the same strand, separate templates are first generated by amplifying sample molecules with primers selected for the different positions of the sequence reads. This concept is illustrated in FIG. 4A where primers (404, 406 and 408) are employed to generate amplicons (410, 412, and 414, respectively) in a single reaction. Such amplifications may be carried out in the same reaction or in separate reactions. In one aspect, whenever PCR is employed, separate amplification reactions are used for generating the separate templates which, in turn, are combined and used to generate multiple sequence reads along the same strand. This latter approach is preferable for avoiding the need to balance primer concentrations (and/or other reaction parameters) to ensure equal amplification of the multiple templates (sometimes referred to herein as "balanced amplification" or "unbias amplification"). The generation of templates in separate reactions is illustrated in FIGS. 4B-4C. There a sample containing IgH (400) is divided into three portions (472, 474, and 476) which are added to separate PCRs using J region primers (401) and V region primers (404, 406, and 408, respectively) to produce amplicons (420, 422 and 424, respectively). The latter amplicons are then combined (478) in secondary PCR (480) using P5 and P7 primers to prepare the templates (482) for bridge PCR and sequencing on an Illumina GA sequencer, or like instrument.

Sequence reads of the invention may have a wide variety of lengths, depending in part on the sequencing technique being employed. For example, for some techniques, several trade-offs-may arise in its implementation, for example, (i) the number and lengths of sequence reads per template and (ii) the cost and duration of a sequencing operation. In one embodiment, sequence reads are in the range of from 20 to 400 nucleotides; in another embodiment, sequence reads are in a range of from 30 to 200 nucleotides; in still another embodiment, sequence reads are in the range of from 30 to 120 nucleotides. In one embodiment, 1 to 4 sequence reads are generated for determining the sequence of each clonotype; in another embodiment, 2 to 4 sequence reads are generated for determining the sequence of each clonotype; and in another embodiment, 2 to 3 sequence reads are generated for determining the sequence of each clonotype. In the foregoing embodiments, the numbers given are exclusive of sequence reads used to identify samples from different individuals. The lengths of the various sequence reads used in the embodiments described below may also vary based on the information that is sought to be captured by the read; for example, the starting location and length of a sequence read may be designed to provide the length of an NDN region as well as its nucleotide sequence; thus, sequence reads spanning the entire NDN region are selected. In other aspects, one or more sequence reads encompasses the D and/or NDN regions.

Figure 3C:
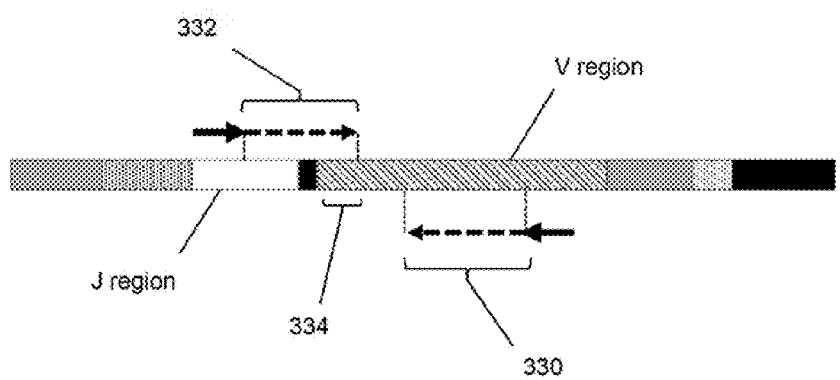
FIG. 3C illustrates details of another embodiment of determining a nucleotide sequence of the PCR product of FIG. 3A.

In another aspect of the invention, sequences of clonotypes are determined in part by aligning sequence reads to one or more V region reference sequences and one or more J region reference sequences, and in part by base determination without alignment to reference sequence, such as in the highly variable NDN region. A variety of alignment algorithms may be applied to the sequence reads and reference sequences. For example, guidance for selecting alignment methods is available in Batzoglou, Briefings in Bioinformatics, 6: 6-22 (2005), which is incorporated by reference. In one aspect, whenever V reads or C reads (described more fully below) are aligned to V and J region reference sequences, a tree search algorithm is employed, e.g. Cormen et al, Introduction to Algorithms, Third Edition (The MIT Press, 2009). The codon structures of V and J reference sequences may be used in an alignment process to remove sequencing errors and/or to determine a confidence level in the resulting alignment, as described more fully below. In another aspect, an end of at least one forward read and an end of at least one reverse read overlap in an overlap region (e.g. 308 in FIG. 3B), so that the bases of the reads are in a reverse complementary relationship with one another. Thus, for example, if a forward read in the overlap region is "5'-acgttgc", then a reverse read in a reverse complementary relationship is "5'-gcaacgt" within the same overlap region. In one aspect, bases within such an overlap region are determined, at least in part, from such a reverse complementary relationship. That is, a likelihood of a base call (or a related quality score) in a prospective overlap region is increased if it preserves, or is consistent with, a reverse complementary relationship between the two sequence reads. In one aspect, clonotypes of TCR β and IgH chains (illustrated in FIG. 3B) are determined by at least one sequence read starting in its J region and extending in the direction of its associated V region (referred to herein as a "C read" (304)) and at least one sequence read starting in its V region and extending in the direction of its associated J region (referred to herein as a "V read" (306)). Overlap region (308) may or may not encompass the NDN region (315) as shown in FIG. 3B. Overlap region (308) may be entirely in the J region, entirely in the NDN region, entirely in the V region, or it may encompass a J region-NDN region boundary or a V region-NDN region boundary, or both such boundaries (as illustrated in FIG. 3B). Typically, such sequence reads are generated by extending sequencing primers, e.g. (302) and (310) in FIG. 3B, with a polymerase in a sequencing-by-synthesis reaction, e.g. Metzger, Nature Reviews Genetics, 11: 31-46 (2010); Fuller et al, Nature Biotechnology, 27: 1013-1023 (2009). The binding sites for primers (302) and (310) are predetermined, so that they can provide a starting point or anchoring point for initial alignment and analysis of the sequence reads. In one embodiment, a C read is positioned so that it encompasses the D and/or NDN region of the TCR β or IgH chain and includes a portion of the adjacent V region, e.g. as illustrated in FIGS. 3B and 3C. In one aspect, the overlap of the V read and the C read in the V region is used to align the reads with one another. In other embodiments, such alignment of sequence reads is not necessary, e.g. with TCRβ chains, so that a V read may only be long enough to identify the particular V region of a clonotype. This latter aspect is illustrated in FIG. 3C. Sequence read (330) is used to identify a V region, with or without overlapping another sequence read, and another sequence read (332) traverses the NDN region and is used to determine the sequence thereof. Portion (334) of sequence read (332) that extends into the V region is used to associate the sequence information of sequence read (332) with that of sequence read (330) to determine a clonotype. For some sequencing methods, such as base-by-base approaches like the Solexa sequencing method, sequencing run time and reagent costs are reduced by minimizing the number of sequencing cycles in an analysis. Optionally, as illustrated in FIG. 3B, amplicon (300) is produced with sample tag (312) to distinguish between clonotypes originating from different biological samples, e.g. different patients. Sample tag (312) may be identified by annealing a primer to primer binding region (316) and extending it (314) to produce a sequence read across tag (312), from which sample tag (312) is decoded.

The IgH chain is more challenging to analyze than TCRβ chain because of at least two factors: i) the presence of somatic mutations makes the mapping or alignment more difficult, and ii) the NDN region is larger so that it is often not possible to map a portion of the V segment to the C read. In one aspect of the invention, this problem is overcome by using a plurality of primer sets for generating V reads, which are located at different locations along the V region, preferably so that the primer binding sites are nonoverlapping and spaced apart, and with at least one primer binding site adjacent to the NDN region, e.g. in one embodiment from 5 to 50 bases from the V-NDN junction, or in another embodiment from 10 to 50 bases from the V-NDN junction. The redundancy of a plurality of primer sets minimizes the risk of failing to detect a clonotype due to a failure of one or two primers having binding sites affected by somatic mutations. In addition, the presence of at least one primer binding site adjacent to the NDN region makes it more likely that a V read will overlap with the C read and hence effectively extend the length of the C read. This allows for the generation of a continuous sequence that spans all sizes of NDN regions and that can also map substantially the entire V and J regions on both sides of the NDN region. Embodiments for carrying out such a scheme are illustrated in FIGS. 4A and 4D. In FIG. 4A, a sample comprising IgH chains (400) are sequenced by generating a plurality amplicons for each chain by amplifying the chains with a single set of J region primers (401) and a plurality (three shown) of sets of V region (402) primers (404, 406, 408) to produce a plurality of nested amplicons (e.g., 410, 412, 416) all comprising the same NDN region and having different lengths encompassing successively larger portions (411, 413, 415) of V region (402). Members of a nested set may be grouped together after sequencing by noting the identify (or substantial identity) of their respective NDN, J and/or C regions, thereby allowing reconstruction of a longer V(D)J segment than would be the case otherwise for a sequencing platform with limited read length and/or sequence quality. In one embodiment, the plurality of primer sets may be a number in the range of from 2 to 5. In another embodiment the plurality is 2-3; and still another embodiment the plurality is 3. The concentrations and positions of the primers in a plurality may vary widely. Concentrations of the V region primers may or may not be the same. In one embodiment, the primer closest to the NDN region has a higher concentration than the other primers of the plurality, e.g. to insure that amplicons containing the NDN region are represented in the resulting amplicon. In a particular embodiment where a plurality of three primers is employed, a concentration ratio of 60:20:20 is used. One or more primers (e.g. 435 and 437 in FIG. 4B) adjacent to the NDN region (444) may be used to generate one or more sequence reads (e.g. 434 and 436) that overlap the sequence read (442) generated by J region primer (432), thereby improving the quality of base calls in overlap region (440). Sequence reads from the plurality of primers may or may not overlap the adjacent downstream primer binding site and/or adjacent downstream sequence read. In one embodiment, sequence reads proximal to the NDN region (e.g. 436 and 438) may be used to identify the particular V region associated with the clonotype. Such a plurality of primers reduces the likelihood of incomplete or failed amplification in case one of the primer binding sites is hypermutated during immunoglobulin development. It also increases the likelihood that diversity introduced by hypermutation of the V region will be capture in a clonotype sequence. A secondary PCR may be performed to prepare the nested amplicons for sequencing, e.g. by amplifying with the P5 (401) and P7 (404, 406, 408) primers as illustrated to produce amplicons (420, 422, and 424), which may be distributed as single molecules on a solid surface, where they are further amplified by bridge PCR, or like technique.

Base calling in NDN regions (particularly of IgH chains) can be improved by using the codon structure of the flanking J and V regions, as illustrated in FIG. 4C. (As used herein, "codon structure" means the codons of the natural reading frame of segments of TCR or BCR transcripts or genes outside of the NDN regions, e.g. the V region, J region, or the like.) There amplicon (450), which is an enlarged view of the amplicon of FIG. 4B, is shown along with the relative positions of C read (442) and adjacent V read (434) above and the codon structures (452 and 454) of V region (430) and J region (446), respectively, below. In accordance with this aspect of the invention, after the codon structures (452 and 454) are identified by conventional alignment to the V and J reference sequences, bases in NDN region (456) are called (or identified) one base at a time moving from J region (446) toward V region (430) and in the opposite direction from V region (430) toward J region (446) using sequence reads (434) and (442). Under normal biological conditions, only the recombined TCR or IgH sequences that have in frame codons from the V region through the NDN region and to the J region are expressed as proteins. That is, of the variants generated somatically only ones expressed are those whose J region and V region codon frames are in-frame with one another and remain in-frame through the NDN region. (Here the correct frames of the V and J regions are determined from reference sequences). If an out-of-frame sequence is identified based one or more low quality base calls, the corresponding clonotype is flagged for re-evaluation or as a potential disease-related anomaly. If the sequence identified is in-frame and based on high quality base calls, then there is greater confidence that the corresponding clonotype has been correctly called. Accordingly, in one aspect, the invention includes a method of determining V(D)J-based clonotypes from bidirectional sequence reads comprising the steps of: (a) generating at least one J region sequence read that begins in a J region and extends into an NDN region and at least one V region sequence read that begins in the V regions and extends toward the NDN region such that the J region sequence read and the V region sequence read are overlapping in an overlap region, and the J region and the V region each have a codon structure; (b) determining whether the codon structure of the J region extended into the NDN region is in frame with the codon structure of the V region extended toward the NDN region. In a further embodiment, the step of generating includes generating at least one V region sequence read that begins in the V region and extends through the NDN region to the J region, such that the J region sequence read and the V region sequence read are overlapping in an overlap region.

Analyzing Sequence Reads. Coalescing sequence reads into clonotypes. Constructing clonotypes from sequence read data depends in part on the sequencing method used to generate such data, as the different methods have different expected read lengths and data quality. In one approach, a Solexa sequencer is employed to generate sequence read data for analysis. In one embodiment, a sample is obtained that provides at least $0.5$-$1.0\times10^6$ lymphocytes to produce at least 1 million template molecules, which after optional amplification may produce a corresponding one million or more clonal populations of template molecules (or clusters). For most high throughput sequencing approaches, including the Solexa approach, such over sampling at the cluster level is desirable so that each template sequence is determined with a large degree of redundancy to increase the accuracy of sequence determination. For Solexa-based implementations, preferably the sequence of each independent template is determined 10 times or more. For other sequencing approaches with different expected read lengths and data quality, different levels of redundancy may be used for comparable accuracy of sequence determination. Those of ordinary skill in the art recognize that the above parameters, e.g. sample size, redundancy, and the like, are design choices related to particular applications.

Reducing a set of reads for a given sample into its distinct clonotypes and recording the number of reads for each clonotype would be a trivial computational problem if sequencing technology was error free. However, in the presence of sequencing errors, each clonotype is surrounded by a 'cloud' of reads with varying numbers of errors with respect to the true clonotype sequence. The higher the number of such errors the smaller the density if the surrounding cloud, i.e. the cloud drops off in density as we move away from the clonotype in sequence space. A variety of algorithms are available for converting sequence reads into clonotypes. In one aspect, coalescing of sequence reads depends on three factors: the number of sequences obtained for each of the two clonotypes of interest; the number of bases at which they differ; and the sequencing quality at the positions at which they are discordant. A likelihood ratio is assessed that is based on the expected error rates and binomial distribution of errors. For example two clonotypes, one with 150 reads and the other with 2 reads with one difference between them in an area of poor sequencing quality will likely be coalesced as they are likely to be generated by sequencing error. On the other hand two clonotypes, one with 100 reads and the other with 50 reads with two differences between them are not coalesced as they are considered to be unlikely to be generated by sequencing error. In one embodiment of the invention, the algorithm described below may be used for determining clonotypes from sequence reads.

This cloud of reads surrounding each clonotype can be modeled using the binomial distribution and a simple model for the probability of a single base error. This latter error model can be inferred from mapping V and J segments or from the clonotype finding algorithm itself, via self-consistency and convergence. A model is constructed for the probability of a given 'cloud' sequence Y with read count C2 and E errors (with respect to sequence X) being part of a true clonotype sequence X with perfect read count C1 under the null model that X is the only true clonotype in this region of sequence space. A decision is made whether or not to coalesce sequence Y into the clonotype X according the parameters C1, C2, and E. For any given C1 and E a max value C2 is pre-calculated for deciding to coalesce the sequence Y. The max values for C2 are chosen so that the probability of failing to coalesce Y under the null hypothesis that Y is part of clonotype X is less than some value P after integrating over all possible sequences Y with error E in the neighborhood of sequence X. The value P is controls the behavior of the algorithm and makes the coalescing more or less permissive.

If a sequence Y is not coalesced into clonotype X because its read count is above the threshold C2 for coalescing into clonotype X then it becomes a candidate for seeding separate clonotypes. The algorithm also makes sure than any other sequences Y2, Y3, etc. which are 'nearer' to this sequence Y (that had been deemed independent of X) are not aggregated into X. This concept of 'nearness' includes both error counts with respect to Y and X and the absolute read count of X and Y, i.e. it is modeled in the same fashion as the above model for the cloud of error sequences around clonotype X. In this way 'cloud' sequences can be properly attributed to their correct clonotype if they happen to be 'near' more than one clonotype.

The algorithm proceeds in a top down fashion by starting with the sequence X with the highest read count. This sequence seeds the first clonotype. Neighboring sequences are either coalesced into this clonotype if their counts are below the precalculated thresholds (see above), or left alone if they are above the threshold or 'closer' to another sequence that was not coalesced. After searching all neighboring sequences within a maximum error count, the process of coalescing reads into clonotype X is finished. Its reads and all reads that have been coalesced into it are accounted for and removed from the list of reads available for making other clonotypes. The next sequence is then moved on to with the highest read count. Neighboring reads are coalesced into this clonotype as above and this process is continued until there are no more sequences with read counts above a given threshold, e.g. until all sequences with more than 1 count have been used as seeds for clonotypes.

In another embodiment of the above algorithm, a further test may be added for determining whether to coalesce a candidate sequence Y into an existing clonotype X, which takes into account quality score of the relevant sequence reads. The average quality score(s) are determined for sequence(s) Y (averaged across all reads with sequence Y) were sequences Y and X differ. If the average score is above a predetermined value then it is more likely that the difference indicates a truly different clonotype that should not be coalesced and if the average score is below such predetermined value then it is more likely that sequence Y is caused by sequencing errors and therefore should be coalesced into X.

Sequence Tree. The above algorithm of coalescing reads into clonotypes is dependent upon having an efficient way of finding all sequences with less than E errors from some input sequence X. This problem is solved using a sequence tree. The implementation of this tree has some unusual features in that the nodes of the tree are not restricted to being single letters of DNA. The nodes can have arbitrarily long sequences. This allows for a more efficient use of computer memory.

All of the reads of a given sample are placed into the sequence tree. Each leaf nodes holds pointers to its associated reads. It corresponds to a unique sequence given by traversing backwards in the tree from the leaf to the root node. The first sequence is placed into a simple tree with one root node and one leaf node that contains the full sequence of the read. Sequences are next added one by one. For each added sequence either a new branch is formed at the last point of common sequence between the read and the existing tree or add the read to an existing leaf node if the tree already contains the sequence.

Having placed all the reads into the tree it is easy to use the tree for the following purposes: 1. Highest read count: Sorting leaf nodes by read count allows us to find the leaf node (i.e. sequence) with the most reads. 2. Finding neighboring leafs: for any sequence all paths through the tree which have less than X errors with respect to this sequence are searchable. A path is started at the root and branch this path into separate paths proceeding along the tree. The current error count of each path as proceeding along the tree is noted. When the error count exceeds the max allowed errors the given path is terminated. In this way large parts of the tree are pruned as early as possible. This is an efficient way of finding all paths (i.e. all leafs) within X errors from any given sequence.

Somatic Hypermutations. In one embodiment, IgH-based clonotypes that have undergone somatic hypermutation are determined as follows. A somatic mutation is defined as a sequenced base that is different from the corresponding base of a reference sequence (of the relevant segment, usually V, J or C) and that is present in a statistically significant number of reads. In one embodiment, C reads may be used to find somatic mutations with respect to the mapped J segment and likewise V reads for the V segment. Only pieces of the C and V reads are used that were either directly mapped to J or V segments or that were inside the clonotype extension up to the NDN boundary. In this way, the NDN region is avoided and the same 'sequence information' is not used for mutation finding that was previously used for clonotype determination (to avoid erroneously classifying as mutations nucleotides that are really just different recombined NDN regions). For each segment type, the mapped segment (major allele) is used as a scaffold and all reads are considered which have mapped to this allele during the read mapping phase. Each position of the reference sequences where at least one read has mapped is analyzed for somatic mutations. In one embodiment, the criteria for accepting a non-reference base as a valid mutation include the following: 1) at least N reads with the given mutation base, 2) at least a given fraction N/M reads (where M is the total number of mapped reads at this base position) and 3) a statistical cut based on the binomial distribution, the average Q score of the N reads at the mutation base as well as the number (M–N) of reads with a non-mutation base. Preferably, the above parameters are selected so that the false discovery rate of mutations per clonotype is less than t in 1000, and more preferably, less than 1 in 10000.

Phylogenic Clonotypes (Clans). In cancers, such as lymphoid neoplasms, a single lymphocyte progenitor may give rise to many related lymphocyte progeny, each possessing and/or expressing a slightly different TCR or BCR, and therefore a different clonotype, due to cancer-related somatic mutation(s), such as base substitutions, aberrant rearrangements, or the like. Cells producing such clonotypes are referred to herein as phylogenic clones, and a set of such related clones are referred to herein as a "clan." Likewise, clonotypes of phylogenic clones are referred to as phylogenic clonotypes and a set of phylogenic clonotypes may be referred to as a clan of clonotypes. In one aspect, methods of the invention comprise monitoring the frequency of a clan of clonotypes (i.e., the sum of frequencies of the constituent phylogenic clonotypes of the clan), rather than a frequency of an individual clonotype. Phylogenic clonotypes may be identified by one or more measures of relatedness to a parent clonotype. In one embodiment, phylogenic clonotypes may be grouped into the same clan by percent homology, as described more fully below. In another embodiment, phylogenic clonotypes are identified by common usage of V regions, J regions, and/or NDN regions. For example, a clan may be defined by clonotypes having common J and ND regions but different V regions; or it may be defined by clonotypes having the same V and J regions (including identical base substitutions mutations) but with different NDN regions; or it may be defined by a clonotype that has undergone one or more insertions and/or deletions of from 1-10 bases, or from 1-5 bases, or from 1-3 bases, to generate clan members. In another embodiment, members of a clan are determined as follows. Clonotypes are assigned to the same clan if they satisfy the following criteria: i) they are mapped to the same V and J reference segments, with the mappings occurring at the same relative positions in the clonotype sequence, and ii) their NDN regions are substantially identical. "Substantial" in reference to clan membership means that some small differences in the NDN region are allowed because somatic mutations may have occurred in this region. Preferably, in one embodiment, to avoid falsely calling a mutation in the NDN region, whether a base substitution is accepted as a cancer-related mutation depends directly on the size of the NDN region of the clan. For example, a method may accept a clonotype as a clan member if it has a one-base difference from clan NDN sequence(s) as a cancer-related mutation if the length of the clan NDN sequence(s) is m nucleotides or greater, e.g. 9 nucleotides or greater, otherwise it is not accepted, or if it has a two-base difference from clan NDN sequence(s) as cancer-related mutations if the length of the clan NDN sequence(s) is n nucleotides or greater, e.g. 20 nucleotides or greater, otherwise it is not accepted. In another embodiment, members of a clan are determined using the following criteria: (a) V read maps to the same V region, (b) C read maps to the same J region, (c) NDN region substantially identical (as described above), and (d) position of NDN region between V-NDN boundary and J-NDN boundary is the same (or equivalently, the number of downstream base additions to D and the number of upstream base additions to D are the same). Clonotypes of a single sample may be grouped into clans and clans from successive samples acquired at different times may be compared with one another. In particular, in one aspect of the invention, clans containing clonotypes correlated with a disease, such as a lymphoid neoplasm, are identified from clonotypes of each sample and compared with that of the immediately previous sample to determine disease status, such as, continued remission, incipient relapse, evidence of further clonal evolution, or the like.

It is expected that PCR error is concentrated in some bases that were mutated in the early cycles of PCR. Sequencing error is expected to be distributed in many bases even though it is totally random as the error is likely to have some systematic biases. It is assumed that some bases will have sequencing error at a higher rate, say 5% (5 fold the average). Given these assumptions, sequencing error becomes the dominant type of error. Distinguish PCR errors from the occurrence of highly related clonotypes will play a role in analysis. Given the biological significance to determining that there are two or more highly related clonotypes, a conservative approach to making such calls is taken. The detection of enough of the minor clonotypes so as to be sure with high confidence (say 99.9%) that there are more than one clonotype is considered. For example of clonotypes that are present at 100 copies/1,000,000, the minor variant is detected 14 or more times for it to be designated as an independent clonotype. Similarly, for clonotypes present at 1,000 copies/1,000,000 the minor variant can be detected 74 or more times to be designated as an independent clonotype. This algorithm can be enhanced by using the base quality score that is obtained with each sequenced base. If the relationship between quality score and error rate is validated above, then instead of employing the conservative 5% error rate for all bases, the quality score can be used to decide the number of reads that need to be present to call an independent clonotype. The median quality score of the specific base in all the reads can be used, or more rigorously, the likelihood of being an error can be computed given the quality score of the specific base in each read, and then the probabilities can be combined (assuming independence) to estimate the likely number of sequencing error for that base. As a result, there are different thresholds of rejecting the sequencing error hypothesis for different bases with different quality scores. For example for a clonotype present at 1,000 copies/1,000,000 the minor variant is designated independent when it is detected 22 and 74 times if the probability of error were 0.01 and 0.05, respectively.

Kits

In the commercialization of the methods described herein, kits for amplification of specific somatically rearranged regions or portions thereof are particularly useful. Such kits may be for carrying out one or two staged PCRs (as described above) for amplifying a predetermined somatically rearranged region or portion thereof for the purpose of preparing a sample of clonotypes for sequence analysis. A kit typically comprises one or more reagents, such as, without limitation, nucleic acid primers, packaged in a container, such as, without limitation, a vial, tube or bottle, in a package suitable for commercial distribution, such as, without limitation, a box, a sealed pouch, a blister pack or a carton.

The package typically contains a label or packaging insert indicating that the packaged reagents can be used in a method for generating a clonotype profile from a tissue sample of a patient. As used herein, "packaging materials" includes any article used in the packaging for distribution of reagents in a kit, including without limitation containers, vials, tubes, bottles, pouches, blister packaging, labels, tags, instruction sheets and package inserts. One example of such a kit includes reagents necessary for the amplification in one tube of TCRβ sequences from DNA or RNA extracted T cells of a patient or peripheral blood lymphocytes of a patient or bone marrow of a patient, as described above. Another example of such a kit includes reagents necessary for the amplification in a plurality of tubes IgH sequences from DNA or RNA extracted B cells of a patient or peripheral blood lymphocytes of a patient or bone marrow of a patient, as described above. In the latter example, necessary reagents include a plurality of sets of primers for generating nested sets of templates, as described above. Typically, such plurality is 2 or 3 or 4. For the latter example, in one embodiment, three sets of primers are provided; and more specifically, the following three sets of primers are provided: set 1 comprising forward primers from Table 5 and reverse primers from Table 8; set 2 comprising forward primers from Table 6 and reverse primers from Table 8; set 3 comprising forward primers from Table 7 and reverse primers from Table 8. In another example, the kit would include the above-described reagents, including one or more PCR primer sets and a thermostable DNA polymerase, such as Taq polymerase, and if sequences are amplified from RNA, a reverse transcriptase. The primers may be present in quantities that would yield a balanced amplification of individual clonotype sequences in a patient sample, as described above. In one aspect of the invention, quantities of primers are provided to ensure a balanced amplification of clonotypes. Such balancing of multiplex PCRs is well known by practitioners of ordinary skill in the art and includes, but is not limited to, adjusting the concentrations of primers in the reaction and/or selecting the positions and lengths of primers in a region of interest to increase or decrease the rate of annealing of individual primers. In one embodiment, the quantities of primers are selected so that in the PCR their concentrations are such that the rate at which each primer anneals to its primer binding site is substantially identical. In another embodiment, quantities of primers are selected so that each sequence in a sample is amplified to an amount that is within 2-fold of the average amplification amount of a random sample of clonotypes. In still another embodiment, such random sample contains at least 100 clonotypes.

Thermostable DNA polymerases and transcriptases are commercially available from a variety of manufacturers. Additional materials in the kit may include: suitable reaction tubes or vials, a barrier composition, typically a wax bead, optionally including magnesium; reaction mixtures (often concentrated, for example 2×, 5×, 10× or 20×) for the PCR stages, including necessary buffers and reagents such as dNTPs; nuclease- or RNase-free water; RNase inhibitor; control nucleic acid(s) (i.e. such as internal standards), and/or any additional buffers, compounds, co-factors, ionic constituents, proteins and enzymes, polymers, and the like that may be used in multiplex PCR reactions.

Components of a kit are packaged in any manner that is commercially practicable. For example, PCR primers and/or reverse transcriptase may be packaged individually to facilitate flexibility in configuring the assay, or together to increase case of use and to reduce contamination. Similarly, buffers, salts and co-factors can be packaged separately or together. The kits also may include reagents and mechanical components suitable for the manual or automated extraction of nucleic acid from a tissue sample. These reagents are known to those skilled in the art and typically are a matter of design choice. For instance, in one embodiment of an automated process, tissue is disrupted ultrasonically in a suitable lysis solution provided in the kit.

EXAMPLE 1

TCRβ Repertoire Analysis: Amplification and Sequencing Strategy

In this example, TCRβ chains are analyzed. The analysis includes amplification, sequencing, and analyzing the TCRβ sequences. One primer AGCGACCTCGGGTGGGAACA (SEQ ID NO: 1) is complementary to a common sequence in Cβ1 and Cβ2, and there are 34 V primers (Table 1) capable of amplifying all 48 V segments. Cβ1 or Cβ2 differ from each other at position 10 and 14 from the J/C junction. The primer for Cβ1 and Cβ2 ends at position 16 bp and has no preference for Cβ1 or Cβ2.

The 34 V primers are modified from an original set of primers disclosed in Van Dongen et al, U.S. patent publication 2006/0234234, which is incorporated herein by reference.

TABLE 1

Primer sequences complementary to the different V families.

| V segment family | Primer Sequence | SEQ ID NO |
|---|---|---|
| V20-1 | AACTATGTTTTGGTATCGTCAGT | 2 |
| V29-1 | TTCTGGTACCGTCAGCAAC | 3 |
| V9, 5-1, 5-6, 5-5, 5-8, 5-4A | AGTGTATCCTGGTACCAACAG | 4 |
| V9, 5-1, 5-6, 5-5, 5-8, 5-4B | AGTGTGTACTGGTACCAACAG | 5 |
| V9, 5-1, 5-6, 5-5, 5-8, 5-4C | ACTGTGTCCTGGTACCAACAG | 6 |
| V9, 5-1, 5-6, 5-5, 5-8, 5-4D | AGTGTGTCCTGGTACCAACAG | 7 |
| V9, 5-1, 5-6, 5-5, 5-8, 5-4E | TCTGTGTACTGGTACCAACAG | 8 |
| V7-3, 7-6, 7-9, 7-2, 7-4A | CCCTTTACTGGTACCGACAG | 9 |
| V7-3, 7-6, 7-9, 7-2, 7-4B | GCCTTTACTGGTACCGACAG | 10 |
| V7-3, 7-6, 7-9, 7-2, 7-4C | CCCTTTACTGGTACCGACAAA | 11 |
| V7-8, 16A | TTTTGGTACCAACAGGTCC | 12 |
| V7-8, 16B | TTTTGGTACCAACAGGCCC | 13 |
| V 7-7 | AACCCTTTATTGGTATCAACAG | 14 |
| V4-1, 4-3, 4-2A | CGCTATGTATTGGTACAAGCA | 15 |
| V4-1, 4-3, 4-2B | CGCTATGTATTGGTACAAGCA | 16 |

TABLE 1-continued

Primer sequences complementary to the different V families.

| V segment family | Primer Sequence | SEQ ID NO |
|---|---|---|
| V12-3, 12-4, 12-5 | TTTCTGGTACAGACAGACCATGA | 17 |
| V3-1 | TACTATGTATTGGTATAAACAGGACTC | 18 |
| V25-1 | CAAAATGTACTGGTATCAACAA | 19 |
| V28, 10-3, 6-2, 6-3, 6-1, 6-6, 24-1A | CAAAATGTACTGGTATCAACAA | 20 |
| V28, 10-3, 6-2, 6-3, 6-1, 6-6, 24-1B | ATGTACTGGTATCGACAAGACC | 21 |
| V6-4, 6-9A | TGCCATGTACTGGTATAGACAAG | 22 |
| V6-4, 6-9B | ATACTTGTCCTGGTATCGACAAG | 23 |
| V10-1, 10-2, 6-5, 6-9, 6-8, 27A | ATATGTTCTGGTATCGACAAGA | 24 |
| V10-1, 10-2, 6-5, 6-9, 6-8, 27B | ATATGTCCTGGTATCGACAAGA | 25 |
| V10-1, 10-2, 6-5, 6-9, 6-8, 27C | ACATGTCCTGGTATCGACAAGA | 26 |
| V14 | TAATCTTTATTGGTATCGACGTGT | 27 |
| V19 | GCCATGTACTGGTACCGACA | 28 |
| V18 | TCATGTTTACTGGTATCGGCAG | 29 |
| V30 | CAACCTATACTGGTACCGACA | 30 |
| V11-1, 11-3, 11-2A | CATGCTACCCTTTACTGGTACC | 31 |
| V11-1, 11-3, 11-2B | CACAATACCCTTTACTGGTACC | 32 |
| V2 | ATACTTCTATTGGTACAGACAAATCT | 33 |
| V13 | CACTGTCTACTGGTACCAGCA | 34 |
| V15 | CGTCATGTACTGGTACCAGCA | 35 |

The Illumina Genome Analyzer is used to sequence the amplicon produced by the above primers. A two-stage amplification is performed on messenger RNA transcripts (200), as illustrated in FIGS. 2A-2B, the first stage employing the above primers and a second stage to add common primers for bridge amplification and sequencing. As shown in FIG. 2A, a primary PCR is performed using on one side a 20 bp primer (202) whose 3' end is 16 bases from the J/C junction (204) and which is perfectly complementary to Cβ1 (203) and the two alleles of Cβ2. In the V region (206) of RNA transcripts (200), primer set (212) is provided which contains primer sequences complementary to the different V region sequences (34 in one embodiment). Primers of set (212) also contain a non-complementary tail (214) that produces amplicon (216) having primer binding site (218) specific for P7 primers (220). After a conventional multiplex PCR, amplicon (216) is formed that contains the highly diverse portion of the J(D)V region (206, 208, and 210) of the mRNA transcripts and common primer binding sites (203 and 218) for a secondary amplification to add a sample tag (221) and primers (220 and 222) for cluster formation by bridge PCR. In the secondary PCR, on the same side of the template, a primer (222 in FIG. 2B and referred to herein as "C10-17-P5") is used that has at its 3'end the sequence of the 10 bases closest to the J/C junction, followed by 17 bp with the sequence of positions 15-31 from the J/C junction, followed by the P5 sequence (224), which plays a role in cluster formation by bridge PCR in Solexa sequencing. (When the C10-17-P5 primer (222) anneals to the template generated from the first PCR, a 4 bp loop (position 11-14) is created in the template, as the primer hybridizes to the sequence of the 10 bases closest to the J/C junction and bases at positions 15-31 from the J/C junction. The looping of positions 11-14 eliminates differential amplification of templates carrying Cβ1 or Cβ2. Sequencing is then done with a primer complementary to the sequence of the 10 bases closest to the J/C junction and bases at positions 15-31 from the J/C junction (this primer is called C'). C10-17-P5 primer can be HPLC purified in order to ensure that all the amplified material has intact ends that can be efficiently utilized in the cluster formation.)

In FIG. 2A, the length of the overhang on the V primers (212) is preferably 14 bp. The primary PCR is helped with a shorter overhang (214). Alternatively, for the sake of the secondary PCR, the overhang in the V primer is used in the primary PCR as long as possible because the secondary PCR is priming from this sequence. A minimum size of overhang (214) that supports an efficient secondary PCR was investigated. Two series of V primers (for two different V segments) with overhang sizes from 10 to 30 with 2 bp steps were made. Using the appropriate synthetic sequences, the first PCR was performed with each of the primers in the series and gel electrophoresis was performed to show that all amplified. In order to measure the efficiency of the second PCR amplification SYBR green real time PCR was performed using as a template the PCR products from the different first PCR reactions and as primers Read2-tag1-P7 and Read2-tag2-P7. A consistent picture emerged using all 4 series of real time data (2 primary PCRs with two different V segments and two secondary PCR with different primers containing two different tags). There was an improvement in efficiency between overhang sizes 10 and 14 bp. However there was little or no improvement in efficiency with an overhang over 14 bp. The efficiency remained high as the overhang became as small as 14 bp because of the high concentration of primers allowing the 14 bp to be sufficient priming template at a temperature much higher than their melting temperature. At the same time the specificity was maintained because the template was not all the cDNA but rather a low complexity PCR product where all the molecules had the 14 bp overhang.

As illustrated in FIG. 2A, the primary PCR uses 34 different V primers (212) that anneal to V region (206) of RNA templates (200) and contain a common 14 bp overhang on the 5' tail. The 14 bp is the partial sequence of one of the Illumina sequencing primers (termed the Read 2 primer). The secondary amplification primer (220) on the same side includes P7 sequence, a tag (221), and Read 2 primer sequence (223) (this primer is called Read2_tagX_P7). The P7 sequence is used for cluster formation. Read 2 primer and its complement are used for sequencing the V segment and the tag respectively. A set of 96 of these primers with tags numbered 1 through 96 are created (see below). These primers are HPLC purified in order to ensure that all the amplified material has intact ends that can be efficiently utilized in the cluster formation.

As mentioned above, the second stage primer, C-10-17-P5 (222, FIG. 2B) has interrupted homology to the template generated in the first stage PCR. The efficiency of amplification using this primer has been validated. An alternative primer to C-10-17-P5, termed CsegP5, has perfect homology to the first stage C primer and a 5' tail carrying P5. The efficiency of using C-10-17-P5 and CsegP5 in amplifying first stage PCR templates was compared by performing real time PCR. In several replicates, it was found that PCR using the C-10-17-P5 primer had little or no difference in efficiency compared with PCR using the CsegP5 primer.

Amplicon (300) resulting from the 2-stage amplification illustrated in FIGS. 2A-2B has the structure typically used with the Illumina sequencer as shown in FIG. 3A. Two primers that anneal to the outmost part of the molecule, Illumina primers P5 (AATGATACGGCGACCACCGAG) (SEQ ID NO: 36) and P7 (CAAGCAGAAGACGGCATACGAGAT) (SEQ ID NO: 37) are used for solid phase amplification of the Molecule (cluster formation). Three sequence reads are done per molecule. The first read of 100 bp is done with the C' primer, which has a melting temperature that is appropriate for the Illumina sequencing process. The second read is 6 bp long only and is solely for the purpose of identifying the sample tag. It is generated using the Illumina Tag primer (AGATCGGAAGAGCACACGTCTGAACTCCAGTCAC) (SEQ ID NO: 38). The final read is the Read 2 primer, an Illumina primer with the sequence GTGACTGGAGTTCAGACGTGTGCTCTTCCGATCT (SEQ ID NO: 39). Using this primer, a 100 bp read in the V segment is generated starting with the 1st PCR V primer sequence.

A set of 6 bp sequence tags to distinguish different samples run in the same sequencing lane was designed, where each tag is different from all the other tags in the set by at least 2 differences. The 2 differences prevent misassignment of a read to the wrong sample if there is a sequencing error. The alignment done to compare the tags allowed gaps and hence one deletion or insertion error by sequencing will also not assign the read to the wrong sample. Additional features in selecting the tags was to limit single base runs (4 A or T and 3 G or C) as well as no similarity to the Illumina primers. In total 143 tags were generated, 96 of them are used.

Sequencing TCRβ. Six multiplexed amplifications with the pooled oligos and one cDNA sample as a template were used. Three of each of the amplifications were done with Accuprime and another three with high fidelity Taq. Two amplifications with each enzyme used cDNA that correspond to 500 ng initial RNA, and one amplification with each enzyme used 10 times less cDNA. For each of the six reactions a primary and secondary PCR was performed and the amplified material was sequenced using the Illumina platform and the scheme described above. 100 bp sequence from each side was obtained. The primary analysis of the data was done using the same concepts described below.

To assess reproducibility of the assay it was determined whether clonotype levels are consistent in the duplicate experiments. As shown in FIGS. 5A-5C, high correlation is obtained when the same enzyme and starting input cDNA amount was used (each of the 2 comparisons had r2=0.944). When different enzymes were used the correlation gets worse (median correlation for the 4 possible combinations r2=0.931), and it is only modestly reduced (r2=0.924) when the 2 enzymes were used to amplify smaller input cDNA (corresponding to only 50 ng RNA).

Figure 7C:
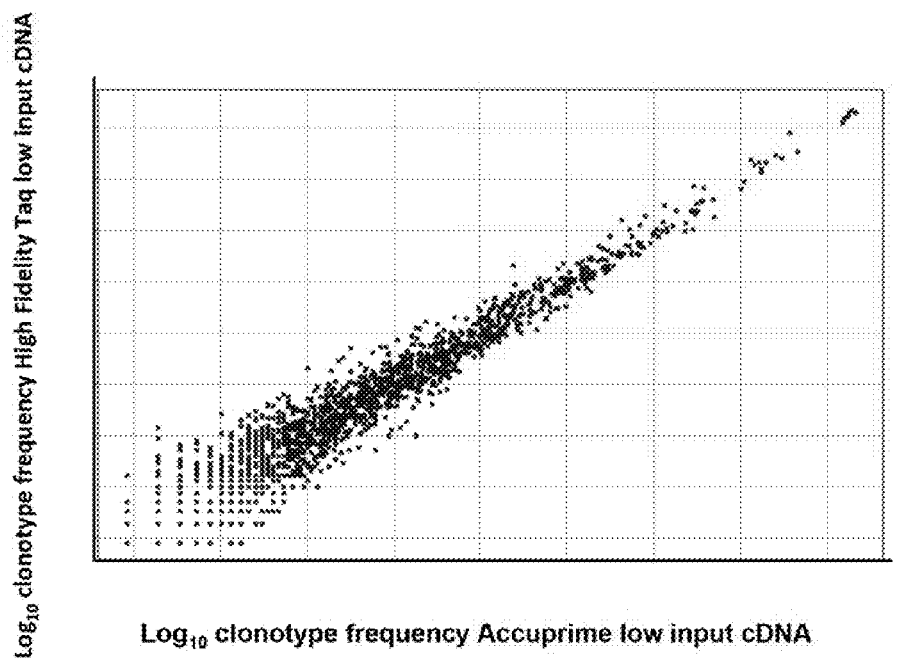
FIG. 7C shows the log 10 of the frequency of each clonotype using cDNA corresponding to 50 ng of RNA as input template and Accuprime (X axis) or High fidelity Taq (Y axis).
Figure 7A:
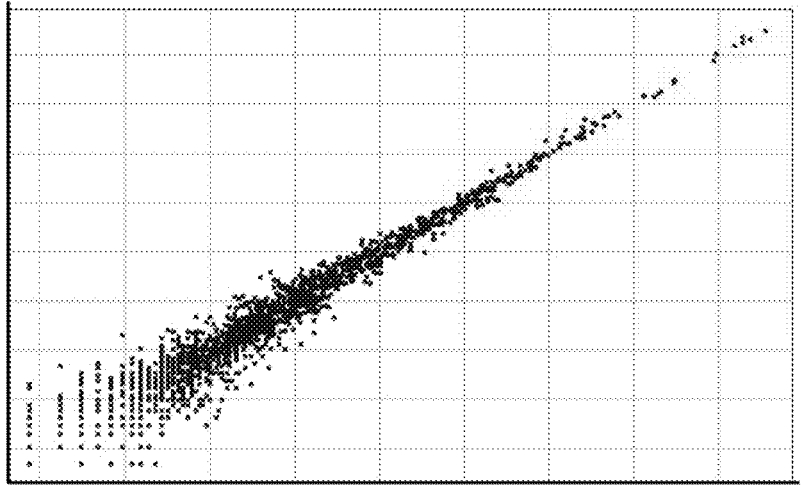
FIG. 7A shows the log 10 of the frequency of each clonotype in the two duplicate samples using Accuprime and cDNA corresponding to 500 ng of RNA as input template.
Figure 7B:
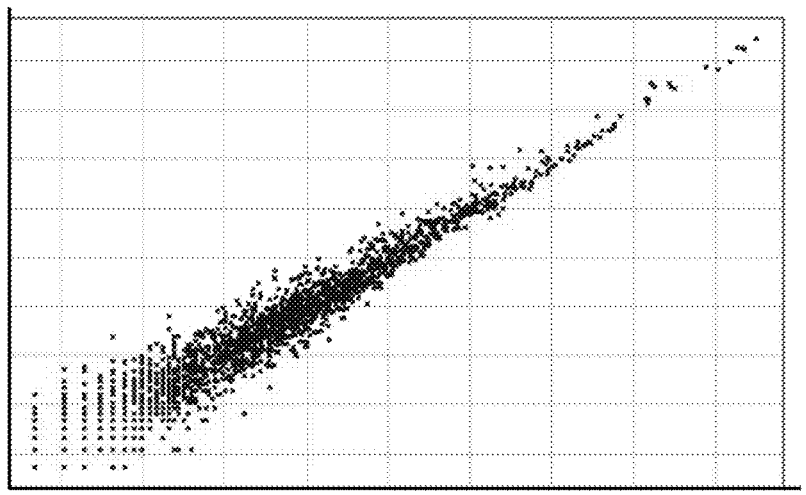
FIG. 7B depicts the log 10 of the frequency of each clonotype using cDNA corresponding to 500 ng of RNA as input template and Accuprime (X axis) or High fidelity Taq (Y axis).

In FIGS. 5A-5C, identical sequences in each sample were identified. Then to deal with sequencing errors some clonotypes were coalesced to form larger clonotypes using the general approaches described in the section of primary analysis of sequence. The counts of clonotypes were then computed in each sample. A fraction of the clonotypes (not shown in the figure) were present in one sample but not another, likely due to the algorithm coalescing them with another clonotype in one sample but not the other. The frequency of clonotypes in a sample is then computed as its number of counts divided by the total number of reads obtained for that sample. For example if 1,000 counts are observed for a clonotype in a sample with 1,000,000 reads, its frequency is computed as 0.1%. FIG. 7A shows the $\log_{10}$ of the frequency of each clonotype in the two duplicate samples using Accuprime and cDNA corresponding to 500 ng of RNA as input template. The correlation ($r^2$) between these duplicates is 0.944. FIG. 7B depicts the $\log_{10}$ of the frequency of each clonotype using cDNA corresponding to 500 ng of RNA as input template and Accuprime (X axis) or High fidelity Taq (Y axis). There are 4 comparisons with this combination with a median correlation $r^2$=0.931. The one shown in the figure has $r^2$=0.929. FIG. 7C shows the $\log_{10}$ of the frequency of each clonotype using cDNA corresponding to 50 ng of RNA as input template and Accuprime (X axis) or High fidelity Taq (Y axis). The observed correlation r2=0.924.

EXAMPLE 2

IgH Repertoire Analysis: Amplification and Sequencing Strategy

In this example, three primers are used to amplify V regions of IgH molecules. Preferably, the primers are in regions avoiding the CDRs, which have the highest frequency of somatic mutations. Three different amplification reactions are performed. In each reaction, each of the V segments is amplified by one of the three primers and all will use the same C segment primers. The primers in each of the separate reactions are approximately the same distance from the V-D joint and different distances with respect to the primers in different reactions, so that the primers of the three reactions are spaced apart along the V segment. Assuming the last position of the V segment as 0, then the first set of primers (frame A) have the 3' end at approximately −255, the second set (frame B) have the 3' end at approximately −160, and the third set (frame C) have the 3' end at approximately −30. Given the homology between several V segments, to amplify all the 48 V segments and the many known alleles (as defined by the international ImMunoGeneTics information system <<http://img1.cines.fr/>>) 23, 33, and 32 primers in the A, B, and C frames respectively, is needed. The list of primers are shown in Tables 2, 3, and 4.

TABLE 2

Frame A Primers

| Segment | Sequence | SEQ ID NO |
|---|---|---|
| IGHV1_1 | CCTCAGTGAAGGTCTCCTGCAAGG | 40 |
| IGHV1_2 | CCTCGGTGAAGGTCTCCTGCAAGG | 41 |
| IGHV1_3 | CCTCAGTGAAGGTTTCCTGCAAGG | 42 |
| IGHV1_4 | GGGCTACAGTGAAAATCTCCTGCAAGG | 43 |
| IGHV2_1 | AAACCCACACAGACCCTCACGCTGAC | 44 |
| IGHV2_2 | AAACCCACAGAGACCCTCACGCTGAC | 45 |
| IGHV2_3 | AAACCCACACAGACCCTCACACTGAC | 46 |
| IGHV3_1 | CTGGGGGGTCCCTGAGACTCTCCTG | 47 |
| IGHV3_2 | CTGGGGGGTCCCTTAGACTCTCCTG | 48 |
| IGHV3_3 | CAGGGCGGTCCCTGAGACTCTCCTG | 49 |
| IGHV3_4 | CAGGGCCGTCCCTGAGACTCTCCTG | 50 |

TABLE 2-continued

Frame A Primers

| Segment | Sequence | SEQ ID NO |
|---|---|---|
| IGHV3_5 | CTGGGGGGTCCCTGAAACTCTCCTG | 51 |
| IGHV3_6 | CTGGCAGGTCCCTGAGACTCTCCTG | 52 |
| IGHV3_7 | CTGGAGGGTCCCTGAGACTCTCCTG | 53 |
| IGHV3_8 | CTGGGAGGTCCCTGAGACTCTCCTG | 54 |
| IGHV3_9 | TGGGGGGGCCCTGAGACTCTCCT | 55 |
| IGHV4_1 | CTTCGGAGACCCTGTCCCTCACCTG | 56 |
| IGHV4_2 | CTTCGGACACCCTGTCCCTCACCTG | 57 |
| IGHV4_3 | CTTCACAGACCCTGTCCCTCACCTG | 58 |
| IGHV4_4 | CTTCGGAGACCCCGTCCCTCACCTG | 59 |
| IGHV4_5 | CGGGGACCCTGTCCCTCACCTG | 60 |
| IGHV5_1 | GATCTCCTGTAAGGGTTCTGGATACAGCT | 61 |
| IGHV6 | TCGCAGACCCTCTCACTCACCTGTG | 62 |

TABLE 3

Frame B Primers

| Segment | Sequence | SEQ ID NO |
|---|---|---|
| IGHV6 | TGGATCAGGCAGTCCCCATCGAGAG | 63 |
| IGHV5_1 | GCTGGGTGCGCCAGATGCCC | 64 |
| IGHV2_1 | TGGATCCGTCAGCCCCCAGG | 65 |
| IGHV2_2 | TGGATCCGTCAGCCCCCGGG | 66 |
| IGHV1_1 | GTGCGACAGGCCCCTGGACAA | 67 |
| IGHV1_2 | GGGTGCGACAGGCCACTGGACAA | 68 |
| IGHV1_3 | GTGCGCCAGGCCCCCGGACAA | 69 |
| IGHV1_4 | GGGTGCGACAGGCTCGTGGACAA | 70 |
| IGHV1_5 | GGGTGCAACAGGCCCCTGGAAAA | 71 |
| IGHV1_6 | GGGTGCGACAGGCTCCTGAAAA | 72 |
| IGHV1_7 | GTGCGACAGGCCCCCGGACAA | 73 |
| IGHV1_8 | GTGCGACAGGCCCCCAGACAA | 74 |
| IGHV4_1 | TCCGCCAGCCCCCAGGGAAGG | 75 |
| IGHV4_2 | TCCGGCAGCCCCCAGGGAAGG | 76 |
| IGHV4_3 | TCCGGCAGCCACCAGGGAAGG | 77 |
| IGHV4_4 | TCCGCCAGCACCCAGGGAAGG | 78 |
| IGHV4_5 | TCCGGCAGCCCGCCGGGAA | 79 |
| IGHV4_6 | TCCGGCAGCCGCCGGGAA | 80 |
| IGHV4_7 | TCCGGCAGCCCGCTGGGAAGG | 81 |
| IGHV4_8 | TCCGCCAGCCCCTAGGGAAGG | 82 |
| IGHV3_1 | GGTCCGCCAGGCTCCAGGGAA | 83 |

TABLE 3-continued

Frame B Primers

| Segment | Sequence | SEQ ID NO |
|---|---|---|
| IGHV3_2 | GTTCCGCCAGGCTCCAGGGAA | 84 |
| IGHV3_3 | GGTCCGCCAGGCTTCCGGGAA | 85 |
| IGHV3_4 | GGTCCGTCAAGCTCCGGGGAA | 86 |
| IGHV3_5 | GATCCGCCAGGCTCCAGGGAA | 87 |
| IGHV3_6 | GGTCCGCCAAGCTCCAGGGAA | 88 |
| IGHV3_7 | GGTCCGCCAGGCTCCAGGCAA | 89 |
| IGHV3_8 | GGTCCGCCAGGCTCCAGGCAA | 90 |
| IGHV3_9 | GGTCCGCCAGGCTCCGGGCAA | 91 |
| IGHV3_10 | GGGTCCGTCAAGCTCCAGGGAAGG | 92 |
| IGHV3_11 | CTGGGTCCGCCAAGCTACAGGAAA | 93 |
| IGHV3_12 | GGTCCGCCAGCCTCCAGGGAA | 94 |
| IGHV3_13 | GGTCCGGCAAGCTCCAGGGAA | 95 |

TABLE 4

Frame C Primers

| Segment | Sequence | SEQ ID NO |
|---|---|---|
| IGHV7 | CTAAAGGCTGAGGACACTGCCGTGT | 96 |
| IGHV6 | CTCTGTGACTCCCGAGGACACGGCT | 97 |
| IGHV5_1 | AGTGGAGCAGCCTGAAGGCCTC | 98 |
| IGHV2_1 | TGACCAACATGGACCCTGTGGACAC | 99 |
| IGHV1_1 | ACATGGAGCTGAGCAGCCTGAGATC | 100 |
| IGHV1_2 | ACATGGAGCTGAGCAGGCTGAGATC | 101 |
| IGHV1_3 | ACATGGAGCTGAGGAGCCTGAGATC | 102 |
| IGHV1_4 | ACATGGAGCTGAGGAGCCTAAGATCTGA | 103 |
| IGHV4_1 | GAGCTCTGTGACCGCCGCGGAC | 104 |
| IGHV4_2 | GAGCTCTGTGACCGCCGTGGACA | 105 |
| IGHV4_3 | GAGCTCTGTGACCGCTGCAGACACG | 106 |
| IGHV4_4 | GAGCTCTGTGACCGCTGCGGACA | 107 |
| IGHV4_5 | GAGCTCTGTGACTGCCGCAGACACG | 108 |
| IGHV4_6 | GAGCTCTGTGACTGCAGCAGACACG | 109 |
| IGHV4_7 | GAGCTCTGTGACTGCCGCGGACA | 110 |
| IGHV4_8 | GAGCTCTGTGACCGCGGACGCG | 111 |
| IGHV4_9 | GGCTCTGTGACCGCCGCGGAC | 112 |
| IGHV4_10 | GAGCTCTGTGACCGCCGCAGACA | 113 |
| IGHV4_11 | GAGCTCTGTGACCGCTGACACGG | 114 |
| IGHV3_1 | CAAATGAACAGCCTGAGAGCCGAGGACA | 115 |
| IGHV3_2 | CAAATGAACAGCCTGAAAACCGAGGACA | 116 |
| IGHV3_3 | CAAATGAACAGTCTGAAAACCGAGGACA | 117 |

TABLE 4-continued

Frame C Primers

| Segment | Sequence | SEQ ID NO |
|---|---|---|
| IGHV3_4 | CAAATGATCAGCCTGAAAACCGAGGACA | 118 |
| IGHV3_5 | CAAATGAACAGTCTGAGAACTGAGGACACC | 119 |
| IGHV3_6 | CAAATGAACAGTCTGAGAGCCGAGGACA | 120 |
| IGHV3_7 | CAAATGAACAGCCTGAGAGCTGAGGACA | 121 |
| IGHV3_8 | CAAATGAGCAGCCTGAGAGCTGAGGACA | 122 |
| IGHV3_9 | CAAATGAACAGCCTGAGAGACGAGGACA | 123 |
| IGHV3_10 | CAAATGGGCAGCCTGAGAGCTGAGGACA | 124 |
| IGHV3_11 | CAAATGAACAGCCTGAGAGCCGGGGA | 125 |
| IGHV3_12 | CAAATGAACAGTCTGAGAGCTGAGGACA | 126 |
| IGHV3_13 | CAAATGAGCAGTCTGAGAGCTGAGGACA | 127 |

On the C segment side, two sequences with one base difference between them (GCCAGGGGGAAGACCGATGG (SEQ ID NO: 128), and GCCAGGGGGAAGACGGATGG) (SEQ ID NO: 129) cover the four segments and the multiple known alleles of IgG. A scheme similar to the two stages of PCR for TCRβ genes is used.

On the V side, the same 5' 14 bp overhang on each of the V primers is used. In the secondary PCR, the same Read2-tagX-P7 primer on the V side is employed. On the C side a strategy similar to that used with TCRβ amplification is used to avoid variants among the different IgG segments and their known alleles. The primer sequence (AATGATACGGCGACCAC-CGAGATCTGGGAAGACGATGGGCCCTTGGTGGA) (SEQ ID NO: 130) comprises the sequence of the C segment from positions 3-19 and 21-28 and it skips position 20 that has a different base in at least one of the different IgG alleles and the sequence for P5 that is can be used for formation of the clusters as shown in FIG. 4A.

A multiplexed PCR using three pools of primers corresponding to the three frames was carried out using cDNA as a template. After primary and secondary PCRs, the products were run on an agarose gel. Single bands with the appropriate relative sizes were obtained from the three pools.

In one embodiment, three different reactions from a single sample are mixed at equimolar ratio and subjected to sequencing. Sequencing is done from both directions using the two Illumina primers, such as described above. 100 bp is sequenced from each side. The maximal germ line sequences encompassing the D+J segments are ~30 bp longer for BCR than TCR. Therefore if the net result of nucleotide removal and addition at the joints (N and P nucleotides) generate a similar distribution for IgH and TCRβ, on average 90 bp and maximally 120 bp of sequence after the C segment is sufficient to reach the 3' of the V segment. Therefore, in most cases, the sequence from the C primer is sufficient to reach the V segment. Sequencing from one of the Illumina adapters identifies the V segment used as well as somatic hypermutations in the V segments. Different pieces of the V segments are sequenced depending on which of the three amplification reactions the sequence originated from. The full sequence of the BCR can be aligned from different reads that originated from different amplification reactions. The sequencing reaction from the one end showing the full CDR3 sequence greatly facilitates the accurate alignment of different reads.

EXAMPLE 3

Amplification of IgH Sequences from Genomic DNA

In this example, amplification of IgH sequences from genomic DNA is described. Such amplification is advantageous because (1) the level of a clonotype in genomic DNA can be readily converted to number of cells, and (2) in some lymphoid neoplasms, RNA may not be expressed for the relevant immune receptor rearrangement.

Amplification of immune receptor rearrangement is important for the detection of lymphoid neoplasms. B cell neoplasms are more common than T cell tumors and IgH is the most common rearranged immune receptor in B cell neoplasms. Because of somatic hypermutation, reliability of amplifying of IgH from genomic DNA may be increase by amplifying with multiple primers for each V segment, although there is a risk of differential amplification. In amplification from genomic DNA, the same V primers were used that were used in amplification from cDNA. Each V segment is amplified by 3 primers (in 3 distinct regions of the V segment: A, B, and C) in three different reactions (Tables 5-7, respectively) (see FIG. 4A).

TABLE 5

Human IgH V Segment Primers for Reaction A (All the primers have a common 14 bp (AGATCGGAAGAGCA) (SEQ ID NO 165) appended to their 5' end)

| Sequence | SEQ ID NO |
|---|---|
| TCGCAGACCCTCTCACTCACCTGTG | 62 |
| GATCTCCTGTAAGGGTTCTGGATACAGCT | 61 |
| AAACCCACACAGACCCTCACGCTGAC | 44 |
| AAACCCACAGAGACCCTCACGCTGAC | 45 |
| AAACCCACACAGACCCTCACACTGAC | 46 |
| CCTCAGTGAAGGTCTCCTGCAAGG | 40 |
| CCTCGGTGAAGGTCTCCTGCAAGG | 41 |
| CCTCAGTGAAGGTTTCCTGCAAGG | 42 |
| GGGCTACAGTGAAAATCTCCTGCAAGG | 43 |
| CTTCGGAGACCCTGTCCCTCACCTG | 56 |
| CTTCGGACACCCTGTCCCTCACCTG | 57 |
| CTTCACAGACCCTGTCCCTCACCTG | 58 |
| CTTCGGAGACCCCGTCCCTCACCTG | 59 |
| CGGGGACCCTGTCCCTCACCTG | 60 |
| CTGGGGGGTCCCTGAGACTCTCCTG | 47 |
| CTGGGGGGTCCCTTAGACTCTCCTG | 48 |
| CAGGGCGGTCCCTGAGACTCTCCTG | 49 |
| CAGGGCCGTCCCTGAGACTCTCCTG | 50 |
| CTGGGGGGTCCCTGAAACTCTCCTG | 51 |
| CTGGCAGGTCCCTGAGACTCTCCTG | 52 |
| CTGGAGGGTCCCTGAGACTCTCCTG | 53 |

TABLE 5-continued

Human IgH V Segment Primers for Reaction A
(All the primers have a common 14 bp
(AGATCGGAAGAGCA) (SEQ ID NO 165) appended to
their 5' end)

| Sequence | SEQ ID NO |
| --- | --- |
| CTGGGAGGTCCCTGAGACTCTCCTG | 54 |
| TGGGGGGGCCCTGAGACTCTCCT | 55 |

TABLE 6

Human IgH V Segment Primers for Reaction B
(All the primers have a common 14 bp
(AGATCGGAAGAGCA) (SEQ ID NO 165) appended to
their 5' end)

| Sequence | SEQ ID NO |
| --- | --- |
| TGGATCAGGCAGTCCCCATCGAGAG | 63 |
| GCTGGGTGCGCCAGATGCCC | 64 |
| GTGTGAGCTGGATCCGTCAGCC | 131 |
| GTGTGGGCTGGATCCGTCAGCC | 132 |
| GTGCGACAGGCCCCTGGACAA | 67 |
| GGGTGCGACAGGCCACTGGACAA | 68 |
| GTGCGCCAGGCCCCCGGACAA | 69 |
| GGGTGCGACAGGCTCGTGGACAA | 70 |
| GGGTGCAACAGGCCCCTGGAAAA | 71 |
| GGGTGCGACAGGCTCCTGGAAAA | 72 |
| GTGCGACAGGCCCCCGGACAA | 73 |
| GTGCGACAGGCCCCCAGACAA | 74 |
| TCCGCCAGCCCCCAGGGAAGG | 75 |
| TCCGGCAGCCCCCAGGGAAGG | 76 |
| TCCGGCAGCCACCAGGGAAGG | 77 |
| TCCGCCAGCACCCAGGGAAGG | 78 |
| TCCGGCAGCCCGCCGGGAA | 79 |
| TCCGGCAGCCGCCGGGAA | 80 |
| TCCGGCAGCCCGCTGGGAAGG | 81 |
| TCCGCCAGCCCCTAGGGAAGG | 82 |
| GGTCCGCCAGGCTCCAGGGAA | 83 |
| GTTCCGCCAGGCTCCAGGGAA | 84 |
| GGTCCGCCAGGCTTCCGGGAA | 85 |
| GGTCCGTCAAGCTCCGGGGAA | 86 |
| GATCCGCCAGGCTCCAGGGAA | 87 |
| GGTCCGCCAAGCTCCAGGGAA | 88 |
| GGTCCGCCAGGCTCCAGGCAA | 89 |
| GGTCCGCCAGGCCCCAGGCAA | 90 |
| GGTCCGCCAGGCTCCGGGCAA | 91 |

TABLE 6-continued

Human IgH V Segment Primers for Reaction B
(All the primers have a common 14 bp
(AGATCGGAAGAGCA) (SEQ ID NO 165) appended to
their 5' end)

| Sequence | SEQ ID NO |
| --- | --- |
| GGGTCCGTCAAGCTCCAGGGAAGG | 92 |
| CTGGGTCCGCCAAGCTACAGGAAA | 93 |
| GGTCCGCCAGCCTCCAGGGAA | 94 |
| GGTCCGGCAAGCTCCAGGGAA | 95 |
| GTGCGAGCTGGATCCGTCAGCC | 133 |

TABLE 7

Human IgH V Segment Primers for Reaction C
(All the primers have a common 14 bp
(AGATCGGAAGAGCA) (SEQ ID NO 165) appended
to their 5' end)

| Sequence | SEQ ID NO |
| --- | --- |
| GCAGCCTAAAGGCTGAGGACACTG | 134 |
| CTCTGTGACTCCCGAGGACACGGCT | 97 |
| AGTGGAGCAGCCTGAAGGCCTC | 98 |
| TGACCAACATGGACCCTGTGGACAC | 99 |
| ACATGGAGCTGAGCAGCCTGAGATC | 100 |
| ACATGGAGCTGAGCAGGCTGAGATC | 101 |
| ACATGGAGCTGAGGAGCCTGAGATC | 102 |
| ACATGGAGCTGAGGAGCCTAAGATCTGA | 103 |
| GAGCTCTGTGACCGCCGCGGAC | 104 |
| GAGCTCTGTGACCGCCGTGGACA | 105 |
| GAGCTCTGTGACCGCTGCAGACACG | 106 |
| GAGCTCTGTGACCGCTGCGGACA | 107 |
| GAGCTCTGTGACTGCCGCAGACACG | 108 |
| GAGCTCTGTGACTGCAGCAGACACG | 109 |
| GAGCTCTGTGACTGCCGCGGACA | 110 |
| GAGCTCTGTGACCGCGGACGCG | 111 |
| GGCTCTGTGACCGCCGCGGAC | 112 |
| GAGCTCTGTGACCGCCGCAGACA | 113 |
| GAGCTCTGTGACCGCTGACACGG | 114 |
| CAAATGAACAGCCTGAGAGCCGAGGACA | 115 |
| CAAATGAACAGCCTGAAAACCGAGGACA | 116 |
| CAAATGAACAGTCTGAAAACCGAGGACA | 117 |
| CAAATGATCAGCCTGAAAACCGAGGACA | 118 |
| CAAATGAACAGTCTGAGAACTGAGGACACC | 119 |
| CAAATGAACAGTCTGAGAGCCGAGGACA | 120 |

TABLE 7-continued

Human IgH V Segment Primers for Reaction C
(All the primers have a common 14 bp
(AGATCGGAAGAGCA) (SEQ ID NO 165) appended
to their 5' end)

| Sequence | SEQ ID NO |
|---|---|
| CAAATGAACAGCCTGAGAGCTGAGGACA | 121 |
| CAAATGAGCAGCCTGAGAGCTGAGGACA | 122 |
| CAAATGAACAGCCTGAGAGACGAGGACA | 123 |
| CAAATGGGCAGCCTGAGAGCTGAGGACA | 124 |
| CAAATGAACAGCCTGAGAGCCGGGGA | 125 |
| CAAATGAACAGTCTGAGAGCTGAGGACA | 126 |
| CAAATGAGCAGTCTGAGAGCTGAGGACA | 127 |
| GCACGCTAAAGGCTGAGGACACTG | 135 |

Amplification of IgH from genomic DNA has several differences from its amplification from cDNA. The C segment gets attached to the VDJ region through splicing and hence sequences of the C segment can be used for amplification from cDNA but not genomic DNA. The use of C segment allows the use of two distinct primers in the $1^{st}$ and $2^{nd}$ amplifications increasing the specificity. For the amplification from genomic DNA we have opted to use primers that are complementary to the J sequences (Table 8).

TABLE 8

Human IgH J Segment Primers*

| J Segment Primer | SEQ ID NO |
|---|---|
| ACGAGCCTCATGCGTAGANct cacCTGAGGAGACGGTGACC | 136 |
| ACGAGCCTCATGCGTAGANct cacCTGAGGAGACAGTGACC | 137 |
| ACGAGCCTCATGCGTAGANct tacCTGAAGAGACGGTGACC | 138 |
| ACGAGCCTCATGCGTAGANct tacCTGAGGAGACGGTGACC | 139 |

*The J segment primers used. The 18 by on the 5' are common sequences that are appended to the sequence complementary to the J segment in order to allow the second stage amplification. The position N signifies one random position in order to obtain diversity in the sequenced clusters. The small letter sequence are in the intron, and the capital letter sequences in the 3' of the sequence are in the exon. The letters in italics emphasize the bases that differ among the primers.

These primers span the exon-intron boundaries, and the four primers utilized amplify the different J segments and alleles described in the IMGT database. Primers of the second stage do not have any sequences complementary to genomic sequences.

Using the J primers over constant region primers complementary to the IgG constant region allows the assessment of the other classes (IgM, IgD, IgA, and IgE).

In the case of cDNA there is a choice of whether to use the J primer or the constant region primers. Several constant region primers can be used to amplify all the classes and sequence some of the constant region before entering into the J sequence in order to link the information on the clonotype and its specific class. The sequencing reads for many of the sequencing technologies are short and would be difficult to accomplish this. One of the current platforms on the market (454 Roche) does have a longer read but it has lower throughput than other platforms. As these technologies develop further this option become possible. With the current short reads (<100 bp) our work on the genomic DNA assay suggests that for amplification from cDNA can be done using both the J and the C priming approach. We can implement amplification using J primers from cDNA. However given that the exonic segment of these primers may be too short for specific amplification from cDNA, potentially the first stage PCR can be done using a set of constant region primers encompassing all the different classes (and the V segment primers on the other side as we have demonstrated). Then the second stage PCR can be done with the J primers which are long enough to have high specificity for second stage PCR which is utilizing a low complexity template. The products are then be sequenced. As stated above, the disadvantage compared with the scheme demonstrated for IgG is that somatic mutations in the J sequence may inhibit the amplification. The advantage is that all the different classes are assessed, even though the information on the class of each clonotype is not fully determined. Potentially one can do class specific amplification IgG, IgM, IgD, IgA, or IgE and compare with the overall picture obtained from using all the primers followed by J primer. For example one can compare clonotype profile obtained from IgG amplification to that using all the primers followed by J primer. The difference presumably would be due to somatic mutation in the J primer (which can be readily identified in the reaction using the IgG printer) and clonotypes of the other classes, which can then be quantified.

The use of J primers in cDNA also allows the direct comparison between the cDNA and genomic DNA results. This would provide expression level information at a clonotype level and can indeed have functional relevance. One aspect of this invention is that comparing the clonotype profile of cDNA and genomic DNA from the same blood or other biological sample identifies clonotypes that have different frequencies indicating unusually high or low expression per cell. This functional information can be utilized to predict whether a clonotype is likely to be correlating with disease or not. In addition the level of expression per cell of a clonotype correlating with a disease can be used to determine the disease activity or the likelihood of a disease outcome. For example obtaining the same level in the cDNA assay for a correlating clonotype in two individuals may still indicate the patients have different disease activities if the clonotypes level of expression per cell (as determined by comparison with the genomic DNA clonotype profiling) is different.

The second stage PCR is to attach the sequences necessary for the amplification. The primers used in the second stage are listed in Table 9.

TABLE 9

Common primers*

| Primer Sequence | Utilization | SEQ ID NO |
|---|---|---|
| AATGATACGGCGACCACCGAGATCT | Third stage PCR | 140 |
| CAAGCAGAAGACGGCATACGAGAT | Third stage PCR | 37 |

TABLE 9-continued

Common primers*

| Primer Sequence | Utilization | SEQ ID NO |
|---|---|---|
| CAAGCAGAAGACGGCATACGAGATNNNNNNNGTGAC TGGAGTTCAGACGTGTGCTCTTCCGATCT | Common second stage PCR | 141 |
| TGATGGCTCAAACAAGGAGACCT | First stage PCR for mouse TCRβ | 192 |
| AATGATACGGCGACCACCGAGATCTGACCTTGGGT GGAGTCACATTTCTCAGATCCT | Second stage PCR for mouse TCRβ | 193 |
| AATGATACGGCGACCACCGAGATCTACACTCTTTC CCTACACGAGCCTCATGCGTAGA | Second stage for human IgH from genomic DNA | 194 |

*Third stage is an optional amplification stage for all the assays (e.g, mouse TCRβ and human IgH). It is done to ensure the integrity of the end sequences that hybridize to the oligonucleotides attached to the flow cell. The common second stage primer is used in all the assays (e.g, mouse TCRβ and human IgH). Note that use of N in the common second stage primer is to denote the fact that each of these primers contains a unique 6 base pair tag to allow samples to be later identified.

Amplification is possible using the above primers and other sequences that are substantially similar. FIGS. 8A-8B show examples of such amplifications, which were successful at least in the range of genomic DNA 50-2,000 μg in 20 μl of input genomic DNA.

The assay needs to accommodate a large dynamic range of DNA. Biopsy samples may not have large amount of material, but given that the tumor is likely to be greatly enriched there is no need for a large amount of starting material. On the other hand, one million cells will have ~6 μg of genomic DNA. PBMC containing 1 million B cells will likely have ~20 μg of genomic DNA. To be able to assess 1 million B cells, ~6.6 μg of genomic DNA is used in each of the 3 PCR reactions. Of note is that if there is a somatic mutation in the sequence complementary to one of the primers then in this example only ~660K B cells are being interrogated. It is useful if the assay works over the range of 50 to 10,000 ng. The assay has been demonstrated to work in the range of 50-2,000 ng of DNA in 20 μl. By scaling up the reaction to 100 μl, 10 μg of DNA can be used.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

DEFINITIONS

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6th edition (Saunders, 2007).

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al. U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

"Clonality" as used herein means a measure of the degree to which the distribution of clonotype abundances among clonotypes of a repertoire is skewed to a single or a few clonotypes. Roughly, clonality is an inverse measure of clonotype diversity. Many measures or statistics are available from ecology describing species-abundance relationships that may be used for clonality measures in accordance with the invention, e.g. Chapters 17 & 18, in Pielou, An Introduction to Mathematical Ecology, (Wiley-Interscience, 1969). In one aspect, a clonality measure used with the invention is a function of a clonotype profile (that is, the number of distinct clonotypes detected and their abundances), so that after a clonotype profile is measured, clonality may be computed from it to give a single number. One clonality measure is Simpson's measure, which is simply the probability that two randomly drawn clonotypes will be the same. Other clonality measures include information-based measures and McIntosh's diversity index, disclosed in Pielou (cited above).

"Clonotype" means a recombined nucleotide sequence of a T cell or B cell encoding a T cell receptor (TCR) or B cell receptor (BCR), or a portion thereof. In one aspect, a collection of all the distinct clonotypes of a population of lymphocytes of an individual is a repertoire of such population, e.g. Arstila et al, Science, 286: 958-961 (1999); Yassai et al, Immunogenetics, 61: 493-502 (2009); Kedzierska et al, Mol. Immunol., 45(3): 607-618 (2008); and the like. As used herein, "clonotype profile," or "repertoire profile," is a tabulation of clonotypes of a sample of T cells and/or B cells (such as a peripheral blood sample containing such cells) that includes substantially all of the repertoire's clonotypes and their relative abundances. "Clonotype profile," "repertoire profile," and "repertoire" are used herein interchangeably. (That is, the term "repertoire," as discussed more fully below, means a repertoire measured from a sample of lymphocytes). In one aspect of the invention, clonotypes comprise portions of an immunoglobulin heavy chain (IgH) or a TCR β chain. In other aspects of the invention, clonotypes may be based on ether recombined molecules, such as immunoglobulin light chains or TCRα chains, or portions thereof.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Internal standard" means a nucleic acid sequence that is amplified in the same amplification reaction as one or more target polynucleotides in order to permit absolute or relative quantification of the target polynucleotides in a sample. An internal standard may be endogenous or exogenous. That is, an internal standard may occur naturally in the sample, or it may be added to the sample prior to amplification. In one aspect, multiple exogenous internal standard sequences may be added to a reaction mixture in a series of predetermined concentrations to provide a calibration to which a target amplicon may be compared to determine the quantity of its corresponding target polynucleotide in a sample. Selection of the number, sequences, lengths, and other characteristics of exogenous internal standards is a routine design choice for one of ordinary skill in the art. Preferably, endogenous internal standards, also referred to herein as "reference sequences," are sequences natural to a sample that correspond to minimally regulated genes that exhibit a constant and cell cycle-independent level of transcription, e.g. Selvey et al, Mol. Cell Probes, 15: 307-311 (2001). Exemplary reference sequences include, but are not limited to, sequences from the following genes: GAPDH, β$_2$-microglobulin, 18S ribosomal RNA, and β-actin (although see Selvey et al, cited above).

"Kit" refers to any delivery system for delivering materials or reagents for carrying out a method of the invention. In the context of reaction assays, such delivery systems include systems that allow for the storage, transport, or delivery of reaction reagents (e.g., primers, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains primers.

"Lymphoid neoplasm" means an abnormal proliferation of lymphocytes that may be malignant or non-malignant. A lymphoid cancer is a malignant lymphoid neoplasm. Lymphoid neoplasms are the result of, or are associated with, lymphoproliferative disorders, including but not limited to, follicular lymphoma, chronic lymphocytic leukemia (CLL), acute lymphocytic leukemia (ALL), hairy cell leukemia, lymphomas, multiple myeloma, post-transplant lymphoproliferative disorder, mantle cell lymphoma (MCL), diffuse large B cell lymphoma (DLBCL), T cell lymphoma, or the like, e.g. Jaffe et al, Blood, 112: 4384-4399 (2008); Swerdlow et al, WHO Classification of Tumours of Haematopoietic and Lymphoid Tissues (e. 4$^{th}$) (IARC Press, 2008).

"Pecent homologous," "percent identical," or like terms used in reference to the comparison of a reference sequence and another sequence ("comparison sequence") mean that in an optimal alignment between the two sequences, the comparison sequence is identical to the reference sequence in a number of subunit positions equivalent to the indicated percentage, the subunits being nucleotides for polynucleotide comparisons or amino acids for polypeptide comparisons. As used herein, an "optimal alignment" of sequences being compared is one that maximizes matches between subunits and minimizes the number of gaps employed in constructing an alignment. Percent identities may be determined with commercially available implementations of algorithms, such as that described by Needleman and Wunsch, J. Mol. Biol., 48: 443-453 (1970)("GAP" program of Wisconsin Sequence Analysis Package, Genetics Computer Group, Madison, Wis.), or the like. Other software packages in the art for constructing alignments and calculating percentage identity or other measures of similarity include the "BestFit" program, based on the algorithm of Smith and Waterman, Advances in Applied Mathematics, 2: 482-489 (1981) (Wisconsin Sequence Analysis Package, Genetics Computer Group, Madison, Wis.). In other words, for example, to obtain a polynucleotide having a nucleotide sequence at least 95 percent identical to a reference nucleotide sequence, up to five percent of the nucleotides in the reference sequence may be deleted or substituted with another nucleotide, or a number of nucleotides up to five percent of the total number of nucleotides in the reference sequence may be inserted into the reference sequence.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified. Typically, the number of target sequences in a multiplex PCR is in the range of from 2 to 50, or from 2 to 40, or from 2 to 30. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences or internal standards that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Quality score" means a measure of the probability that a base assignment at a particular sequence location is correct. A variety methods are well known to those of ordinary skill for calculating quality scores for particular circumstances, such as, for bases called as a result of different sequencing chemistries, detection systems, base-calling algorithms, and so on. Generally, quality score values are monotonically related to probabilities of correct base calling. For example, a quality score, or Q, of 10 may mean that there is a 90 percent chance that a base is called correctly, a Q of 20 may mean that there is a 99 percent chance that a base is called correctly, and so on. For some sequencing platforms, particularly those using sequencing-by-synthesis chemistries, average quality scores decrease as a function of sequence read length, so that quality scores at the beginning of a sequence read are higher than those at the end of a sequence read, such declines being due to phenomena such as incomplete extensions, carry forward extensions, loss of template, loss of polymerase, capping failures, deprotection failures, and the like.

"Repertoire", or "immune repertoire", means a set of distinct recombined nucleotide sequences that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. In one aspect, a population of lymphocytes from which a repertoire is determined is taken from one or more tissue samples, such as one or more blood samples. A member nucleotide sequence of a repertoire is referred to herein as a "clonotype." In one aspect, clonotypes of a repertoire comprises any segment of nucleic acid common to a T cell or a B cell population which has undergone somatic recombination during the development of TCRs or BCRs, including normal or aberrant (e.g. associated with cancers) precursor molecules thereof, including, but not limited to, any of the following: an immunoglobulin heavy chain (IgH) or subsets thereof (e.g. an IgH variable region, CDR3 region, or the like), incomplete IgH molecules, an immunoglobulin light chain or subsets thereof (e.g. a variable region, CDR region, or the like), T cell receptor α chain or subsets thereof, T cell receptor β chain or subsets thereof (e.g. variable region, CDR3, V(D)J region, or the like), a CDR (including CDR1, CDR2 or CDR3, of either TCRs or BCRs, or combinations of such CDRs), V(D)J regions of either TCRs or BCRs, hypermutated regions of IgH variable regions, or the like. In one aspect, nucleic acid segments defining clonotypes of a repertoire are selected so that their diversity (i.e. the number of distinct nucleic acid sequences in the set) is large enough so that substantially every T cell or B cell or clone thereof in an individual carries a unique nucleic acid sequence of such repertoire. That is, in accordance with the invention, a practitioner may select for defining clonotypes a particular segment or region of recombined nucleic acids that encode TCRs or BCRs that do not reflect the full diversity of a population of T cells or B cells; however, preferably, clonotypes are defined so that they do reflect the diversity of the population of T cells and/or B cells from which they are derived. That is, preferably each different clone of a sample has different clonotype. (Of course, in some applications, there will be multiple copies of one or more particular clonotypes within a profile, such as in the case of samples from leukemia or lymphoma patients). In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In one embodiment, a repertoire comprising human TCR β chains or fragments thereof comprises a number of distinct nucleotide sequences in the range of from $0.1 \times 10^6$ to $1.8 \times 10^6$, or in the range of from $0.5 \times 10^6$ to $1.5 \times 10^7$, or in the range of from $0.8 \times 10^6$ to $1.2 \times 10^6$. In another embodiment, a repertoire comprising human IgH chains or fragments thereof comprises a number of distinct nucleotide sequences in the range of from $0.1 \times 10^6$ to $1.8 \times 10^6$, or in the range of from $0.5 \times 10^6$ to $1.5 \times 10^6$, or in the range of from $0.8 \times 10^6$ to $1.2 \times 10^6$. In a particular embodiment, a repertoire of the invention comprises a set of nucleotide sequences encoding substantially all segments of the V(D)J region of an IgH chain. In one aspect, "substantially all" as used herein means every segment having a relative abundance of 0.001 percent or higher; or in another aspect, "substantially all" as used herein means every segment having a relative abundance of 0.0001 percent or higher. In another particular embodiment, a repertoire of the invention comprises a set of nucleotide sequences that encodes substantially all segments of the V(D)J region of a TCR β chain. In another embodiment, a repertoire of the invention comprises a set of nucleotide sequences having lengths in the range of from 25-200 nucleotides and including segments of the V, D, and J regions of a TCR β chain. In another embodiment, a repertoire of the invention comprises a set of nucleotide sequences having lengths in the range of from 25-200 nucleotides and including segments of the V, D, and J regions of an IgH chain. In another embodiment, a repertoire of the invention comprises a number of distinct nucleotide sequences that is substantially equivalent to the number of lymphocytes expressing a distinct IgH chain. In another embodiment, a repertoire of the invention comprises a number of distinct nucleotide sequences that is substantially equivalent to the number of lymphocytes expressing a distinct TCR β chain. In still another embodiment. "substantially equivalent" means that with ninety-nine percent probability a repertoire of nucleotide sequences will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. The sets of clonotypes described in the foregoing two sentences are sometimes referred to herein as representing the "full repertoire" of IgH and/or TCRβ sequences. As mentioned above, when measuring or generating a clonotype profile (or repertoire profile), a sufficiently large sample of lymphocytes is obtained so that such profile provides a reasonably accurate representation of a repertoire for a particular application. In one aspect, samples comprising from $10^5$ to $10^7$ lymphocytes are employed, especially when obtained from peripheral blood samples of from 1-10 mL.

"Sequence tag" (or "tag") means an oligonucleotide that is attached to a polynucleotide or template and is used to identify and/or track the polynucleotide or template in a reaction. An oligonucleotide tag may be attached to the 3'- or 5'-end of a polynucleotide or template or it may be inserted into the interior of such polynucleotide template to form a linear conjugate, sometime referred to herein as a "tagged polynucleotide," or "tagged template," or "tag-polynucleotide conjugate," or the like. Oligonucleotide tags may vary widely in size and compositions; the following references provide guidance for selecting sets of oligonucleotide tags appropriate for particular embodiments: Brenner, U.S. Pat. No. 5,635, 400; Brenner et al, Proc. Natl. Acad. Sci., 97: 1665-1670 (2000); Church et al, European patent publication 0 303 459; Shoemaker et al, Nature Genetics, 14: 450-456 (1996); Morris et al, European patent publication 0799897A1; Wallace, U.S. Pat. No. 5,981,179; and the like. Lengths and compositions of oligonucleotide tags can vary widely, and the selection of particular lengths and/or compositions depends on several factors including, without limitation, how tags are used to generate a readout, e.g. via a hybridization reaction or via an enzymatic reaction, such as sequencing; whether they are labeled, e.g. with a fluorescent dye or the like: the number of distinguishable oligonucleotide tags required to unambiguously identify a set of polynucleotides, and the like, and how different must tags of a set be in order to ensure reliable identification, e.g. freedom from cross hybridization or misidentification from sequencing errors. In one aspect, oligonucleotide tags can each have a length within a range of from 2 to 36 nucleotides, or from 4 to 30 nucleotides, or from 8 to 20 nucleotides, or from 6 to 10 nucleotides, respectively. In one aspect, sets of tags are used wherein each oligonucleotide tag of a set has a unique nucleotide sequence that differs from that of every other tag of the same set by at least two bases; in another aspect, sets of tags are used wherein the sequence of each tag of a set differs from that of every other tag of the same set by at least three bases.

What is claimed is:

1. A method for determining a clonotype profile of T-cell receptors and/or B-cell receptors of an individual, the method comprising the steps of:
   a) obtaining a nucleic acid sample from T-cells and/or B-cells of the individual;
   b) spatially isolating individual molecules derived from such nucleic acid sample, the individual molecules comprising nested sets of templates each generated from a nucleic acid in the sample and each containing a somatically rearranged region or a portion thereof, each nested set comprising a plurality of overlapping templates such that every template of the plurality has a common end and a different end and each nested set being capable of producing a plurality of sequence reads each extending in the same direction and each starting from a different position on the nucleic acid from which the nested set was generated;
   c) bidirectionally sequencing said spatially isolated individual molecules to generate for each nested set a plurality of sequence reads including at least one forward sequence read and at least one reverse sequence read so that at least 1000 clonotypes each having a sequence length of at least 30 nucleotides are determined; and
   d) determining abundances of the clonotypes of the different sequences of the nucleic acid molecules from the nucleic acid sample to generate the clonotype profile.

2. The method of claim 1 wherein each of said somatically rearranged regions comprise a V region and a J region, and wherein each of said plurality of sequence reads starts from a different position in the V region and extends in the direction of its associated J region.

3. The method of claim 1 wherein at least one of said forward sequence reads and at least one of said reverse sequence reads have an overlap region such that bases of such overlap region are determined by a reverse complementary relationship between such sequence reads.

4. The method of claim 3 wherein each of said somatically rearranged regions comprise a V region and a J region, and wherein said step of sequencing further includes determining a sequence of each of said individual nucleic acid molecules from one or more of its said forward sequence reads and at least one of said reverse sequence reads starting from a position in a J region and extending in the direction of its associated V region.

5. The method of claim 1 wherein said individual molecules comprise nucleic acids selected from the group consisting of complete IeI molecules, incomplete IgH molecules, complete IgK molecules, IgK inactive molecules, TCRβ molecules, TCRγ molecules, complete TCRδ molecules, and incomplete TCRδ molecules.

6. The method of claim 1 wherein said individual molecules comprise a repertoire of clonotypes present at a frequency of 0.01 percent or greater with a probability of ninety-nine percent.

7. The method of claim 1 wherein said nucleic acid sample is obtained from peripheral blood or bone marrow of said individual.

8. The method of claim 1 wherein said step of spatially isolating includes disposing said individual molecules on a solid surface and amplifying said individual molecules thereon to form isolated clonal populations thereof.

9. The method of claim 8 wherein said amplifying is carried out by bridge PCRs.

10. The method of claim 1 wherein said plurality of sequence reads is generated by annealing a primer to a primer binding site on each template of said nested set of templates and extending the primer with a DNA polymerase.

11. The method of claim 10 wherein at least one of said plurality of sequence reads overlaps at least one of said primer binding sites.

12. The method of claim 1 wherein said step of sequencing comprises generating said sequence reads having monotonically decreasing quality scores.

13. The method of claim 12 wherein said monotonically decreasing quality scores are such that said sequence reads have error rates no better than the following: 0.2 percent of sequence reads contain at least one error in base positions 1 to 50, 0.2 to 1.0 percent of sequence reads contain at least one error in positions 51-75, 0.5 to 1.5 percent of sequence reads contain at least one error in positions 76-100.

14. The method of claim 1 wherein said nucleic acid sample is from B-cells of said individual.

* * * * *

UNITED STATES PATENT AND TRADEMARK OFFICE
CERTIFICATE OF CORRECTION

| | | |
|---|---|---|
| PATENT NO. | : 8,691,510 B2 | Page 1 of 1 |
| APPLICATION NO. | : 13/100389 | |
| DATED | : April 8, 2014 | |
| INVENTOR(S) | : Malek Faham et al. | |

It is certified that error appears in the above-identified patent and that said Letters Patent is hereby corrected as shown below:

On the title page, item [60] under the Related U.S. Application Data, item (60), "provisional application No. 61/445,743, filed on Oct. 25, 2010" should read --provisional application No. 61/455,743, filed on Oct. 25, 2010--

In the Claims

COLUMN 86, LINE 32, CLAIM 5
"complete lei" should read --complete IgH--

Signed and Sealed this
Thirteenth Day of January, 2015

Michelle K. Lee
*Deputy Director of the United States Patent and Trademark Office*